United States Patent [19]

Wetmur

[11] Patent Number: 5,877,280
[45] Date of Patent: Mar. 2, 1999

[54] THERMOSTABLE MUTS PROTEINS

[75] Inventor: James G. Wetmur, Scarsdale, N.Y.

[73] Assignee: The Mount Sinai School of Medicine of the City University of New York, New York, N.Y.

[21] Appl. No.: 468,558

[22] Filed: Jun. 6, 1995

[51] Int. Cl.[6] .................. C07K 1/00; C12Q 1/68; G01N 33/566; G01N 33/00
[52] U.S. Cl. ................ 530/350; 435/6; 435/91.1; 436/501; 436/94
[58] Field of Search ............ 435/6, 91.1; 436/501, 436/94; 935/77, 78; 530/350

[56] References Cited

U.S. PATENT DOCUMENTS

| 4,994,368 | 2/1991 | Goodman et al. | 435/6 |
|---|---|---|---|
| 5,422,253 | 6/1995 | Dahlberg et al. | 435/91.53 |

FOREIGN PATENT DOCUMENTS

| WO 93/22462 | 11/1993 | WIPO . | |
|---|---|---|---|
| WO 95/12689 | 5/1994 | WIPO | C12Q 1/68 |
| WO 94/14978 | 7/1994 | WIPO | C12Q 1/68 |
| WO 95/29258 | 11/1995 | WIPO . | |

OTHER PUBLICATIONS

Thomas Devlin "Biochemistry with clinical correlations", A wiley Medical Publication, p. 850, 1982.

Priebe et al., "Nucleotide Sequence of the hexA Gene for DNA Mismatch Repair in Streptococcus pneumoniae and Homology of hexA to mutS of *Escherichia coli* and *Salmonella typhimurium*" Journal of Bacteriology, vol. 170, pp. 190–196, Jan. 1988.

Le et al. "*Azobacter vinelandii* mutS: Nucleotide Sequence and Mutant Analysis" Journal of Bacteriology, vol. 175, pp. 7707–7710, Dec. 1993.

Su, S. and Modrich, P., "*Escherichia coli* mutS–encoded protein binds to mismatched DNA base pairs", *Proc.Natl.Acad.Sci.USA*, 83:5057–5061 (1986).

Jiricny, J., et al., "Mismatch–containing oligonucleotide duplexes bound by the E. coli mutS–encoded protein", *Nucleic Acids Research*, 16(16) : 7843–7853 (1988).

Lishanski, A., et al., "Mutation detection by mismatch binding protein, MutS, in amplified DNA: Application to the cystic fibrosis gene", *Proc.Natl.Acad.Sci.USA*, 91: 2674–2678 (1994).

Fishel, R., et al., "Binding of Mismatched Microsatellite DNA Sequences by the Human MSH2 Protein", *Science*, 266:1403–1405 (1994).

Worth, L. Jr., et al., "Mismatch repair proteins MutS and MutL inhibit RecA–catalyzed strand transfer between diverged DNAs", *Proc.Natl.Acad.Sci.USA*, 91: 3238–3241 (1994).

Holland, P.M., et al., "Detection of specific polymerase chain reaction product by utilizing the 5'→3' exonuclease activity of *Thermus aquaticus* DNA polymerase", *Proc.Natl.Acad.Sci.USA*, 88:7276–7280 (1991).

(List continued on next page.)

*Primary Examiner*—Ardin H. Marschel
*Assistant Examiner*—Jezia Riley
*Attorney, Agent, or Firm*—Hamilton, Brook, Smith & Reynolds, P.C.

[57] ABSTRACT

Isolated nucleic acids which encode a thermostable protein which binds specifically to bulge loops in a heteroduplex nucleic acid and recombinant vectors comprising nucleic acid which encodes a thermostable protein which binds specifically to bulge loops in a heteroduplex nucleic acid are disclosed. Also disclosed are isolated thermostable proteins which bind specifically to bulge loops in a heteroduplex nucleic acid and host cells comprising a recombinant gene which can express a thermostable protein which binds specifically to bulge loops in a heteroduplex nucleic acid. Further disclosed are a method of reducing DNA misincorporation in an amplification reaction, methods for detecting a nucleic acid which includes a specific sequence, a method for amplifying a nucleic acid comprising a specific sequence, and a method for selecting against a nucleic acid comprising a specific sequence.

5 Claims, 8 Drawing Sheets

```
  1  MGKEEKELTP MLAQYHQFKS MYPDCLLLFR LGDFYELFYE DAVVGSKELG
 51  LVLTSRPAGK GRERIPMCGV PYHSANNYIA KLVNKGYKVA ICEQVEDPSK
101  AKGIVKRDVI RVITPGTFFE RETGGLCSLY RKGKSYLVSY LNLSVGEFIG
151  AKVKEEELID FLSKFNIREV LVKKGEKLPE KLEKVLKLHI TELEEEFFEE
201  GKEELLKDYG VPSIKAFGFQ DEDLSLSLGA VYRYAKATQK SFTPLIPKPK
251  PYVDEGYVKL DLKAVKGLEI TESIEGRKDL SLFKVVDRTL TGMGRRRLRF
301  RLLNPFRSIE RIRKVQEAVE ELINKREVLN EIRKTLEGHS DLERLVSRIS
351  SNMASPRELI HLKNSLRKAE ELRKILSLLD SEIFKEIEGS LLNLNKVADL
401  IDKTLVDDPP LEVKEGGLIK PGVNAYLDEL RFIRENAEKL LKEYEKKLKK
451  ETGIQSLKIG YNKVMGYYIE VTKANVKYVP EHFRRRQTLS NAERYTTEEL
501  QRLEEKILSA QTRINELEYE LYRELREEVV KELDKVGNNA TLIGEVDYIQ
551  SLAWLALEKG WVKPEVHEGY ELIIEEGKHP VIEEFTKNYV PNDTKLTEEE
601  PIHVITGPNM AGKSSYIRQV GVLTLLAHTG SFLPVKSARI PLVDAIFTRI
651  GSGDVLALGV STFMNEMLDV SNILNNATKR SLIILDEVGR GTSTYDGIAI
701  SKAIVKYISE KIGAKTLLAT HYLELTELER KVKGVKNYHM EVEETDEGIR
751  FLYILKEGRA KGSFGIDVAK LAGLPEEVVR EAKKILKELE GEKGKQEVLP
801  FLEETYKKSV DEEKLNFYEE IIKEIEEIDI GNTTPVKALL ILAELKERIK
851  SFIKR*
```

$M_r = 97655$

OTHER PUBLICATIONS

Ellis, L.A., et al., "MutS binding protects heteroduplex DNA from exonuclease digestion in vitro: a simple method for detecting mutations", *Nucleic Acids Research*, 22(13) :2710–2711 (1994).

Saiki, R.K., et al., "Primer–Directed Enzymatic Amplification of DNA with a Thermostable DNA Polymerase", *Science*, 239: 487–491 (1988).

Brown, P.O., "Genome scanning methods", *Current Opinion in Genetics and Development* 4:366–373 (1994).

Jonsson, J.J. and Weissman, S.M., "From mutation mapping to phenotype cloning", *Proc.Natl.Acad.Sci.USA* 92: 83–85 (1995).

Hayashi, K. and Yandell, D.W., "How Sensitive Is PCR–SSCP?", *Human Mutation* 2:338–346 (1993).

Youil, R., et al., "Screening for mutations by enzyme mismatch cleavage with T4 endonuclease VII", *Proc.Natl.Acad.Sci.USA* 92: 87–91 (1995).

Hsu, I. –C., et al., "Detection of DNA point mutations with DNA mismatch repair enzymes", *Carcinogenesis* 15(8) :1657–1662 (1994).

Fishel, R., et al., "Purified Human MSH2 Protein Binds to DNA Containing Mismatched Nucleotides", *Cancer Research* 54:5539–5542 (1994).

Au, K.G., et al., "Initiation of Methyl–directed Mismatch Repair", *J. Biol. Chem.,*267(17) : 12142–12148 (1992).

Biswas, I., and Hsieh, P., "Identification and Characterization of a Thermostable MutS Homolog from Thermus Aquaticus", *J. Biol. Chem.,*271 (9) : 5040–5048 (1996).

Takamatsu, S., et al., "Mismatch DNA Recognition Protein From an Extremely Thermophilic Bacterium, Thermus Thermophilus HB8", *Nucleic Acids Research*, 24 (4) : 640–647 (1996).

```
   1  ATGGGAAAAG AGGAGAAAGA GCTCACCCCC ATGCTCGCCC AGTATCACCA
  51  GTTCAAGAGC ATGTATCCCG ACTGCCTTCT TTTATTCAGG CTCGGGGACT
 101  TTTACGAGCT CTTTTACGAG GACGCGGTCG TCGGTTCTAA AGAGCTCGGT
 151  CTAGTTCTAA CTTCAAGACC CGCGGGAAAG GGAAGGGAAA GGATTCCCAT
 201  GTGCGGTGTT CCCTACCATT CTGCAAACAA CTATATAGCA AAGCTCGTTA
 251  ATAAGGGATA CAAGGTAGCA ATATGCGAGC AGGTTGAGGA CCCCTCAAAG
 301  GCAAAGGGAA TAGTAAAGAG GGACGTAATA AGAGTTATAA CACCTGGGAC
 351  CTTTTTTGAG AGGGAAACGG GAGGGCTTTG CTCCCTTTAC AGGAAGGGAA
 401  AGAGCTATCT CGTTTCTTAT CTTAACCTCT CGGTAGGTGA GTTCATAGGT
 451  GCAAAGGTAA AGGAGGAAGA GCTCATAGAC TTCCTCTCAA AGTTCAACAT
 501  AAGGGAGGTT CTTGTAAAGA AGGGAGAAAA GCTCCCCGAA AAGCTTGAGA
 551  AGGTTCTAAA GCTCCACATA ACGGAGCTTG AAGAGGAGTT CTTTGAGGAG
 601  GGAAAGGAGG AGCTTCTTAA GGATTACGGA GTTCCGTCGA TAAAAGCCTT
 651  CGGCTTTCAG GATGAGGATT TATCCCTTTC CCTCGGGGCT GTTTACAGGT
 701  ATGCAAAGGC GACACAGAAA TCTTTTACCC CTCTCATTCC AAAGCCCAAA
 751  CCTTACGTTG ACGAGGGATA CGTAAAGCTT GACCTCAAGG CAGTCAAAGG
 801  TCTTGAGATT ACCGAAAGCA TAGAAGGAAG AAAGGATTTA TCCCTGTTTA
 851  AGGTCGTTGA CAGAACCCTC ACGGGTATGG GGAGAAGGAG GCTGAGGTTC
 901  AGGCTTCTAA ACCCCTTCAG GAGCATAGAG AGAATAAGGA AGGTTCAGGA
 951  AGCAGTTGAG GAGCTAATAA ACAAGAGGGA GGTTCTGAAC GAGATAAGGA
1001  AAACCCTTGA GGGTATGTCC GACCTTGAGA GACTCGTATC CAGGATAAGC
1051  TCAAACATGG CAAGCCCAAG AGAACTTATA CACCTCAAAA ACTCCCTAAG
1101  GAAGGCGGAG GAGCTAAGGA AAATTTTATC TTTGCTTGAT TCCGAAATAT
1151  TTAAAGAGAT AGAAGGTTCT CTCCTTAACC TGAATAAAGT TGCGGACCTC
1201  ATTGATAAAA CGCTTGTTGA CGACCCTCCC CTGCACGTAA AAGAAGGGGG
1251  GCTTATAAAA CCCGGTGTTA ACGCATACCT TGATGAGCTT CGCTTCATAA
1301  GGGAGAATGC GGAAAAGCTC CTGAAGGAGT ATGAAAAGAA GCTGAAAAAA
1351  GAAACGGGAA TTCAGAGCTT AAAGATTGGA TACAACAAGG TTATGGGATA
1401  CTACATAGAG GTAACGAAGG CTAACGTAAA ATACGTTCCC GAACACTTCA
1451  GAAGAAGACA GACCCTTTCA AACGCGGAGA GATACACAAC CGAGGAGCTC
1501  CAGAGACTTG AGGAAAAGAT ACTTTCCGCC CAGACCCGCA TAAACGAGCT
1551  TGAGTATGAG CTTTACAGGG AGCTCAGGGA AGAGGTTGTT AAGGAGCTTG
1601  ATAAGGTAGG GAATAACGCA ACCCTCATAG GGGAGGTGGA CTACATCCAG
1651  TCCCTCGCCT GGCTTGCCCT TGAGAAGGGA TGGGTAAAGC CGGAAGTTCA
1701  CGAGGGATAT GAGCTGATAA TAGAGGAGGG AAAGCATCCC GTAATAGAGG
1751  AGTTCACGAA AAACTACGTC CCAAACGATA CGAAGCTAAC GGAAGAGGAG
1801  TTCATACACG TAATCACGGG CCCTAACATG GCGGGAAAGT CGAGCTACAT
1851  AAGACAGGTG GGCGTCCTCA CGCTCCTTGC TCATACAGGT AGCTTCCTTC
1901  CCGTAAAGAG TGCAAGGATA CCGCTGGTTG ATGCGATATT CACGAGAATA
1951  GGCTCGGGGG ACGTTCTGGC TCTGGGTGTT TCAACCTTCA TGAACGAGAT
2001  GCTTGACGTG TCAAACATAC TCAACAACGC AACGAAGAGG AGCTTAATAA
2051  TACTCGACGA GGTGGGAAGG GGAACCTCAA CCTACGACGG GATAGCGATA
2101  AGCAAGGCGA TAGTGAAATA CATAAGCGAG AAGATAGGGG CGAAAACGCT
2151  ACTCGCAACC CACTACCTTG AGCTAACCGA GCTTGAGAGA AAGGTAAAGG
2201  GAGTAAAGAA CTACCACATG GAGGTTGAGG AAACGGATGA GGGAATAAGG
2251  TTCTTATACA TACTGAAGGA GGGAAGGGCG AAGGGAAGCT TCGGCATAGA
2301  CGTCGCAAAA CTCGCGGGAC TGCCCGAGGA AGTTGTAAGG GAAGCAAAAA
2351  AGATACTGAA GGAGCTTGAA GGGGAAAAAG GAAAGCAGGA AGTTCTCCCC
2401  TTCCTTGAGG AGACCTATAA AAAGTCCGTT GATGAAGAGA AGCTGAACTT
2451  TTACGAAGAG ATAATAAAGG AGATAGAGGA GATAGATATA GGGAACACGA
2501  CTCCTGTTAA AGCCCTGCTC ATCCTTGCGG AGTTAAAGGA AAGGATAAAG
2551  AGCTTTATAA AGAGGTGA
```

G + C CONTENT: 47%

FIGURE 1

|     |            |            |            |            |            |
|-----|------------|------------|------------|------------|------------|
| 1   | MGKEEKELTP | MLAQYHQFKS | MYPDCLLLFR | LGDFYELFYE | DAVVGSKELG |
| 51  | LVLTSRPAGK | GRERIPMCGV | PYHSANNYIA | KLVNKGYKVA | ICEQVEDPSK |
| 101 | AKGIVKRDVI | RVITPGTFFE | RETGGLCSLY | RKGKSYLVSY | LNLSVGEFIG |
| 151 | AKVKEEELID | FLSKFNIREV | LVKKGEKLPE | KLEKVLKLHI | TELEEEFFEE |
| 201 | GKEELLKDYG | VPSIKAFGFQ | DEDLSLSLGA | VYRYAKATQK | SFTPLIPKPK |
| 251 | PYVDEGYVKL | DLKAVKGLEI | TESIEGRKDL | SLFKVVDRTL | TGMGRRRLRF |
| 301 | RLLNPFRSIE | RIRKVQEAVE | ELINKREVLN | EIRKTLEGMS | DLERLVSRIS |
| 351 | SNMASPRELI | HLKNSLRKAE | ELRKILSLLD | SEIFKEIEGS | LLNLNKVADL |
| 401 | IDKTLVDDPP | LHVKEGGLIK | PGVNAYLDEL | RFIRENAEKL | LKEYEKKLKK |
| 451 | ETGIQSLKIG | YNKVMGYYIE | VTKANVKYVP | EHFRRRQTLS | NAERYTTEEL |
| 501 | QRLEEKILSA | QTRINELEYE | LYRELREEVV | KELDKVGNNA | TLIGEVDYIQ |
| 551 | SLAWLALEKG | WVKPEVHEGY | ELIIEEGKHP | VIEEFTKNYV | PNDTKLTEEE |
| 601 | FIHVITGPNM | AGKSSYIRQV | GVLTLLAHTG | SFLPVKSARI | PLVDAIFTRI |
| 651 | GSGDVLALGV | STFMNEMLDV | SNILNNATKR | SLIILDEVGR | GTSTYDGIAI |
| 701 | SKAIVKYISE | KIGAKTLLAT | HYLELTELER | KVKGVKNYHM | EVEETDEGIR |
| 751 | FLYILKEGRA | KGSFGIDVAK | LAGLPEEVVR | EAKKILKELE | GEKGKQEVLP |
| 801 | FLEETYKKSV | DEEKLNFYEE | IIKEIEEIDI | GNTTPVKALL | ILAELKERIK |
| 851 | SFIKR*     |            |            |            |            |

```
   1  GTGAAGGTAA  CTCCCCTCAT  GGAACAGTAC  CTGAGAATAA  AAGAACAGTA
  51  CAAAGATTCC  ATTCTGCTGT  TTCGACTGGG  AGATTTTTAC  GAGGCGTTTT
 101  TCGAAGACGC  AAAGATCGTT  TCGAAGGTTC  TGAACATAGT  TCTCACAAGA
 151  AGGCAGGACG  CTCCCATGGC  GGGCATCCCG  TACCACGCGC  TGAACACCTA
 201  CCTGAAAAAG  CTCGTCGAAG  CGGGCTACAA  GGTGGCAATC  TGCGATCAAA
 251  TGGAAGAACC  TTCGAAGTCG  AAGAAATTGA  TCAGAAGGGA  AGTCACGCGC
 301  GTTGTCACTC  CCGGCTCCAT  CGTAGAGGAT  GAGTTTCTCA  GCGAAACGAA
 351  CAACTACATG  GCCGTTGTCT  CAGAAGAGAA  AGGACGGTAC  TGTACGGTTT
 401  TCTGTGATGT  CTCGACAGGT  GAGGTCCTGG  TTCATGAAAG  TTCAGACGAA
 451  CAGGAAACTT  TGGACCTGCT  GAAGAATTAC  TCCATTTCCC  AGATCATCTG
 501  TCCAGAGCAC  CTGAAATCTT  CTTTGAAGGA  ACGCTTTCCA  GGTGTTTACA
 551  CAGAAACCAT  AAGCGAGTGG  TATTTCTCAG  ATCTGGAAGA  AGTGGAAAAA
 601  GCCTACAATC  TGAAAGACAT  TCATCATTTC  GAGCTTTCGC  CCCTTGCGCT
 651  GAAAGCCCTT  GCGGCGCTGA  TAAAGTATGT  CAAGTACACG  ATGATCGGGG
 701  AAGATCTGAA  TCTGAAACCC  CCTCTTCTCA  TCTCCCAGAG  AGACTACATG
 751  ATACTCGATT  CCGCAACGGT  GGAAAATCTT  TCTTGGATTC  CCGGTGACAG
 801  GGGAAAGAAT  CTTTTCGATG  TGCTGAACAA  CACGGAAACT  CCTATGGGGG
 851  CTCGTCTTGG  GAAAAAGTGG  ATTCTCCACC  CTCTGGTCGA  CAGAAAACAG
 901  ATCGAAGAAA  GGCTCAAGGC  TGTGGAAAGA  CTGGTGAACG  ACAGGGTGAG
 951  CCTGGAGGAG  ATGAGGAACC  TTCTTTCGAA  CGTGAGGGAT  GTGGAGCGGA
1001  TCGTTTCGCG  GGTGGAGTAC  AACAGATCCG  TTCCCAGGGA  CTTAGTGGCA
1051  CTCAGAGAGA  CACTGGAGAT  CATCCCGAAA  CTGAACGAAG  TTCTTTCAAC
1101  CTTCGGTGTG  TTCAAGAAAC  TCGCTTTCCC  GGAAGGACTG  GTTGATCTGC
1151  TTCGAAAAGC  CATTGAAGAT  GATCCGGTGG  GAAGCCCCGG  CGAGGGAAAA
1201  GTTATAAAGA  GAGGATTCTC  ATCTGAACTC  GACGAATACA  GGGATCTTCT
1251  GGAACATGCC  GAAGAGAGGC  TCAAAGAGTT  CGAGGAGAAG  GAGAGAGAAA
1301  GAACAGGCAT  CCAAAAACTG  CGGGTTGGAT  ACAACCAGGT  TTTTGGTTAC
1351  TACATAGAGG  TGACGAAGGC  GAATCTGGAT  AAGATTCCCG  ACGATTACGA
1401  AAGAAAACAA  ACACTCGTCA  ATTCTGAAAG  ATTCATCACA  CCCGAATTGA
1451  AGGAGTTCGA  GACAAAGATA  ATGGCCGCTA  AAGAGAGAAT  AGAAGAACTG
1501  GAAAAGGAAC  TCTTCACAAG  CGTGTGCGAA  GAGGTGAAAA  AGCACAAAGA
1551  AGTTCTCCTT  GAGATCTCGG  AGGATCTGGC  AAAGATAGAT  GCGCTTTCGA
1601  CGTTAGCATA  CGACGCTATT  ATGTACAACT  ACACAAAACC  CGTCTTTTCA
1651  GAAGACAGAC  TGGAGATCAA  AGGTGGAAGA  CACCCGGTCG  TTGAAAGGTT
1701  CACACAGAAT  TTTGTTGAAA  ACGATATTTA  CATGGACAAC  GAGAAGAGAT
1751  TTGTGGTAAT  AACGGGTCCC  AACATGAGCG  GGAAGTCCAC  TTTCATCAGA
1801  CAGGTGGGTC  TCATATCCCT  CATGGCGCAG  ATAGGATCGT  TTGTGCCGGC
1851  GCAGAAGGCG  ATTCTTCCAG  TGTTCGACAG  GATTTTCACG  CGAATGGGTG
1901  CCAGAGACGA  TCTCGCTGGT  GGTAGAAGTA  CGTTCCTTGT  CGAGATGAAC
1951  GAGATGGCGC  TCATCCTTCT  GAAATCAACA  AATAAGAGTC  TGGTTCTCCT
2001  GGACGAGGTG  GGAAGAGGTA  CAAGCACCCA  GGACGGCGTC  AGCATAGCCT
2051  GGGCAATCTC  AGAGGAACTC  ATAAAGAGAG  GATGTAAGGT  GCTGTTTGCC
2101  ACTCATTTCA  CGGAACTCAC  GGAACTCGAA  AAACACTTTC  CGCAGGTTCA
2151  GAACAAAACC  ATTCTGGTAA  AAGAAGAAGG  CAAAAACGTG  ATATTCACCC
2201  ACAAGGTGGT  GGACGGTGTG  GCAGACAGAA  GTTACGGAAT  AGAGGTCGCA
2251  AAGATAGCGG  GTATTCCTGA  CAGGGTTATA  AACAGAGCCT  ATGAAATTCT
2301  GGAGAGGAAT  TTCAAAAACA  ACACGAAGAA  AAACGGAAAA  TCGAACAGAT
2351  TCAGTCAGCA  AATTCCTCTC  TTTCCTGTTT  GA
```

G + C CONTENT: 47%

FIGURE 3

```
  1  VKVTPLMEQY  LRIKEQYKDS  ILLFRLGDFY  EAFFEDAKIV  SKVLNIVLTR
 51  RQDAPMAGIP  YHALNTYLKK  LVEAGYKVAI  CDQMEEPSKS  KKLIRREVTR
101  VVTPGSIVED  EFLSETNNYM  AVVSEEKGRY  CTVFCDVSTG  EVLVHESSDE
151  QETLDLLKNY  SISQIICPEH  LKSSLKERFP  GVYTETISEW  YFSDLEEVEK
201  AYNLKDIHHF  ELSPLALKAL  AALIKYVKYT  MIGEDLNLKP  PLLISQRDYM
251  ILDSATVENL  SWIPGDRGKN  LFDVLNNTET  PMGARLGKKW  ILHPLVDRKQ
301  IEERLKAVER  LVNDRVSLEE  MRNLLSNVRD  VERIVSRVEY  NRSVPRDLVA
351  LRETLEIIPK  LNEVLSTFGV  FKKLAFPEGL  VDLLRKAIED  DPVGSPGEGK
401  VIKRGFSSEL  DEYRDLLEHA  EERLKEFEEK  ERERTGIQKL  RVGYNQVFGY
451  YIEVTKANLD  KIPDDYERKQ  TLVNSERFIT  PELKEFETKI  MAAKERIEEL
501  EKELFTSVCE  EVKKHKEVLL  EISEDLAKID  ALSTLAYDAI  MYNYTKPVFS
551  EDRLEIKGGR  HPVVERFTQN  FVENDIYMDN  EKRFVVITGP  NMSGKSTFIR
601  QVGLISLMAQ  IGSFVPAQKA  ILPVFDRIFT  RMGARDDLAG  GRSTFLVEMN
651  EMALILLKST  NKSLVLLDEV  GRGTSTQDGV  SIAWAISEEL  IKRGCKVLFA
701  THFTELTELE  KHFPQVQNKT  ILVKEEGKNV  IFTHKVVDGV  ADRSYGIEVA
751  KIAGIPDRVI  NRAYEILERN  FKNNTKKNGK  SNRFSQQIPL  FPV*
```

```
                10         20         30         40         50         60
Apycod   MGKEEKELTPMLAQYHQFKSMYPDCLLLFRLGDFYELFYEDAVVGSKELGLVLTSRPA
         |||::||  ::|:  :|:  ||::|:|||||||||:||   :|:  |::  ||:| |
Eco.Pe   MSAIENFDAHTPMMQQYLRLKAQHPEILLFYRMGDFYELFYDDAKRASQLLDISLTKRGA
           ||:|:|||||:|:|:  :  :|::|:||||| |::||| :|::|:|  ||:|
Tmacod       VKVTPLMEQYLRIKEQYKDSILLFRLGDFYEAFFEDAKIVSKVLNIVLTRR--

70         80         90        100        110        120
Apycod   GKGRERIPMCGVPYHSANNYIAKLVNKGYKVAICEQVEDPSKAKGIVKRDVIRVITPGTF
         :  |  |:|||  |:|||||:::||:|||||||  |:||||||||:  |  |:|::|||:
Eco.Pe   SAG-EPIPMAGIPYHAVENYLAKLVNQGESVAICEQIGDPATSKGPVERKVVRIVTPGTI
           :  |||||||||:::||  |||::|  :|||||:::|||: ||   |  |:|:|||:|
Tmacod   ----QDAPMAGIPYHALNTYLKKLVEAGYKVAICDQMEEPSKSKKLIRREVTRVVTPGSI 130        140        150        160        170        180
Apycod   F------ERETGGLCSLYRKGKSYLVSYLNLSVGEF-IGAKVKEEELIDFLSKFNIREVL
          ||:::  |  |::::::|::  :  |::| |  |::  ::  |::  |  :  |   |:|
Eco.Pe   SDEALLQERQDNLLAAIWQDSKGFGYATLDISSGRFRLSEPADRETMAAELQRTNPAELL
         ::::|  |  :|  :|::  :::  :  |:|:|  :  |::|   :  |::  :  ::::
Tmacod   VEDEFLSE-TNNYMAVVSEEKGRYCTVFCDVSTGEVLVHESSDEQETLDLLKNYSISQII 190        200        210        220        230        240
Apycod   VKKGEKLPEKLEKVLKLHITELEEEFFEEGKEELLKDYGVPSIKAFGFQDEDLSL-SLGA
          ::      :|     |:      |  |  :::::::|    ::|::::  :||  :::    :|  :  |
Eco.Pe   YAEDFAEMSLIEGRRGLRRRPLWEFEIDTARQQLNLQFGTRDLVGFGVENAPRGLCAAGC
         ::|::  :  ||   |  :|:    ::  |:  :: ::::  :::  :|:    |::  :|  :|||  :
Tmacod   CPEHLKS-SLKERFPGVYTETISEWYF-SDLEEVEKAYNLKDIHHFEL--SPLALKALAA 250        260        270        280        290        300
Apycod   VYRYAKATQKSFTPLIPKPKPYVDEGYVKLDLKAVKGLEITESIEGRKDLSLFKVVDRTL
         :  :|||:||::   |  |::  :  :::  :  :|    :  ::||||:::::|   :  |  :|:|  |:
Eco.Pe   LLQYAKDTQRTTLPHIRSITMEREQDSIIMDAATRRNLEITQNLAGGAENTLASVLDCTV
         |::|| |  ::  ::::  :  :::|  |  ::::|  :|:|:|||  ||:    ::|  :::|  :||: |
Tmacod   LIKYVKYTMIGEDLNLKPPLLISQRDYMILDSATVENLS---WIPGDRGKNLFDVLNNTE 310        320        330        340        350
Apycod   TGMGRRRLRFRLLNPFRSIERIRKVQEAVEELINKREVLNEIRKTLEGMSDLERLVSRIS
         |  |||:|:|: :|  |  | |  |::   :  |::::::|    ::  ::::  :|  ::|||:::|::
Eco.Pe   TPMGSRMLKRWLHMPVRDTRVLLERQQTIGAL---QDFTAGLQPVLRQVGDLERILARLA
         ||||:|  |:|:  |:  |  :  ||  ::::  |  |:|:  :|:||::  :|  :|||  |:||||::
Tmacod   TPMGARLGKKWILHPLVDRKQIEERLKAVERLVNDRVSLEEMRNLLSNVRDVERIVSRVE 360        370        380        390        400        410
Apycod   SNMASPRELIHLKNSLRKAEELRKILSLLDSEIFKEIEGSLLNLNKVADLIDKTLVDDPP
         :  |:||:|  :::::::::  |||  |:  :||:  :::  :::  :::::  ||:::::::|:||
Eco.Pe   LRTARPRDLARMRHAFQQLPELRAQLETVDSAPVQALREKMGEFAELRDLLERAIIDTPP
         :  :   ||||:  :|::::: :|:|::  |:|  ::  :  :|  |||  :||  |:|  |:|
Tmacod   YNRSVPRDLVALRETLEIIPKLNEVLSTF------GVFKKLAFPEGLVDLLRKAIEDDPV
```

FIGURE 5A

```
             420        430        440        450        460        470
Apycod   LHVKEGGLIKPGVNAYLDELRFIRENAEKLLKEYEKKLKKETGIQSLKIGYNKVMGYYIE
          :|::||:|  :|  |:  |||  |  :  ::|::  |:    |   :  ::  ||:::||:|  |  ||||:
Eco.Pe   VLVRDGGVIASGYNEELDEWRALADGATDYLERLEVRERERTGLDTLKVGFNAVHGYYIQ
          :|  ||  :|:::||||:|:|  :  |::  |:  :|  :|||||||:::|:||:|  ||||:
Tmacod   GSPGEGKVIKRGFSSELDEYRDLLEHAEERLKEFEEKERERTGIQKLRVGYNQVFGYYIE 480        490        500        510        520        530
Apycod   VTKANVKYVPEHFRRRQTLSNAERYTTEELQRLEEKILSAQTRINELEYELYRELREEVV
          :::::  :  :|  :::|||||:||||||::  ||:    |:|:|:::::    :||  :||  ||  :  ::
Eco.Pe   ISRGQSHLAPINYMRRQTLKNAERYIIPELKEYEDKVLTSKGKALALEKQLYEELFDLLL
          ::::: :    |  :| |:|||  |:|||:|||||:|||::::|::     :|||:|::::  :  :
Tmacod   VTKANLDKIPDDYERKQTLVNSERFITPELKEFETKIMAAKERIEELEKELFTSVCEEVK 540        550        560        570        580        590
Apycod   KELDKVGNNATLIGEVDYIQSLAWLALEKGWVKPEVHEGYELIIEEGKHPVIEE-FTKNY
          :|:  :  ::|:  ::|:|  :  :||    |  :::  |:    ::  |:|||:|||:|:  ::: :
Eco.Pe   PHLEALQQSASALAELDVLVNLAERAYTLNYTCPTFIDKPGIRITEGRHPVVEQVLNEPF
          |  |:|  :  :::||::|:|  :||  |    |||  |  |::|||||||  :::||||||||  :::  |
Tmacod   KHKEVLLEISEDLAKIDALSTLAYDAIMYNYTKPVFSEDR-LEIKGGRHPVVER-FTQNF 600        610        620        630        640        650
Apycod   VPNDTKLTEEEFIHVITGPNMAGKSSYIRQVGVLTLLAHTGSFLPVKSARIPLVDAIFTR
          ::|    :|:  :    :  :|||||||:|||:|:|::::::|:::||::||::::    |  :|  ||||
Eco.Pe   IANPLNLSPQRRMLIITGPNMGGKSTYMRQTALIALMAYIGSYVPAQKVEIGPIDRIFTR
          ::|    :  ::  ::|:::||||||:||||::||::||:|||  |||  ||:||||||  :|||||
Tmacod   VENDIYMDNEKRFVVITGPNMSGKSTFIRQVGLISLMAQIGSFVPAQKAILPVFDRIFTR 660        670        680        690        700        710
Apycod   IGSGDVLALGVSTFMNEMLDVSNILNNATKRSLIILDEVGRGTSTYDGIAISKAIVKYIS
          :|::|  ||  |  ||||  ||  :::|||:|||:  ||:::||:|||||||||||::::  |  ::  ::
Eco.Pe   VGAADDLASGRSTFMVEMTETANILHNATEYSLVLMDEIGRGTSTYDGLSLAWACAENLA
          :||  ||||:|||||:|||:|  |  ||  ::|:  ||||:||:||||||  ||:|:|||  :|:|
Tmacod   KGARDDLAGGRSTFLVEMNEMALILLKSTNKSLVLLDEVGRGTSTQDGVSIAWAISEELI 720        730        740        750        760        770
Apycod   EKIGAKTLLATHYLELTELERKVKGVKNYHMEVEETDEGIRFLYILKEGRAKGSFGIDVA
          :||  |  ||:|||||:|||:|  |::||  |  |:::  |  :::|  |::  :|  :::|  |:  |:|::||
Eco.Pe   NKIKALTLFATHYFELTQLPEKMEGVANVHLDALEHGDTIAFMHSVQDGAASKSYGLAVA
          ::    :||||:|  |||:|  |||:|  :::  |:|  :  :  |  |:|:::  |  |:|  ||:|::|||::||
Tmacod   KR-GCKVLFATHFTELTELEKHFPQVQNKTILVKEEGKNVIFTHKVVDGVADRSYGIEVA 780        790        800        810        820        830
Apycod   KLAGLPEEVVREAKKIL-KELEGEKGKQEVLPFLEETYKK-SVDEEKLNFYEEIIKEIEE
          |||:|||::  |::  |  :|||  |    ||||  ::  ::  ||  |||    :  :::|:
Eco.Pe   ALAGVPKEVIKRARQKL-RELESISPNAAATQVDGTQMSLLSVPEET----SPAVEALEN
          :||:|  ||:||  |    |  |:::  :  :::    |  |::|::|
Tmacod   KIAGIPDRVINRAYEILERNFKNNTKKNGKSNRFSQQIPLFPV*

840        850
Apy.Pe   IDIGNTTPVKALLILAELKERIKSFIKR*
          :|  ::  ||  :  ||  :  ||:  :
Eco.Se   LDPDSLTPRQALEWIYRLKSLV*
```

FIGURE 5B

Tma MutS PROTEIN INITIATION & TERMINATION

INITIATION:

End of orf:
R  E  F  Y  E  R  L  G  Y  R  A  E  G  E  I  F  Y  E  R  T  F  H  T  *

Initiation of Tma MutS:
\*  E  S  S  T  R  D  S  V  T  G  Q  K  E  R  S  S  T  N  E  H  S  T  R  E  D  G  E  G  G  E  T  V  K  V  T

5' Sequence:
TGAGAGAGTTCTACGAGACTCGGTTACAGGGCAGAAGGAGATCTTCTACGAACGAACATTCCACACGTGAGGATGGTGAAGGTGGTGAAACCGTGAAGGTAAC

3' end of 16S ribosomal RNA:
ucuUUCCuCCACU

TERMINATION:

Antisense orf:
\*  D  A  F  E  E  R  E  Q  K  I  S  K  I  L  E  V  Y  N  D  N  R  F

Termination of Tma MutS:
K  N  N  T  K  K  N  G  K  S  N  R  F  S  Q  Q  I  P  L  F  P  V  *

3' Sequence:
AAAAACAACACGAAGAAAAACGAAGAAAATCGAACAGATTCAGTCAGCAAATTCCTCCTCTTTCCTGTTTGATGCTCTTATCAGTTCAACGTAATTGTCGTTTCTGAA

Antisense orf identification:

```
Sma.dod   KLRQVRKLIDDSGRDIRLEVDGGVKVDNIAEIAAAGADMFVAGSAIFGQPDYRK*
          |:|:||:|:||  |:|  ||||||   ||: :|:|||:: :| ||  |:|:|:
Anti.tma  KIRNLRKMVKELGLETEIMVDGGVNEENASILVKNGATILVMGYGIFRNDNYVELIKSIKQEREEFAD*
          ::  :|:|:||:  :  ||  ||:|||| |||||||  ||::|| :||:|| |:  |
Aeu.epi   ARARIDRQVDAGGRPVWLEIDGGVKADNIAAIARAGADTFVAGSAVFGAPDADGGYSSILYRLREAATVT*
```

D-ribulose-5-phosphate 3-epimerase – *Alcaligenes eutrophus*; dod – *Serratia marcescens*

FIGURE 6

```
  1 AAGTCCACCT TCCTCCGCCG GACCGCCCTC ATCGCCCTCC TCGCCCAGAT
 51 CGGGAGCTTC GCGCCCGCCG AGGGGCTGCT GCTTCCCCTC TTTGACGGGA
101 TC
```

FIGURE 7

```
  1 AAGTCCACCT TTCTGCGCCA GACGGCCCTC ATCGCCCTCC TGGCCCAGGT
 51 GGGGAGCTTC GTGCCCGCCG AGGAGGCCCA TCTTCCCCTC TTTGACGGCA
101 TC
```

FIGURE 8

```
        613
    Apy KSSYIRQVG VLTLLAHTGS FLPVKSARIP LVDAI
    Taq KSTFLRQTA LIALLAQVGS FVPAEEAHLP LFDGI
    Tth KSTFLRRTA LIALLAQIGS FAPAEGLLLP LFDGI
    Tma KSTFIRQVG LISLMAQIGS FVPAQKAILP VFDRI
        595
```

FIGURE 9

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 2568 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2565

( x i ) SEQUENCE DESCRIPTION: SEQ ID NO:1:

```
ATG  GGA  AAA  GAG  GAG  AAA  GAG  CTC  ACC  CCC  ATG  CTC  GCC  CAG  TAT  CAC        48
Met  Gly  Lys  Glu  Glu  Lys  Glu  Leu  Thr  Pro  Met  Leu  Ala  Gln  Tyr  His
 1                    5                         10                        15

CAG  TTC  AAG  AGC  ATG  TAT  CCC  GAC  TGC  CTT  CTT  TTA  TTC  AGG  CTC  GGG        96
Gln  Phe  Lys  Ser  Met  Tyr  Pro  Asp  Cys  Leu  Leu  Leu  Phe  Arg  Leu  Gly
                     20                        25                   30

GAC  TTT  TAC  GAG  CTC  TTT  TAC  GAG  GAC  GCG  GTC  GTC  GGT  TCT  AAA  GAG       144
Asp  Phe  Tyr  Glu  Leu  Phe  Tyr  Glu  Asp  Ala  Val  Val  Gly  Ser  Lys  Glu
               35                        40                   45

CTC  GGT  CTA  GTT  CTA  ACT  TCA  AGA  CCC  GCG  GGA  AAG  GGA  AGG  GAA  AGG       192
Leu  Gly  Leu  Val  Leu  Thr  Ser  Arg  Pro  Ala  Gly  Lys  Gly  Arg  Glu  Arg
          50                        55                   60

ATT  CCC  ATG  TGC  GGT  GTT  CCC  TAC  CAT  TCT  GCA  AAC  AAC  TAT  ATA  GCA       240
Ile  Pro  Met  Cys  Gly  Val  Pro  Tyr  His  Ser  Ala  Asn  Asn  Tyr  Ile  Ala
 65                       70                   75                        80

AAG  CTC  GTT  AAT  AAG  GGA  TAC  AAG  GTA  GCA  ATA  TGC  GAG  CAG  GTT  GAG       288
Lys  Leu  Val  Asn  Lys  Gly  Tyr  Lys  Val  Ala  Ile  Cys  Glu  Gln  Val  Glu
```

|  |  |  |  |  |  |  |  |  |  |  |  |  |  |  |  |
|---|---|---|---|---|---|---|---|---|---|---|---|---|---|---|---|
|  |  |  |  | 85 |  |  |  |  | 90 |  |  |  |  | 95 |  |
| GAC | CCC | TCA | AAG | GCA | AAG | GGA | ATA | GTA | AAG | AGG | GAC | GTA | ATA | AGA | GTT | 336
| Asp | Pro | Ser | Lys | Ala | Lys | Gly | Ile | Val | Lys | Arg | Asp | Val | Ile | Arg | Val |
|  |  |  | 100 |  |  |  | 105 |  |  |  |  | 110 |  |  |  |
| ATA | ACA | CCT | GGG | ACC | TTT | TTT | GAG | AGG | GAA | ACG | GGA | GGG | CTT | TGC | TCC | 384
| Ile | Thr | Pro | Gly | Thr | Phe | Phe | Glu | Arg | Glu | Thr | Gly | Gly | Leu | Cys | Ser |
|  |  | 115 |  |  |  |  | 120 |  |  |  |  | 125 |  |  |  |
| CTT | TAC | AGG | AAG | GGA | AAG | AGC | TAT | CTC | GTT | TCT | TAT | CTT | AAC | CTC | TCG | 432
| Leu | Tyr | Arg | Lys | Gly | Lys | Ser | Tyr | Leu | Val | Ser | Tyr | Leu | Asn | Leu | Ser |
|  | 130 |  |  |  |  | 135 |  |  |  |  | 140 |  |  |  |  |
| GTA | GGT | GAG | TTC | ATA | GGT | GCA | AAG | GTA | AAG | GAG | GAA | GAG | CTC | ATA | GAC | 480
| Val | Gly | Glu | Phe | Ile | Gly | Ala | Lys | Val | Lys | Glu | Glu | Glu | Leu | Ile | Asp |
| 145 |  |  |  |  | 150 |  |  |  |  | 155 |  |  |  |  | 160 |
| TTC | CTC | TCA | AAG | TTC | AAC | ATA | AGG | GAG | GTT | CTT | GTA | AAG | AAG | GGA | GAA | 528
| Phe | Leu | Ser | Lys | Phe | Asn | Ile | Arg | Glu | Val | Leu | Val | Lys | Lys | Gly | Glu |
|  |  |  |  | 165 |  |  |  |  | 170 |  |  |  |  | 175 |  |
| AAG | CTC | CCC | GAA | AAG | CTT | GAG | AAG | GTT | CTA | AAG | CTC | CAC | ATA | ACG | GAG | 576
| Lys | Leu | Pro | Glu | Lys | Leu | Glu | Lys | Val | Leu | Lys | Leu | His | Ile | Thr | Glu |
|  |  |  | 180 |  |  |  |  | 185 |  |  |  |  | 190 |  |  |
| CTT | GAA | GAG | GAG | TTC | TTT | GAG | GAG | GGA | AAG | GAG | GAG | CTT | CTT | AAG | GAT | 624
| Leu | Glu | Glu | Glu | Phe | Phe | Glu | Glu | Gly | Lys | Glu | Glu | Leu | Leu | Lys | Asp |
|  |  | 195 |  |  |  |  | 200 |  |  |  |  | 205 |  |  |  |
| TAC | GGA | GTT | CCG | TCG | ATA | AAA | GCC | TTC | GGC | TTT | CAG | GAT | GAG | GAT | TTA | 672
| Tyr | Gly | Val | Pro | Ser | Ile | Lys | Ala | Phe | Gly | Phe | Gln | Asp | Glu | Asp | Leu |
|  | 210 |  |  |  |  | 215 |  |  |  |  | 220 |  |  |  |  |
| TCC | CTT | TCC | CTC | GGG | GCT | GTT | TAC | AGG | TAT | GCA | AAG | GCG | ACA | CAG | AAA | 720
| Ser | Leu | Ser | Leu | Gly | Ala | Val | Tyr | Arg | Tyr | Ala | Lys | Ala | Thr | Gln | Lys |
| 225 |  |  |  |  | 230 |  |  |  |  | 235 |  |  |  |  | 240 |
| TCT | TTT | ACC | CCT | CTC | ATT | CCA | AAG | CCC | AAA | CCT | TAC | GTT | GAC | GAG | GGA | 768
| Ser | Phe | Thr | Pro | Leu | Ile | Pro | Lys | Pro | Lys | Pro | Tyr | Val | Asp | Glu | Gly |
|  |  |  |  | 245 |  |  |  |  | 250 |  |  |  |  | 255 |  |
| TAC | GTA | AAG | CTT | GAC | CTC | AAG | GCA | GTC | AAA | GGT | CTT | GAG | ATT | ACC | GAA | 816
| Tyr | Val | Lys | Leu | Asp | Leu | Lys | Ala | Val | Lys | Gly | Leu | Glu | Ile | Thr | Glu |
|  |  |  | 260 |  |  |  |  | 265 |  |  |  |  | 270 |  |  |
| AGC | ATA | GAA | GGA | AGA | AAG | GAT | TTA | TCC | CTG | TTT | AAG | GTC | GTT | GAC | AGA | 864
| Ser | Ile | Glu | Gly | Arg | Lys | Asp | Leu | Ser | Leu | Phe | Lys | Val | Val | Asp | Arg |
|  |  | 275 |  |  |  |  | 280 |  |  |  |  | 285 |  |  |  |
| ACC | CTC | ACG | GGT | ATG | GGG | AGA | AGG | AGG | CTG | AGG | TTC | AGG | CTT | CTA | AAC | 912
| Thr | Leu | Thr | Gly | Met | Gly | Arg | Arg | Arg | Leu | Arg | Phe | Arg | Leu | Leu | Asn |
|  | 290 |  |  |  |  | 295 |  |  |  |  | 300 |  |  |  |  |
| CCC | TTC | AGG | AGC | ATA | GAG | AGA | ATA | AGG | AAG | GTT | CAG | GAA | GCA | GTT | GAG | 960
| Pro | Phe | Arg | Ser | Ile | Glu | Arg | Ile | Arg | Lys | Val | Gln | Glu | Ala | Val | Glu |
| 305 |  |  |  |  | 310 |  |  |  |  | 315 |  |  |  |  | 320 |
| GAG | CTA | ATA | AAC | AAG | AGG | GAG | GTT | CTG | AAC | GAG | ATA | AGG | AAA | ACC | CTT | 1008
| Glu | Leu | Ile | Asn | Lys | Arg | Glu | Val | Leu | Asn | Glu | Ile | Arg | Lys | Thr | Leu |
|  |  |  |  | 325 |  |  |  |  | 330 |  |  |  |  | 335 |  |
| GAG | GGT | ATG | TCC | GAC | CTT | GAG | AGA | CTC | GTA | TCC | AGG | ATA | AGC | TCA | AAC | 1056
| Glu | Gly | Met | Ser | Asp | Leu | Glu | Arg | Leu | Val | Ser | Arg | Ile | Ser | Ser | Asn |
|  |  |  | 340 |  |  |  |  | 345 |  |  |  |  | 350 |  |  |
| ATG | GCA | AGC | CCA | AGA | GAA | CTT | ATA | CAC | CTC | AAA | AAC | TCC | CTA | AGG | AAG | 1104
| Met | Ala | Ser | Pro | Arg | Glu | Leu | Ile | His | Leu | Lys | Asn | Ser | Leu | Arg | Lys |
|  |  | 355 |  |  |  |  | 360 |  |  |  |  | 365 |  |  |  |
| GCG | GAG | GAG | CTA | AGG | AAA | ATT | TTA | TCT | TTG | CTT | GAT | TCC | GAA | ATA | TTT | 1152
| Ala | Glu | Glu | Leu | Arg | Lys | Ile | Leu | Ser | Leu | Leu | Asp | Ser | Glu | Ile | Phe |
|  | 370 |  |  |  |  | 375 |  |  |  |  | 380 |  |  |  |  |
| AAA | GAG | ATA | GAA | GGT | TCT | CTC | CTT | AAC | CTG | AAT | AAA | GTT | GCG | GAC | CTC | 1200
| Lys | Glu | Ile | Glu | Gly | Ser | Leu | Leu | Asn | Leu | Asn | Lys | Val | Ala | Asp | Leu |
| 385 |  |  |  |  | 390 |  |  |  |  | 395 |  |  |  |  | 400 |
| ATT | GAT | AAA | ACG | CTT | GTT | GAC | GAC | CCT | CCC | CTG | CAC | GTA | AAA | GAA | GGG | 1248
| Ile | Asp | Lys | Thr | Leu | Val | Asp | Asp | Pro | Pro | Leu | His | Val | Lys | Glu | Gly |

|     |     |     |     |     | 405 |     |     |     | 410 |     |     |     |     | 415 |     |      |
|-----|-----|-----|-----|-----|-----|-----|-----|-----|-----|-----|-----|-----|-----|-----|-----|------|

```
GGG  CTT  ATA  AAA  CCC  GGT  GTT  AAC  GCA  TAC  CTT  GAT  GAG  CTT  CGC  TTC      1296
Gly  Leu  Ile  Lys  Pro  Gly  Val  Asn  Ala  Tyr  Leu  Asp  Glu  Leu  Arg  Phe
               420                 425                      430

ATA  AGG  GAG  AAT  GCG  GAA  AAG  CTC  CTG  AAG  GAG  TAT  GAA  AAG  AAG  CTG      1344
Ile  Arg  Glu  Asn  Ala  Glu  Lys  Leu  Leu  Lys  Glu  Tyr  Glu  Lys  Lys  Leu
          435                      440                      445

AAA  AAA  GAA  ACG  GGA  ATT  CAG  AGC  TTA  AAG  ATT  GGA  TAC  AAC  AAG  GTT      1392
Lys  Lys  Glu  Thr  Gly  Ile  Gln  Ser  Leu  Lys  Ile  Gly  Tyr  Asn  Lys  Val
     450                      455                      460

ATG  GGA  TAC  TAC  ATA  GAG  GTA  ACG  AAG  GCT  AAC  GTA  AAA  TAC  GTT  CCC      1440
Met  Gly  Tyr  Tyr  Ile  Glu  Val  Thr  Lys  Ala  Asn  Val  Lys  Tyr  Val  Pro
465                 470                      475                      480

GAA  CAC  TTC  AGA  AGA  AGA  CAG  ACC  CTT  TCA  AAC  GCG  GAG  AGA  TAC  ACA      1488
Glu  His  Phe  Arg  Arg  Arg  Gln  Thr  Leu  Ser  Asn  Ala  Glu  Arg  Tyr  Thr
                    485                      490                      495

ACC  GAG  GAG  CTC  CAG  AGA  CTT  GAG  GAA  AAG  ATA  CTT  TCC  GCC  CAG  ACC      1536
Thr  Glu  Glu  Leu  Gln  Arg  Leu  Glu  Glu  Lys  Ile  Leu  Ser  Ala  Gln  Thr
               500                      505                      510

CGC  ATA  AAC  GAG  CTT  GAG  TAT  GAG  CTT  TAC  AGG  GAG  CTC  AGG  GAA  GAG      1584
Arg  Ile  Asn  Glu  Leu  Glu  Tyr  Glu  Leu  Tyr  Arg  Glu  Leu  Arg  Glu  Glu
               515                      520                      525

GTT  GTT  AAG  GAG  CTT  GAT  AAG  GTA  GGG  AAT  AAC  GCA  ACC  CTC  ATA  GGG      1632
Val  Val  Lys  Glu  Leu  Asp  Lys  Val  Gly  Asn  Asn  Ala  Thr  Leu  Ile  Gly
          530                      535                      540

GAG  GTG  GAC  TAC  ATC  CAG  TCC  CTC  GCC  TGG  CTT  GCC  CTT  GAG  AAG  GGA      1680
Glu  Val  Asp  Tyr  Ile  Gln  Ser  Leu  Ala  Trp  Leu  Ala  Leu  Glu  Lys  Gly
545                      550                      555                      560

TGG  GTA  AAG  CCG  GAA  GTT  CAC  GAG  GGA  TAT  GAG  CTG  ATA  ATA  GAG  GAG      1728
Trp  Val  Lys  Pro  Glu  Val  His  Glu  Gly  Tyr  Glu  Leu  Ile  Ile  Glu  Glu
                    565                      570                      575

GGA  AAG  CAT  CCC  GTA  ATA  GAG  GAG  TTC  ACG  AAA  AAC  TAC  GTC  CCA  AAC      1776
Gly  Lys  His  Pro  Val  Ile  Glu  Glu  Phe  Thr  Lys  Asn  Tyr  Val  Pro  Asn
               580                      585                      590

GAT  ACG  AAG  CTA  ACG  GAA  GAG  GAG  TTC  ATA  CAC  GTA  ATC  ACG  GGC  CCT      1824
Asp  Thr  Lys  Leu  Thr  Glu  Glu  Glu  Phe  Ile  His  Val  Ile  Thr  Gly  Pro
          595                      600                      605

AAC  ATG  GCG  GGA  AAG  TCG  AGC  TAC  ATA  AGA  CAG  GTG  GGC  GTC  CTC  ACG      1872
Asn  Met  Ala  Gly  Lys  Ser  Ser  Tyr  Ile  Arg  Gln  Val  Gly  Val  Leu  Thr
     610                      615                      620

CTC  CTT  GCT  CAT  ACA  GGT  AGC  TTC  CTT  CCC  GTA  AAG  AGT  GCA  AGG  ATA      1920
Leu  Leu  Ala  His  Thr  Gly  Ser  Phe  Leu  Pro  Val  Lys  Ser  Ala  Arg  Ile
625                      630                      635                      640

CCG  CTG  GTT  GAT  GCG  ATA  TTC  ACG  AGA  ATA  GGC  TCG  GGG  GAC  GTT  CTG      1968
Pro  Leu  Val  Asp  Ala  Ile  Phe  Thr  Arg  Ile  Gly  Ser  Gly  Asp  Val  Leu
                    645                      650                      655

GCT  CTG  GGT  GTT  TCA  ACC  TTC  ATG  AAC  GAG  ATG  CTT  GAC  GTG  TCA  AAC      2016
Ala  Leu  Gly  Val  Ser  Thr  Phe  Met  Asn  Glu  Met  Leu  Asp  Val  Ser  Asn
               660                      665                      670

ATA  CTC  AAC  AAC  GCA  ACG  AAG  AGG  AGC  TTA  ATA  ATA  CTC  GAC  GAG  GTG      2064
Ile  Leu  Asn  Asn  Ala  Thr  Lys  Arg  Ser  Leu  Ile  Ile  Leu  Asp  Glu  Val
               675                      680                      685

GGA  AGG  GGA  ACC  TCA  ACC  TAC  GAC  GGG  ATA  GCG  ATA  AGC  AAG  GCG  ATA      2112
Gly  Arg  Gly  Thr  Ser  Thr  Tyr  Asp  Gly  Ile  Ala  Ile  Ser  Lys  Ala  Ile
     690                      695                      700

GTG  AAA  TAC  ATA  AGC  GAG  AAG  ATA  GGG  GCG  AAA  ACG  CTA  CTC  GCA  ACC      2160
Val  Lys  Tyr  Ile  Ser  Glu  Lys  Ile  Gly  Ala  Lys  Thr  Leu  Leu  Ala  Thr
705                      710                      715                      720

CAC  TAC  CTT  GAG  CTA  ACC  GAG  CTT  GAG  AGA  AAG  GTA  AAG  GGA  GTA  AAG      2208
His  Tyr  Leu  Glu  Leu  Thr  Glu  Leu  Glu  Arg  Lys  Val  Lys  Gly  Val  Lys
```

|     |     |     |     |     | 725 |     |     |     |     | 730 |     |     |     |     | 735 |     |     |
|-----|-----|-----|-----|-----|-----|-----|-----|-----|-----|-----|-----|-----|-----|-----|-----|-----|-----|

```
AAC  TAC  CAC  ATG  GAG  GTT  GAG  GAA  ACG  GAT  GAG  GGA  ATA  AGG  TTC  TTA        2256
Asn  Tyr  His  Met  Glu  Val  Glu  Glu  Thr  Asp  Glu  Gly  Ile  Arg  Phe  Leu
               740                      745                      750

TAC  ATA  CTG  AAG  GAG  GGA  AGG  GCG  AAG  GGA  AGC  TTC  GGC  ATA  GAC  GTC        2304
Tyr  Ile  Leu  Lys  Glu  Gly  Arg  Ala  Lys  Gly  Ser  Phe  Gly  Ile  Asp  Val
          755                      760                      765

GCA  AAA  CTC  GCG  GGA  CTG  CCC  GAG  GAA  GTT  GTA  AGG  GAA  GCA  AAA  AAG        2352
Ala  Lys  Leu  Ala  Gly  Leu  Pro  Glu  Glu  Val  Val  Arg  Glu  Ala  Lys  Lys
     770                      775                      780

ATA  CTG  AAG  GAG  CTT  GAA  GGG  GAA  AAA  GGA  AAG  CAG  GAA  GTT  CTC  CCC        2400
Ile  Leu  Lys  Glu  Leu  Glu  Gly  Glu  Lys  Gly  Lys  Gln  Glu  Val  Leu  Pro
785                      790                      795                      800

TTC  CTT  GAG  GAG  ACC  TAT  AAA  AAG  TCC  GTT  GAT  GAA  GAG  AAG  CTG  AAC        2448
Phe  Leu  Glu  Glu  Thr  Tyr  Lys  Lys  Ser  Val  Asp  Glu  Glu  Lys  Leu  Asn
                    805                      810                      815

TTT  TAC  GAA  GAG  ATA  ATA  AAG  GAG  ATA  GAG  GAG  ATA  GAT  ATA  GGG  AAC        2496
Phe  Tyr  Glu  Glu  Ile  Ile  Lys  Glu  Ile  Glu  Glu  Ile  Asp  Ile  Gly  Asn
               820                      825                      830

ACG  ACT  CCT  GTT  AAA  GCC  CTG  CTC  ATC  CTT  GCG  GAG  TTA  AAG  GAA  AGG        2544
Thr  Thr  Pro  Val  Lys  Ala  Leu  Leu  Ile  Leu  Ala  Glu  Leu  Lys  Glu  Arg
          835                      840                      845

ATA  AAG  AGC  TTT  ATA  AAG  AGG  TGA                                                 2568
Ile  Lys  Ser  Phe  Ile  Lys  Arg
850                      855
```

(2) INFORMATION FOR SEQ ID NO:2:

(i) SEQUENCE CHARACTERISTICS:
        (A) LENGTH: 855 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Gly  Lys  Glu  Glu  Lys  Glu  Leu  Thr  Pro  Met  Leu  Ala  Gln  Tyr  His
 1                  5                        10                      15

Gln  Phe  Lys  Ser  Met  Tyr  Pro  Asp  Cys  Leu  Leu  Leu  Phe  Arg  Leu  Gly
               20                      25                      30

Asp  Phe  Tyr  Glu  Leu  Phe  Tyr  Glu  Asp  Ala  Val  Val  Gly  Ser  Lys  Glu
          35                      40                      45

Leu  Gly  Leu  Val  Leu  Thr  Ser  Arg  Pro  Ala  Gly  Lys  Gly  Arg  Glu  Arg
     50                      55                      60

Ile  Pro  Met  Cys  Gly  Val  Pro  Tyr  His  Ser  Ala  Asn  Asn  Tyr  Ile  Ala
65                       70                      75                       80

Lys  Leu  Val  Asn  Lys  Gly  Tyr  Lys  Val  Ala  Ile  Cys  Glu  Gln  Val  Glu
                    85                      90                      95

Asp  Pro  Ser  Lys  Ala  Lys  Gly  Ile  Val  Lys  Arg  Asp  Val  Ile  Arg  Val
               100                     105                     110

Ile  Thr  Pro  Gly  Thr  Phe  Phe  Glu  Arg  Glu  Thr  Gly  Gly  Leu  Cys  Ser
          115                     120                     125

Leu  Tyr  Arg  Lys  Gly  Lys  Ser  Tyr  Leu  Val  Ser  Tyr  Leu  Asn  Leu  Ser
     130                     135                     140

Val  Gly  Glu  Phe  Ile  Gly  Ala  Lys  Val  Lys  Glu  Glu  Leu  Ile  Asp
145                     150                     155                     160

Phe  Leu  Ser  Lys  Phe  Asn  Ile  Arg  Glu  Val  Leu  Val  Lys  Lys  Gly  Glu
                    165                     170                     175

Lys  Leu  Pro  Glu  Lys  Leu  Glu  Lys  Val  Leu  Lys  Leu  His  Ile  Thr  Glu
```

-continued

```
                        180                           185                            190
Leu  Glu  Glu  Glu  Phe  Phe  Glu  Glu  Gly  Lys  Glu  Glu  Leu  Leu  Lys  Asp
          195                      200                      205

Tyr  Gly  Val  Pro  Ser  Ile  Lys  Ala  Phe  Gly  Phe  Gln  Asp  Glu  Asp  Leu
          210                      215                      220

Ser  Leu  Ser  Leu  Gly  Ala  Val  Tyr  Arg  Tyr  Ala  Lys  Ala  Thr  Gln  Lys
225                      230                      235                      240

Ser  Phe  Thr  Pro  Leu  Ile  Pro  Lys  Pro  Lys  Pro  Tyr  Val  Asp  Glu  Gly
                    245                      250                      255

Tyr  Val  Lys  Leu  Asp  Leu  Lys  Ala  Val  Lys  Gly  Leu  Glu  Ile  Thr  Glu
               260                      265                      270

Ser  Ile  Glu  Gly  Arg  Lys  Asp  Leu  Ser  Leu  Phe  Lys  Val  Val  Asp  Arg
          275                      280                      285

Thr  Leu  Thr  Gly  Met  Gly  Arg  Arg  Arg  Leu  Arg  Phe  Arg  Leu  Leu  Asn
          290                      295                      300

Pro  Phe  Arg  Ser  Ile  Glu  Arg  Ile  Arg  Lys  Val  Gln  Glu  Ala  Val  Glu
305                      310                      315                      320

Glu  Leu  Ile  Asn  Lys  Arg  Glu  Val  Leu  Asn  Glu  Ile  Arg  Lys  Thr  Leu
                    325                      330                      335

Glu  Gly  Met  Ser  Asp  Leu  Glu  Arg  Leu  Val  Ser  Arg  Ile  Ser  Ser  Asn
                340                      345                      350

Met  Ala  Ser  Pro  Arg  Glu  Leu  Ile  His  Leu  Lys  Asn  Ser  Leu  Arg  Lys
          355                      360                      365

Ala  Glu  Glu  Leu  Arg  Lys  Ile  Leu  Ser  Leu  Leu  Asp  Ser  Glu  Ile  Phe
          370                      375                      380

Lys  Glu  Ile  Glu  Gly  Ser  Leu  Leu  Asn  Leu  Asn  Lys  Val  Ala  Asp  Leu
385                      390                      395                      400

Ile  Asp  Lys  Thr  Leu  Val  Asp  Asp  Pro  Pro  Leu  His  Val  Lys  Glu  Gly
                    405                      410                      415

Gly  Leu  Ile  Lys  Pro  Gly  Val  Asn  Ala  Tyr  Leu  Asp  Glu  Leu  Arg  Phe
               420                      425                      430

Ile  Arg  Glu  Asn  Ala  Glu  Lys  Leu  Leu  Lys  Glu  Tyr  Glu  Lys  Lys  Leu
          435                      440                      445

Lys  Lys  Glu  Thr  Gly  Ile  Gln  Ser  Leu  Lys  Ile  Gly  Tyr  Asn  Lys  Val
450                      455                      460

Met  Gly  Tyr  Tyr  Ile  Glu  Val  Thr  Lys  Ala  Asn  Val  Lys  Tyr  Val  Pro
465                      470                      475                      480

Glu  His  Phe  Arg  Arg  Arg  Gln  Thr  Leu  Ser  Asn  Ala  Glu  Arg  Tyr  Thr
                    485                      490                      495

Thr  Glu  Glu  Leu  Gln  Arg  Leu  Glu  Glu  Lys  Ile  Leu  Ser  Ala  Gln  Thr
               500                      505                      510

Arg  Ile  Asn  Glu  Leu  Glu  Tyr  Glu  Leu  Tyr  Arg  Glu  Leu  Arg  Glu  Glu
          515                      520                      525

Val  Val  Lys  Glu  Leu  Asp  Lys  Val  Gly  Asn  Asn  Ala  Thr  Leu  Ile  Gly
          530                      535                      540

Glu  Val  Asp  Tyr  Ile  Gln  Ser  Leu  Ala  Trp  Leu  Ala  Leu  Glu  Lys  Gly
545                      550                      555                      560

Trp  Val  Lys  Pro  Glu  Val  His  Glu  Gly  Tyr  Glu  Leu  Ile  Ile  Glu  Glu
                    565                      570                      575

Gly  Lys  His  Pro  Val  Ile  Glu  Glu  Phe  Thr  Lys  Asn  Tyr  Val  Pro  Asn
               580                      585                      590

Asp  Thr  Lys  Leu  Thr  Glu  Glu  Glu  Phe  Ile  His  Val  Ile  Thr  Gly  Pro
          595                      600                      605
```

| Asn | Met | Ala | Gly | Lys | Ser | Ser | Tyr | Ile | Arg | Gln | Val | Gly | Val | Leu | Thr |
|-----|-----|-----|-----|-----|-----|-----|-----|-----|-----|-----|-----|-----|-----|-----|-----|
| 610 |     |     |     |     | 615 |     |     |     |     | 620 |     |     |     |     |     |
| Leu | Leu | Ala | His | Thr | Gly | Ser | Phe | Leu | Pro | Val | Lys | Ser | Ala | Arg | Ile |
| 625 |     |     |     |     | 630 |     |     |     |     | 635 |     |     |     |     | 640 |
| Pro | Leu | Val | Asp | Ala | Ile | Phe | Thr | Arg | Ile | Gly | Ser | Gly | Asp | Val | Leu |
|     |     |     |     | 645 |     |     |     |     | 650 |     |     |     |     | 655 |     |
| Ala | Leu | Gly | Val | Ser | Thr | Phe | Met | Asn | Glu | Met | Leu | Asp | Val | Ser | Asn |
|     |     |     |     | 660 |     |     |     |     | 665 |     |     |     |     | 670 |     |
| Ile | Leu | Asn | Asn | Ala | Thr | Lys | Arg | Ser | Leu | Ile | Ile | Leu | Asp | Glu | Val |
|     |     |     | 675 |     |     |     |     | 680 |     |     |     |     | 685 |     |     |
| Gly | Arg | Gly | Thr | Ser | Thr | Tyr | Asp | Gly | Ile | Ala | Ile | Ser | Lys | Ala | Ile |
|     |     | 690 |     |     |     |     | 695 |     |     |     |     | 700 |     |     |     |
| Val | Lys | Tyr | Ile | Ser | Glu | Lys | Ile | Gly | Ala | Lys | Thr | Leu | Leu | Ala | Thr |
| 705 |     |     |     |     | 710 |     |     |     |     | 715 |     |     |     |     | 720 |
| His | Tyr | Leu | Glu | Leu | Thr | Glu | Leu | Glu | Arg | Lys | Val | Lys | Gly | Val | Lys |
|     |     |     |     | 725 |     |     |     |     | 730 |     |     |     |     | 735 |     |
| Asn | Tyr | His | Met | Glu | Val | Glu | Glu | Thr | Asp | Glu | Gly | Ile | Arg | Phe | Leu |
|     |     |     | 740 |     |     |     |     | 745 |     |     |     |     | 750 |     |     |
| Tyr | Ile | Leu | Lys | Glu | Gly | Arg | Ala | Lys | Gly | Ser | Phe | Gly | Ile | Asp | Val |
|     |     | 755 |     |     |     |     | 760 |     |     |     |     | 765 |     |     |     |
| Ala | Lys | Leu | Ala | Gly | Leu | Pro | Glu | Glu | Val | Val | Arg | Glu | Ala | Lys | Lys |
| 770 |     |     |     |     | 775 |     |     |     |     | 780 |     |     |     |     |     |
| Ile | Leu | Lys | Glu | Leu | Glu | Gly | Glu | Lys | Gly | Lys | Gln | Glu | Val | Leu | Pro |
| 785 |     |     |     |     | 790 |     |     |     |     | 795 |     |     |     |     | 800 |
| Phe | Leu | Glu | Glu | Thr | Tyr | Lys | Lys | Ser | Val | Asp | Glu | Glu | Lys | Leu | Asn |
|     |     |     |     | 805 |     |     |     |     | 810 |     |     |     |     | 815 |     |
| Phe | Tyr | Glu | Glu | Ile | Ile | Lys | Glu | Ile | Glu | Glu | Ile | Asp | Ile | Gly | Asn |
|     |     |     |     | 820 |     |     |     |     | 825 |     |     |     |     | 830 |     |
| Thr | Thr | Pro | Val | Lys | Ala | Leu | Leu | Ile | Leu | Ala | Glu | Leu | Lys | Glu | Arg |
|     |     | 835 |     |     |     |     | 840 |     |     |     |     | 845 |     |     |     |
| Ile | Lys | Ser | Phe | Ile | Lys | Arg |
|     |     | 850 |     |     |     | 855 |

( 2 ) INFORMATION FOR SEQ ID NO:3:

( i ) SEQUENCE CHARACTERISTICS:
        ( A ) LENGTH: 853 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:3:

| Met | Ser | Ala | Ile | Glu | Asn | Phe | Asp | Ala | His | Thr | Pro | Met | Met | Gln | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Tyr | Leu | Arg | Leu | Lys | Ala | Gln | His | Pro | Glu | Ile | Leu | Leu | Phe | Tyr | Arg |
|     |     |     | 20  |     |     |     |     | 25  |     |     |     |     | 30  |     |     |
| Met | Gly | Asp | Phe | Tyr | Glu | Leu | Phe | Tyr | Asp | Asp | Ala | Lys | Arg | Ala | Ser |
|     |     |     | 35  |     |     |     |     | 40  |     |     |     |     | 45  |     |     |
| Gln | Leu | Leu | Asp | Ile | Ser | Leu | Thr | Lys | Arg | Gly | Ala | Ser | Ala | Gly | Glu |
|     |     | 50  |     |     |     |     | 55  |     |     |     |     | 60  |     |     |     |
| Pro | Ile | Pro | Met | Ala | Gly | Ile | Pro | Tyr | His | Ala | Val | Glu | Asn | Tyr | Leu |
| 65  |     |     |     |     | 70  |     |     |     |     | 75  |     |     |     |     | 80  |
| Ala | Lys | Leu | Val | Asn | Gln | Gly | Glu | Ser | Val | Ala | Ile | Cys | Glu | Gln | Ile |
|     |     |     |     | 85  |     |     |     |     | 90  |     |     |     |     | 95  |     |
| Gly | Asp | Pro | Ala | Thr | Ser | Lys | Gly | Pro | Val | Glu | Arg | Lys | Val | Val | Arg |

|     |     |     |     |     | 100 |     |     |     | 105 |     |     |     | 110 |     |
|-----|-----|-----|-----|-----|-----|-----|-----|-----|-----|-----|-----|-----|-----|-----|

Ile Val Thr Pro Gly Thr Ile Ser Asp Glu Ala Leu Leu Gln Glu Arg
            115             120             125

Gln Asp Asn Leu Leu Ala Ala Ile Trp Gln Asp Ser Lys Gly Phe Gly
    130             135             140

Tyr Ala Thr Leu Asp Ile Ser Ser Gly Arg Phe Arg Leu Ser Glu Pro
145             150             155             160

Ala Asp Arg Glu Thr Met Ala Ala Glu Leu Gln Arg Thr Asn Pro Ala
                165             170             175

Glu Leu Leu Tyr Ala Glu Asp Phe Ala Glu Met Ser Leu Ile Glu Gly
            180             185             190

Arg Arg Gly Leu Arg Arg Pro Leu Trp Glu Phe Glu Ile Asp Thr
            195             200             205

Ala Arg Gln Gln Leu Asn Leu Gln Phe Gly Thr Arg Asp Leu Val Gly
    210             215             220

Phe Gly Val Glu Asn Ala Pro Arg Gly Leu Cys Ala Ala Gly Cys Leu
225             230             235             240

Leu Gln Tyr Ala Lys Asp Thr Gln Arg Thr Thr Leu Pro His Ile Arg
                245             250             255

Ser Ile Thr Met Glu Arg Glu Gln Asp Ser Ile Ile Met Asp Ala Ala
            260             265             270

Thr Arg Arg Asn Leu Glu Ile Thr Gln Asn Leu Ala Gly Gly Ala Glu
        275             280             285

Asn Thr Leu Ala Ser Val Leu Asp Cys Thr Val Thr Pro Met Gly Ser
        290             295             300

Arg Met Leu Lys Arg Trp Leu His Met Pro Val Arg Asp Thr Arg Val
305             310             315             320

Leu Leu Glu Arg Gln Gln Thr Ile Gly Ala Leu Gln Asp Phe Thr Ala
                325             330             335

Gly Leu Gln Pro Val Leu Arg Gln Val Gly Asp Leu Glu Arg Ile Leu
            340             345             350

Ala Arg Leu Ala Leu Arg Thr Ala Arg Pro Arg Asp Leu Ala Arg Met
        355             360             365

Arg His Ala Phe Gln Gln Leu Pro Glu Leu Arg Ala Gln Leu Glu Thr
    370             375             380

Val Asp Ser Ala Pro Val Gln Ala Leu Arg Glu Lys Met Gly Glu Phe
385             390             395             400

Ala Glu Leu Arg Asp Leu Leu Glu Arg Ala Ile Ile Asp Thr Pro Pro
            405             410             415

Val Leu Val Arg Asp Gly Gly Val Ile Ala Ser Gly Tyr Asn Glu Glu
            420             425             430

Leu Asp Glu Trp Arg Ala Leu Ala Asp Gly Ala Thr Asp Tyr Leu Glu
            435             440             445

Arg Leu Glu Val Arg Glu Arg Glu Arg Thr Gly Leu Asp Thr Leu Lys
    450             455             460

Val Gly Phe Asn Ala Val His Gly Tyr Tyr Ile Gln Ile Ser Arg Gly
465             470             475             480

Gln Ser His Leu Ala Pro Ile Asn Tyr Met Arg Arg Gln Thr Leu Lys
            485             490             495

Asn Ala Glu Arg Tyr Ile Ile Pro Glu Leu Lys Glu Tyr Glu Asp Lys
            500             505             510

Val Leu Thr Ser Lys Gly Lys Ala Leu Ala Leu Glu Lys Gln Leu Tyr
        515             520             525

|     |     |     |     |     |     |     |     |     |     |     |     |     |     |     |
|-----|-----|-----|-----|-----|-----|-----|-----|-----|-----|-----|-----|-----|-----|-----|
| Glu | Glu 530 | Leu | Phe | Asp | Leu | Leu 535 | Leu | Pro | His | Leu | Glu 540 | Ala | Leu | Gln | Gln |
| Ser 545 | Ala | Ser | Ala | Leu | Ala 550 | Glu | Leu | Asp | Val | Leu 555 | Val | Asn | Leu | Ala | Glu 560 |
| Arg | Ala | Tyr | Thr | Leu 565 | Asn | Tyr | Thr | Cys | Pro 570 | Thr | Phe | Ile | Asp | Lys 575 | Pro |
| Gly | Ile | Arg | Ile 580 | Thr | Glu | Gly | Arg | His 585 | Pro | Val | Val | Glu | Gln 590 | Val | Leu |
| Asn | Glu | Pro 595 | Phe | Ile | Ala | Asn | Pro 600 | Leu | Asn | Leu | Ser | Pro 605 | Gln | Arg | Arg |
| Met | Leu 610 | Ile | Ile | Thr | Gly | Pro 615 | Asn | Met | Gly | Gly | Lys 620 | Ser | Thr | Tyr | Met |
| Arg 625 | Gln | Thr | Ala | Leu | Ile 630 | Ala | Leu | Met | Ala | Tyr 635 | Ile | Gly | Ser | Tyr | Val 640 |
| Pro | Ala | Gln | Lys | Val 645 | Glu | Ile | Gly | Pro | Ile 650 | Asp | Arg | Ile | Phe | Thr 655 | Arg |
| Val | Gly | Ala | Ala 660 | Asp | Asp | Leu | Ala | Ser 665 | Gly | Arg | Ser | Thr | Phe 670 | Met | Val |
| Glu | Met | Thr 675 | Glu | Thr | Ala | Asn | Ile 680 | Leu | His | Asn | Ala | Thr 685 | Glu | Tyr | Ser |
| Leu | Val 690 | Leu | Met | Asp | Glu | Ile 695 | Gly | Arg | Gly | Thr | Ser 700 | Thr | Tyr | Asp | Gly |
| Leu 705 | Ser | Leu | Ala | Trp | Ala 710 | Cys | Ala | Glu | Asn | Leu 715 | Ala | Asn | Lys | Ile | Lys 720 |
| Ala | Leu | Thr | Leu | Phe 725 | Ala | Thr | His | Tyr | Phe 730 | Glu | Leu | Thr | Gln | Leu 735 | Pro |
| Glu | Lys | Met | Glu 740 | Gly | Val | Ala | Asn | Val 745 | His | Leu | Asp | Ala | Leu 750 | Glu | His |
| Gly | Asp | Thr 755 | Ile | Ala | Phe | Met | His 760 | Ser | Val | Gln | Asp | Gly 765 | Ala | Ala | Ser |
| Lys | Ser 770 | Tyr | Gly | Leu | Ala | Val 775 | Ala | Ala | Leu | Ala | Gly 780 | Val | Pro | Lys | Glu |
| Val 785 | Ile | Lys | Arg | Ala | Arg 790 | Gln | Lys | Leu | Arg | Glu 795 | Leu | Glu | Ser | Ile | Ser 800 |
| Pro | Asn | Ala | Ala | Ala 805 | Thr | Gln | Val | Asp | Gly 810 | Thr | Gln | Met | Ser | Leu 815 | Leu |
| Ser | Val | Pro | Glu 820 | Glu | Thr | Ser | Pro | Ala 825 | Val | Glu | Ala | Leu 830 | Glu | Asn | Leu |
| Asp | Pro | Asp 835 | Ser | Leu | Thr | Pro | Arg 840 | Gln | Ala | Leu | Glu | Trp 845 | Ile | Tyr | Arg |
| Leu | Lys 850 | Ser | Leu | Val |     |     |     |     |     |     |     |     |     |     |     |

( 2 ) INFORMATION FOR SEQ ID NO:4:

( i ) SEQUENCE CHARACTERISTICS:
        ( A ) LENGTH: 2382 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2379

( x i ) SEQUENCE DESCRIPTION: SEQ ID NO:4:

| | | | | | | | | | | | | | | | | |
|---|---|---|---|---|---|---|---|---|---|---|---|---|---|---|---|---|
| GTG | AAG | GTA | ACT | CCC | CTC | ATG | GAA | CAG | TAC | CTG | AGA | ATA | AAA | GAA | CAG | 48 |
| Val | Lys | Val | Thr | Pro | Leu | Met | Glu | Gln | Tyr | Leu | Arg | Ile | Lys | Glu | Gln | |
| 1 | | | | 5 | | | | | 10 | | | | | 15 | | |
| TAC | AAA | GAT | TCC | ATT | CTG | CTG | TTT | CGA | CTG | GGA | GAT | TTT | TAC | GAG | GCG | 96 |
| Tyr | Lys | Asp | Ser | Ile | Leu | Leu | Phe | Arg | Leu | Gly | Asp | Phe | Tyr | Glu | Ala | |
| | | | 20 | | | | | 25 | | | | | 30 | | | |
| TTT | TTC | GAA | GAC | GCA | AAG | ATC | GTT | TCG | AAG | GTT | CTG | AAC | ATA | GTT | CTC | 144 |
| Phe | Phe | Glu | Asp | Ala | Lys | Ile | Val | Ser | Lys | Val | Leu | Asn | Ile | Val | Leu | |
| | | 35 | | | | | 40 | | | | | 45 | | | | |
| ACA | AGA | AGG | CAG | GAC | GCT | CCC | ATG | GCG | GGC | ATC | CCG | TAC | CAC | GCG | CTG | 192 |
| Thr | Arg | Arg | Gln | Asp | Ala | Pro | Met | Ala | Gly | Ile | Pro | Tyr | His | Ala | Leu | |
| | 50 | | | | | 55 | | | | | 60 | | | | | |
| AAC | ACC | TAC | CTG | AAA | AAG | CTC | GTC | GAA | GCG | GGC | TAC | AAG | GTG | GCA | ATC | 240 |
| Asn | Thr | Tyr | Leu | Lys | Lys | Leu | Val | Glu | Ala | Gly | Tyr | Lys | Val | Ala | Ile | |
| 65 | | | | | 70 | | | | | 75 | | | | | 80 | |
| TGC | GAT | CAA | ATG | GAA | GAA | CCT | TCG | AAG | TCG | AAG | AAA | TTG | ATC | AGA | AGG | 288 |
| Cys | Asp | Gln | Met | Glu | Glu | Pro | Ser | Lys | Ser | Lys | Lys | Leu | Ile | Arg | Arg | |
| | | | | 85 | | | | | 90 | | | | | 95 | | |
| GAA | GTC | ACG | CGC | GTT | GTC | ACT | CCC | GGC | TCC | ATC | GTA | GAG | GAT | GAG | TTT | 336 |
| Glu | Val | Thr | Arg | Val | Val | Thr | Pro | Gly | Ser | Ile | Val | Glu | Asp | Glu | Phe | |
| | | | 100 | | | | | 105 | | | | | 110 | | | |
| CTC | AGC | GAA | ACG | AAC | AAC | TAC | ATG | GCC | GTT | GTC | TCA | GAA | GAG | AAA | GGA | 384 |
| Leu | Ser | Glu | Thr | Asn | Asn | Tyr | Met | Ala | Val | Val | Ser | Glu | Glu | Lys | Gly | |
| | | 115 | | | | | 120 | | | | | 125 | | | | |
| CGG | TAC | TGT | ACG | GTT | TTC | TGT | GAT | GTC | TCG | ACA | GGT | GAG | GTC | CTG | GTT | 432 |
| Arg | Tyr | Cys | Thr | Val | Phe | Cys | Asp | Val | Ser | Thr | Gly | Glu | Val | Leu | Val | |
| | 130 | | | | | 135 | | | | | 140 | | | | | |
| CAT | GAA | AGT | TCA | GAC | GAA | CAG | GAA | ACT | TTG | GAC | CTG | CTG | AAG | AAT | TAC | 480 |
| His | Glu | Ser | Ser | Asp | Glu | Gln | Glu | Thr | Leu | Asp | Leu | Leu | Lys | Asn | Tyr | |
| 145 | | | | | 150 | | | | | 155 | | | | | 160 | |
| TCC | ATT | TCC | CAG | ATC | ATC | TGT | CCA | GAG | CAC | CTG | AAA | TCT | TCT | TTG | AAG | 528 |
| Ser | Ile | Ser | Gln | Ile | Ile | Cys | Pro | Glu | His | Leu | Lys | Ser | Ser | Leu | Lys | |
| | | | | 165 | | | | | 170 | | | | | 175 | | |
| GAA | CGC | TTT | CCA | GGT | GTT | TAC | ACA | GAA | ACC | ATA | AGC | GAG | TGG | TAT | TTC | 576 |
| Glu | Arg | Phe | Pro | Gly | Val | Tyr | Thr | Glu | Thr | Ile | Ser | Glu | Trp | Tyr | Phe | |
| | | | 180 | | | | | 185 | | | | | 190 | | | |
| TCA | GAT | CTG | GAA | GAA | GTG | GAA | AAA | GCC | TAC | AAT | CTG | AAA | GAC | ATT | CAT | 624 |
| Ser | Asp | Leu | Glu | Glu | Val | Glu | Lys | Ala | Tyr | Asn | Leu | Lys | Asp | Ile | His | |
| | | 195 | | | | | 200 | | | | | 205 | | | | |
| CAT | TTC | GAG | CTT | TCG | CCC | CTT | GCG | CTG | AAA | GCC | CTT | GCG | GCG | CTG | ATA | 672 |
| His | Phe | Glu | Leu | Ser | Pro | Leu | Ala | Leu | Lys | Ala | Leu | Ala | Ala | Leu | Ile | |
| | 210 | | | | | 215 | | | | | 220 | | | | | |
| AAG | TAT | GTC | AAG | TAC | ACG | ATG | ATC | GGG | GAA | GAT | CTG | AAT | CTG | AAA | CCC | 720 |
| Lys | Tyr | Val | Lys | Tyr | Thr | Met | Ile | Gly | Glu | Asp | Leu | Asn | Leu | Lys | Pro | |
| 225 | | | | | 230 | | | | | 235 | | | | | 240 | |
| CCT | CTT | CTC | ATC | TCC | CAG | AGA | GAC | TAC | ATG | ATA | CTC | GAT | TCC | GCA | ACG | 768 |
| Pro | Leu | Leu | Ile | Ser | Gln | Arg | Asp | Tyr | Met | Ile | Leu | Asp | Ser | Ala | Thr | |
| | | | | 245 | | | | | 250 | | | | | 255 | | |
| GTG | GAA | AAT | CTT | TCT | TGG | ATT | CCC | GGT | GAC | AGG | GGA | AAG | AAT | CTT | TTC | 816 |
| Val | Glu | Asn | Leu | Ser | Trp | Ile | Pro | Gly | Asp | Arg | Gly | Lys | Asn | Leu | Phe | |
| | | | 260 | | | | | 265 | | | | | 270 | | | |
| GAT | GTG | CTG | AAC | AAC | ACG | GAA | ACT | CCT | ATG | GGG | GCT | CGT | CTT | GGG | AAA | 864 |
| Asp | Val | Leu | Asn | Asn | Thr | Glu | Thr | Pro | Met | Gly | Ala | Arg | Leu | Gly | Lys | |
| | | 275 | | | | | 280 | | | | | 285 | | | | |
| AAG | TGG | ATT | CTC | CAC | CCT | CTG | GTC | GAC | AGA | AAA | CAG | ATC | GAA | GAA | AGG | 912 |
| Lys | Trp | Ile | Leu | His | Pro | Leu | Val | Asp | Arg | Lys | Gln | Ile | Glu | Glu | Arg | |
| | 290 | | | | | 295 | | | | | 300 | | | | | |
| CTC | AAG | GCT | GTG | GAA | AGA | CTG | GTG | AAC | GAC | AGG | GTG | AGC | CTG | GAG | GAG | 960 |
| Leu | Lys | Ala | Val | Glu | Arg | Leu | Val | Asn | Asp | Arg | Val | Ser | Leu | Glu | Glu | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ATG | AGG | AAC | CTT | CTT | TCG | AAC | GTG | AGG | GAT | GTG | GAG | CGG | ATC | GTT | TCG | 1008 |
| Met | Arg | Asn | Leu | Leu | Ser | Asn | Val | Arg | Asp | Val | Glu | Arg | Ile | Val | Ser | |
| | | | | 325 | | | | 330 | | | | | 335 | | | |
| CGG | GTG | GAG | TAC | AAC | AGA | TCC | GTT | CCC | AGG | GAC | TTA | GTG | GCA | CTC | AGA | 1056 |
| Arg | Val | Glu | Tyr | Asn | Arg | Ser | Val | Pro | Arg | Asp | Leu | Val | Ala | Leu | Arg | |
| | | | 340 | | | | | 345 | | | | | 350 | | | |
| GAG | ACA | CTG | GAG | ATC | ATC | CCG | AAA | CTG | AAC | GAA | GTT | CTT | TCA | ACC | TTC | 1104 |
| Glu | Thr | Leu | Glu | Ile | Ile | Pro | Lys | Leu | Asn | Glu | Val | Leu | Ser | Thr | Phe | |
| | | 355 | | | | | 360 | | | | | 365 | | | | |
| GGT | GTG | TTC | AAG | AAA | CTC | GCT | TTC | CCG | GAA | GGA | CTG | GTT | GAT | CTG | CTT | 1152 |
| Gly | Val | Phe | Lys | Lys | Leu | Ala | Phe | Pro | Glu | Gly | Leu | Val | Asp | Leu | Leu | |
| | 370 | | | | | 375 | | | | | 380 | | | | | |
| CGA | AAA | GCC | ATT | GAA | GAT | GAT | CCG | GTG | GGA | AGC | CCC | GGC | GAG | GGA | AAA | 1200 |
| Arg | Lys | Ala | Ile | Glu | Asp | Asp | Pro | Val | Gly | Ser | Pro | Gly | Glu | Gly | Lys | |
| 385 | | | | 390 | | | | | 395 | | | | | | 400 | |
| GTT | ATA | AAG | AGA | GGA | TTC | TCA | TCT | GAA | CTC | GAC | GAA | TAC | AGG | GAT | CTT | 1248 |
| Val | Ile | Lys | Arg | Gly | Phe | Ser | Ser | Glu | Leu | Asp | Glu | Tyr | Arg | Asp | Leu | |
| | | | | 405 | | | | 410 | | | | | 415 | | | |
| CTG | GAA | CAT | GCC | GAA | GAG | AGG | CTC | AAA | GAG | TTC | GAG | GAG | AAG | GAG | AGA | 1296 |
| Leu | Glu | His | Ala | Glu | Glu | Arg | Leu | Lys | Glu | Phe | Glu | Glu | Lys | Glu | Arg | |
| | | | 420 | | | | 425 | | | | | 430 | | | | |
| GAA | AGA | ACA | GGC | ATC | CAA | AAA | CTG | CGG | GTT | GGA | TAC | AAC | CAG | GTT | TTT | 1344 |
| Glu | Arg | Thr | Gly | Ile | Gln | Lys | Leu | Arg | Val | Gly | Tyr | Asn | Gln | Val | Phe | |
| | | 435 | | | | | 440 | | | | | 445 | | | | |
| GGT | TAC | TAC | ATA | GAG | GTG | ACG | AAG | GCG | AAT | CTG | GAT | AAG | ATT | CCC | GAC | 1392 |
| Gly | Tyr | Tyr | Ile | Glu | Val | Thr | Lys | Ala | Asn | Leu | Asp | Lys | Ile | Pro | Asp | |
| | | 450 | | | | | 455 | | | | | 460 | | | | |
| GAT | TAC | GAA | AGA | AAA | CAA | ACA | CTC | GTC | AAT | TCT | GAA | AGA | TTC | ATC | ACA | 1440 |
| Asp | Tyr | Glu | Arg | Lys | Gln | Thr | Leu | Val | Asn | Ser | Glu | Arg | Phe | Ile | Thr | |
| 465 | | | | | 470 | | | | | 475 | | | | | 480 | |
| CCC | GAA | TTG | AAG | GAG | TTC | GAG | ACA | AAG | ATA | ATG | GCC | GCT | AAA | GAG | AGA | 1488 |
| Pro | Glu | Leu | Lys | Glu | Phe | Glu | Thr | Lys | Ile | Met | Ala | Ala | Lys | Glu | Arg | |
| | | | | 485 | | | | 490 | | | | | 495 | | | |
| ATA | GAA | GAA | CTG | GAA | AAG | GAA | CTC | TTC | ACA | AGC | GTG | TGC | GAA | GAG | GTG | 1536 |
| Ile | Glu | Glu | Leu | Glu | Lys | Glu | Leu | Phe | Thr | Ser | Val | Cys | Glu | Glu | Val | |
| | | | 500 | | | | 505 | | | | | 510 | | | | |
| AAA | AAG | CAC | AAA | GAA | GTT | CTC | CTT | GAG | ATC | TCG | GAG | GAT | CTG | GCA | AAG | 1584 |
| Lys | Lys | His | Lys | Glu | Val | Leu | Leu | Glu | Ile | Ser | Glu | Asp | Leu | Ala | Lys | |
| | | 515 | | | | | 520 | | | | | 525 | | | | |
| ATA | GAT | GCG | CTT | TCG | ACG | TTA | GCA | TAC | GAC | GCT | ATT | ATG | TAC | AAC | TAC | 1632 |
| Ile | Asp | Ala | Leu | Ser | Thr | Leu | Ala | Tyr | Asp | Ala | Ile | Met | Tyr | Asn | Tyr | |
| | 530 | | | | | 535 | | | | | 540 | | | | | |
| ACA | AAA | CCC | GTC | TTT | TCA | GAA | GAC | AGA | CTG | GAG | ATC | AAA | GGT | GGA | AGA | 1680 |
| Thr | Lys | Pro | Val | Phe | Ser | Glu | Asp | Arg | Leu | Glu | Ile | Lys | Gly | Gly | Arg | |
| 545 | | | | | 550 | | | | | 555 | | | | | 560 | |
| CAC | CCG | GTC | GTT | GAA | AGG | TTC | ACA | CAG | AAT | TTT | GTT | GAA | AAC | GAT | ATT | 1728 |
| His | Pro | Val | Val | Glu | Arg | Phe | Thr | Gln | Asn | Phe | Val | Glu | Asn | Asp | Ile | |
| | | | | 565 | | | | 570 | | | | | 575 | | | |
| TAC | ATG | GAC | AAC | GAG | AAG | AGA | TTT | GTG | GTA | ATA | ACG | GGT | CCC | AAC | ATG | 1776 |
| Tyr | Met | Asp | Asn | Glu | Lys | Arg | Phe | Val | Val | Ile | Thr | Gly | Pro | Asn | Met | |
| | | | 580 | | | | | 585 | | | | | 590 | | | |
| AGC | GGG | AAG | TCC | ACT | TTC | ATC | AGA | CAG | GTG | GGT | CTC | ATC | TCC | CTC | ATG | 1824 |
| Ser | Gly | Lys | Ser | Thr | Phe | Ile | Arg | Gln | Val | Gly | Leu | Ile | Ser | Leu | Met | |
| | | 595 | | | | | 600 | | | | | 605 | | | | |
| GCG | CAG | ATA | GGA | TCG | TTT | GTG | CCG | GCG | CAG | AAG | GCG | ATT | CTT | CCA | GTG | 1872 |
| Ala | Gln | Ile | Gly | Ser | Phe | Val | Pro | Ala | Gln | Lys | Ala | Ile | Leu | Pro | Val | |
| | 610 | | | | | 615 | | | | | 620 | | | | | |
| TTC | GAC | AGG | ATT | TTC | ACG | CGA | ATG | GGT | GCC | AGA | GAC | GAT | CTC | GCT | GGT | 1920 |
| Phe | Asp | Arg | Ile | Phe | Thr | Arg | Met | Gly | Ala | Arg | Asp | Asp | Leu | Ala | Gly | |
| 625 | | | | | 630 | | | | | 635 | | | | | 640 | |

| | | | | | | | | | | | | | | | | |
|---|---|---|---|---|---|---|---|---|---|---|---|---|---|---|---|---|
| GGT | AGA | AGT | ACG | TTC | CTT | GTC | GAG | ATG | AAC | GAG | ATG | GCG | CTC | ATC | CTT | 1968 |
| Gly | Arg | Ser | Thr 645 | Phe | Leu | Val | Glu | Met 650 | Asn | Glu | Met | Ala | Leu | Ile 655 | Leu | |
| CTG | AAA | TCA | ACA | AAT | AAG | AGT | CTG | GTT | CTC | CTG | GAC | GAG | GTG | GGA | AGA | 2016 |
| Leu | Lys | Ser | Thr 660 | Asn | Lys | Ser | Leu | Val 665 | Leu | Leu | Asp | Glu | Val 670 | Gly | Arg | |
| GGT | ACA | AGC | ACC | CAG | GAC | GGC | GTC | AGC | ATA | GCC | TGG | GCA | ATC | TCA | GAG | 2064 |
| Gly | Thr | Ser 675 | Thr | Gln | Asp | Gly | Val 680 | Ser | Ile | Ala | Trp | Ala 685 | Ile | Ser | Glu | |
| GAA | CTC | ATA | AAG | AGA | GGA | TGT | AAG | GTG | CTG | TTT | GCC | ACT | CAT | TTC | ACG | 2112 |
| Glu | Leu 690 | Ile | Lys | Arg | Gly | Cys 695 | Lys | Val | Leu | Phe | Ala 700 | Thr | His | Phe | Thr | |
| GAA | CTC | ACG | GAA | CTC | GAA | AAA | CAC | TTT | CCG | CAG | GTT | CAG | AAC | AAA | ACC | 2160 |
| Glu 705 | Leu | Thr | Glu | Leu | Glu 710 | Lys | His | Phe | Pro | Gln 715 | Val | Gln | Asn | Lys | Thr 720 | |
| ATT | CTG | GTA | AAA | GAA | GAA | GGC | AAA | AAC | GTG | ATA | TTC | ACC | CAC | AAG | GTG | 2208 |
| Ile | Leu | Val | Lys | Glu 725 | Glu | Gly | Lys | Asn | Val 730 | Ile | Phe | Thr | His | Lys 735 | Val | |
| GTG | GAC | GGT | GTG | GCA | GAC | AGA | AGT | TAC | GGA | ATA | GAG | GTC | GCA | AAG | ATA | 2256 |
| Val | Asp | Gly | Val 740 | Ala | Asp | Arg | Ser | Tyr 745 | Gly | Ile | Glu | Val | Ala 750 | Lys | Ile | |
| GCG | GGT | ATT | CCT | GAC | AGG | GTT | ATA | AAC | AGA | GCC | TAT | GAA | ATT | CTG | GAG | 2304 |
| Ala | Gly | Ile 755 | Pro | Asp | Arg | Val | Ile 760 | Asn | Arg | Ala | Tyr | Glu 765 | Ile | Leu | Glu | |
| AGG | AAT | TTC | AAA | AAC | AAC | ACG | AAG | AAA | AAC | GGA | AAA | TCG | AAC | AGA | TTC | 2352 |
| Arg | Asn | Phe 770 | Lys | Asn | Asn | Thr | Lys 775 | Lys | Asn | Gly | Lys | Ser 780 | Asn | Arg | Phe | |
| AGT | CAG | CAA | ATT | CCT | CTC | TTT | CCT | GTT | TGA | | | | | | | 2382 |
| Ser 785 | Gln | Gln | Ile | Pro | Leu 790 | Phe | Pro | Val | | | | | | | | |

( 2 ) INFORMATION FOR SEQ ID NO:5:

( i ) SEQUENCE CHARACTERISTICS:
        ( A ) LENGTH: 793 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Val 1 | Lys | Val | Thr | Pro 5 | Leu | Met | Glu | Gln | Tyr 10 | Leu | Arg | Ile | Lys | Glu 15 | Gln |
| Tyr | Lys | Asp | Ser 20 | Ile | Leu | Leu | Phe | Arg 25 | Leu | Gly | Asp | Phe | Tyr 30 | Glu | Ala |
| Phe | Phe | Glu 35 | Asp | Ala | Lys | Ile | Val 40 | Ser | Lys | Val | Leu | Asn 45 | Ile | Val | Leu |
| Thr | Arg 50 | Arg | Gln | Asp | Ala | Pro 55 | Met | Ala | Gly | Ile | Pro 60 | Tyr | His | Ala | Leu |
| Asn 65 | Thr | Tyr | Leu | Lys | Lys 70 | Leu | Val | Glu | Ala | Gly 75 | Tyr | Lys | Val | Ala | Ile 80 |
| Cys | Asp | Gln | Met | Glu 85 | Glu | Pro | Ser | Lys | Ser 90 | Lys | Lys | Leu | Ile | Arg 95 | Arg |
| Glu | Val | Thr | Arg 100 | Val | Val | Thr | Pro | Gly 105 | Ser | Ile | Val | Glu | Asp 110 | Glu | Phe |
| Leu | Ser | Glu 115 | Thr | Asn | Asn | Tyr | Met 120 | Ala | Val | Val | Ser | Glu 125 | Glu | Lys | Gly |
| Arg | Tyr 130 | Cys | Thr | Val | Phe | Cys 135 | Asp | Val | Ser | Thr | Gly 140 | Glu | Val | Leu | Val |
| His | Glu | Ser | Ser | Asp | Glu | Gln | Glu | Thr | Leu | Asp | Leu | Leu | Lys | Asn | Tyr |

|     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- |

Ser Ile Ser Gln Ile Ile Cys Pro Glu His Leu Lys Ser Ser Leu Lys
                165                     170                     175

Glu Arg Phe Pro Gly Val Tyr Thr Glu Thr Ile Ser Glu Trp Tyr Phe
                180                     185                     190

Ser Asp Leu Glu Glu Val Glu Lys Ala Tyr Asn Leu Lys Asp Ile His
                195                     200                     205

His Phe Glu Leu Ser Pro Leu Ala Leu Lys Ala Leu Ala Ala Leu Ile
        210                     215                     220

Lys Tyr Val Lys Tyr Thr Met Ile Gly Glu Asp Leu Asn Leu Lys Pro
225                     230                     235                     240

Pro Leu Leu Ile Ser Gln Arg Asp Tyr Met Ile Leu Asp Ser Ala Thr
                245                     250                     255

Val Glu Asn Leu Ser Trp Ile Pro Gly Asp Arg Gly Lys Asn Leu Phe
                260                     265                     270

Asp Val Leu Asn Asn Thr Glu Thr Pro Met Gly Ala Arg Leu Gly Lys
            275                     280                     285

Lys Trp Ile Leu His Pro Leu Val Asp Arg Lys Gln Ile Glu Glu Arg
        290                     295                     300

Leu Lys Ala Val Glu Arg Leu Val Asn Asp Arg Val Ser Leu Glu Glu
305                     310                     315                     320

Met Arg Asn Leu Leu Ser Asn Val Arg Asp Val Glu Arg Ile Val Ser
                325                     330                     335

Arg Val Glu Tyr Asn Arg Ser Val Pro Arg Asp Leu Val Ala Leu Arg
            340                     345                     350

Glu Thr Leu Glu Ile Ile Pro Lys Leu Asn Glu Val Leu Ser Thr Phe
        355                     360                     365

Gly Val Phe Lys Lys Leu Ala Phe Pro Glu Gly Leu Val Asp Leu Leu
    370                     375                     380

Arg Lys Ala Ile Glu Asp Asp Pro Val Gly Ser Pro Gly Glu Gly Lys
385                     390                     395                     400

Val Ile Lys Arg Gly Phe Ser Ser Glu Leu Asp Glu Tyr Arg Asp Leu
                405                     410                     415

Leu Glu His Ala Glu Glu Arg Leu Lys Glu Phe Glu Glu Lys Glu Arg
            420                     425                     430

Glu Arg Thr Gly Ile Gln Lys Leu Arg Val Gly Tyr Asn Gln Val Phe
        435                     440                     445

Gly Tyr Tyr Ile Glu Val Thr Lys Ala Asn Leu Asp Lys Ile Pro Asp
    450                     455                     460

Asp Tyr Glu Arg Lys Gln Thr Leu Val Asn Ser Glu Arg Phe Ile Thr
465                     470                     475                     480

Pro Glu Leu Lys Glu Phe Glu Thr Lys Ile Met Ala Ala Lys Glu Arg
                485                     490                     495

Ile Glu Glu Leu Glu Lys Glu Leu Phe Thr Ser Val Cys Glu Glu Val
            500                     505                     510

Lys Lys His Lys Glu Val Leu Leu Glu Ile Ser Glu Asp Leu Ala Lys
        515                     520                     525

Ile Asp Ala Leu Ser Thr Leu Ala Tyr Asp Ala Ile Met Tyr Asn Tyr
    530                     535                     540

Thr Lys Pro Val Phe Ser Glu Asp Arg Leu Glu Ile Lys Gly Gly Arg
545                     550                     555                     560

His Pro Val Val Glu Arg Phe Thr Gln Asn Phe Val Glu Asn Asp Ile
                565                     570                     575

| | | | | | | | | | | | | | | |
|---|---|---|---|---|---|---|---|---|---|---|---|---|---|---|
|Tyr|Met|Asp|Asn|Glu|Lys|Arg|Phe|Val|Val|Ile|Thr|Gly|Pro|Asn|Met|
| | | |580| | | |585| | | | |590| | |
|Ser|Gly|Lys|Ser|Thr|Phe|Ile|Arg|Gln|Val|Gly|Leu|Ile|Ser|Leu|Met|
| | |595| | | |600| | | | |605| | | |
|Ala|Gln|Ile|Gly|Ser|Phe|Val|Pro|Ala|Gln|Lys|Ala|Ile|Leu|Pro|Val|
| |610| | | |615| | | | |620| | | | |
|Phe|Asp|Arg|Ile|Phe|Thr|Arg|Met|Gly|Ala|Arg|Asp|Asp|Leu|Ala|Gly|
|625| | | |630| | | | |635| | | | |640| |
|Gly|Arg|Ser|Thr|Phe|Leu|Val|Glu|Met|Asn|Glu|Met|Ala|Leu|Ile|Leu|
| | | |645| | | | |650| | | | |655| | |
|Leu|Lys|Ser|Thr|Asn|Lys|Ser|Leu|Val|Leu|Leu|Asp|Glu|Val|Gly|Arg|
| | |660| | | | |665| | | | |670| | | |
|Gly|Thr|Ser|Thr|Gln|Asp|Gly|Val|Ser|Ile|Ala|Trp|Ala|Ile|Ser|Glu|
| | |675| | | | |680| | | | |685| | | |
|Glu|Leu|Ile|Lys|Arg|Gly|Cys|Lys|Val|Leu|Phe|Ala|Thr|His|Phe|Thr|
| |690| | | | |695| | | | |700| | | | |
|Glu|Leu|Thr|Glu|Leu|Glu|Lys|His|Phe|Pro|Gln|Val|Gln|Asn|Lys|Thr|
|705| | | | |710| | | | |715| | | | |720|
|Ile|Leu|Val|Lys|Glu|Gly|Lys|Asn|Val|Ile|Phe|Thr|His|Lys|Val| |
| | | | |725| | | | |730| | | |735| | |
|Val|Asp|Gly|Val|Ala|Asp|Arg|Ser|Tyr|Gly|Ile|Glu|Val|Ala|Lys|Ile|
| | | |740| | | | |745| | | | |750| | |
|Ala|Gly|Ile|Pro|Asp|Arg|Val|Ile|Asn|Arg|Ala|Tyr|Glu|Ile|Leu|Glu|
| | |755| | | | |760| | | | |765| | | |
|Arg|Asn|Phe|Lys|Asn|Asn|Thr|Lys|Lys|Asn|Gly|Lys|Ser|Asn|Arg|Phe|
| |770| | | | |775| | | | |780| | | | |
|Ser|Gln|Gln|Ile|Pro|Leu|Phe|Pro|Val| | | | | | | |
|785| | | | |790| | | | | | | | | | |

( 2 ) INFORMATION FOR SEQ ID NO:6:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

```
AAGTCCACCT TCCTCCGCCG GACCGCCCTC ATCGCCCTCC TCGCCCAGAT CGGGAGCTTC      60
GCGCCCGCCG AGGGGCTGCT GCTTCCCCTC TTTGACGGGA TC                        102
```

( 2 ) INFORMATION FOR SEQ ID NO:7:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

```
AAGTCCACCT TTCTGCGCCA GACGGCCCTC ATCGCCCTCC TGGCCCAGGT GGGGAGCTTC      60
GTGCCCGCCG AGGAGGCCCA TCTTCCCCTC TTTGACGGCA TC                        102
```

( 2 ) INFORMATION FOR SEQ ID NO:8:

( i ) SEQUENCE CHARACTERISTICS:

( A ) LENGTH: 34 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:8:

| Lys | Ser | Thr | Phe | Leu | Arg | Gln | Thr | Ala | Leu | Ile | Ala | Leu | Leu | Ala | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Gly | Ser | Phe | Val | Pro | Ala | Glu | Glu | Ala | His | Leu | Pro | Leu | Phe | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Gly Ile ( 2 ) INFORMATION FOR SEQ ID NO:9:

( i ) SEQUENCE CHARACTERISTICS:
( A ) LENGTH: 34 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:9:

| Lys | Ser | Thr | Phe | Leu | Arg | Arg | Thr | Ala | Leu | Ile | Ala | Leu | Leu | Ala | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Gly | Ser | Phe | Ala | Pro | Ala | Glu | Gly | Leu | Leu | Leu | Pro | Leu | Phe | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Gly Ile ( 2 ) INFORMATION FOR SEQ ID NO:10:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( x i ) SEQUENCE DESCRIPTION: SEQ ID NO:10:

GGGGATCCTC                                                                                                  10

( 2 ) INFORMATION FOR SEQ ID NO:11:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( x i ) SEQUENCE DESCRIPTION: SEQ ID NO:11:

GGGACCCTC                                                                                                    9

( 2 ) INFORMATION FOR SEQ ID NO:12:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( x i ) SEQUENCE DESCRIPTION: SEQ ID NO:12:

GGGGATCCCT C                                                                                                11

( 2 ) INFORMATION FOR SEQ ID NO:13:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

GGGGATCCCC CTC      13

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PCR primer"

( x i ) SEQUENCE DESCRIPTION: SEQ ID NO:14:

TACGCCAGCT GGCGAAAGGG      20

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PCR primer"

( x i ) SEQUENCE DESCRIPTION: SEQ ID NO:15:

AATGCAGCTG GCACGACAGG      20

( 2 ) INFORMATION FOR SEQ ID NO:16:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

GACTCTAGAG GATCCATGT      19

( 2 ) INFORMATION FOR SEQ ID NO:17:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "PCR primer"

( x i ) SEQUENCE DESCRIPTION: SEQ ID NO:17:

AUGAUGAUGA UGAUCGCACA TTTCCCCGAA AAGTG      35

( 2 ) INFORMATION FOR SEQ ID NO:18:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear (i i) MOLECULE TYPE: other nucleic acid
    (A) DESCRIPTION: /desc = "PCR primer"

(x i) SEQUENCE DESCRIPTION: SEQ ID NO:18:

AUCAUCAUCA UCAUGCGCGG AACCCCTATT TGT　　　　　　　　　　　　　　　　33

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "primer"

(x i) SEQUENCE DESCRIPTION: SEQ ID NO:19:

GCGGAATTCC SAACATGGGS GGNAA　　　　　　　　　　　　　　　　　　　　25

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:20:

GCGAGATCTA AGTAGTGSGT NGCRAA　　　　　　　　　　　　　　　　　　　26

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:21:

GCGAGATCTC ACCTGTCTTA TGTAGCTCGA　　　　　　　　　　　　　　　　　30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:22:

GCGAGATCTC ATCTCGACAA GGAACGTACT　　　　　　　　　　　　　　　　　30

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: other nucleic acid
  (A) DESCRIPTION: /desc = "Primer"

(x i) SEQUENCE DESCRIPTION: SEQ ID NO:23:

GCGGAATTCA TGGGGGAYTT YTAYGA                                    26

(2) INFORMATION FOR SEQ ID NO:24:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "primer"

(x i) SEQUENCE DESCRIPTION: SEQ ID NO:24:

GCGGAATTCG GGAAAGGATT CCCATGTTCG                                30

(2) INFORMATION FOR SEQ ID NO:25:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "primer"

(x i) SEQUENCE DESCRIPTION: SEQ ID NO:25:

GCGAGATCTC CTTTCCAGCG GGTCTTGAAG                                30

(2) INFORMATION FOR SEQ ID NO:26:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "primer"

(x i) SEQUENCE DESCRIPTION: SEQ ID NO:26:

GCGGAATTCC GGGCATCCCG TACCACTCGC                                30

(2) INFORMATION FOR SEQ ID NO:27:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "primer"

(x i) SEQUENCE DESCRIPTION: SEQ ID NO:27:

GCGAGATCTG GAGCGTCCCT GCCCTTCTTG                                30

(2) INFORMATION FOR SEQ ID NO:28:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:28:

GCGGAATTCT CAACCTTCAT GAACGAGATG          30

(2) INFORMATION FOR SEQ ID NO:29:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:29:

GCGAGATCTC GAGCCTATTC TCATGAATAT          30

(2) INFORMATION FOR SEQ ID NO:30:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:30:

GCGGAATTCG AGGTGGGAAG AGGTACAAGC          30

(2) INFORMATION FOR SEQ ID NO:31:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:31:

GCGAGATCTC ATCTCGACAA GGAACGTACT          30

(2) INFORMATION FOR SEQ ID NO:32:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "PCR primer"

(xi) SEQUENCE DESCRIPTION: SEQ ID NO:32:

GCGAAGCTTA TGAAGGTAAC TCCCCTCATG          30

(2) INFORMATION FOR SEQ ID NO:33:

(i) SEQUENCE CHARACTERISTICS:
    (A) LENGTH: 30 base pairs
    (B) TYPE: nucleic acid
    (C) STRANDEDNESS: single
    (D) TOPOLOGY: linear ( i i ) MOLECULE TYPE: other nucleic acid
 ( A ) DESCRIPTION: /desc = "PCR primer"

( x i ) SEQUENCE DESCRIPTION: SEQ ID NO:33:

GCGGGATCCA CGCATCGATA CTGGTTAAAA                    30

( 2 ) INFORMATION FOR SEQ ID NO:34:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "PCR primer"

( x i ) SEQUENCE DESCRIPTION: SEQ ID NO:34:

GCGCCATGGG AAAAGAGGAG AAAGAGCTCA                    30

( 2 ) INFORMATION FOR SEQ ID NO:35:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "PCR primer"

( x i ) SEQUENCE DESCRIPTION: SEQ ID NO:35:

GCGAGATCTG ATACTCCAGA GGTATTACAA                    30

( 2 ) INFORMATION FOR SEQ ID NO:36:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "PCR primer"

( x i ) SEQUENCE DESCRIPTION: SEQ ID NO:36:

AATGCAGCTG GCACGACAGG                               20

( 2 ) INFORMATION FOR SEQ ID NO:37:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "PCR primer"

( x i ) SEQUENCE DESCRIPTION: SEQ ID NO:37:

GGTACCCGGG GATCCTCTAG                               20

( 2 ) INFORMATION FOR SEQ ID NO:38:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: other nucleic acid
    ( A ) DESCRIPTION: /desc = "PCR primer"

( x i ) SEQUENCE DESCRIPTION: SEQ ID NO:38:

TACCCGGGGA TCCTCTAGAG                          20

THERMOSTABLE MUTS PROTEINS

GOVERNMENT SUPPORT

This work was supported by Grant No. HG 00446 from the National Institutes of Health. The United States government has certain rights to this invention.

BACKGROUND OF THE INVENTION

The polymerase chain reaction (PCR) is one of the most important technologies for genome analysis. One of the weaknesses of PCR is a substantial rate of primer extension from mismatched primers, depending on the type of mismatch. Extension from mismatched primers limits allele-specific amplification and detection of mutations and polymorphisms to some extent with homogeneous DNA samples (e.g. for genotyping) but to a greater extent for heterogeneous DNA samples (e.g. for detection of cancer mutations). Another of the weaknesses of PCR is much poorer fidelity than observed during in vivo DNA replication, as reflected in (1) a rather high rate of nucleotide misincorporation, leading to difficulty in using PCR for faithful cloning and (2) the production of multiple bands when di- and trinucleotide repeats are amplified. An order of magnitude improvement in PCR specificity and fidelity could increase accuracy in genotyping and somatic mutation detection and open up new uses for PCR, including the reproducible and faithful cloning of genomic DNA fragments up to several kilobases in length. The present invention provides such an improvement in PCR.

The ligase chain reaction (LCR) and its variations (e.g., oligonucleotide ligation assay (OLA), ligase detection reaction (LDR)) are alternative techniques for genome analysis. A commonly recognized source of spurious background signal in LCR and its variations, as well as in PCR and its variations, is the hybridization of an oligonucleotide such as a probe or a primer, to regions of the nucleic acid not intended to be amplified. Generally, these hybridizations occur because the target sample contains, in addition to the target sequence itself, other sequences with some similarity to the target nucleic acid. Although hybridization of probe or primer to these similar sequences is not as probable as to the target sequence, some hybridization can occur. When such unintended non-specific hybridization occurs, it is possible that sequences other than the targeted sequence will be amplified. If these limitations of PCR and LCR could be reduced or eliminated, the methods would be even more useful than they presently are.

SUMMARY OF THE INVENTION

The invention relates to isolated nucleic acids which encodes a thermostable protein which binds specifically to bulge loops in a heteroduplex nucleic acid. As used herein, bulge loops include mispaired bases and frameshifts of 1–4 nucleotides or more. In one embodiment, the invention relates to nucleic acids which encode thermostable MutS proteins. Such nucleic acids include, for example, nucleic acids encoding *Aquifex pyrophilus* MutS, *Thermotoga maritima* MutS, *Thermus thermophilus* MutS, or *Thermus aquaticus* MutS and nucleic acids which hybridize to these nucleic acids. The invention further relates to recombinant constructs and vectors comprising nucleic acids encode *Aquifex pyrophilus* MutS, *Thermotoga maritima* MutS, *Thermus thermophilus* MutS, or *Thermus aquaticus* MutS or nucleic acids which hybridize thereto.

The invention also relates to proteins isolated from hyperthermophilic and thermophilic bacteria which bind specifically to bulge loops in a heteroduplex nucleic acid. As used herein, the phrase "isolated from" or "isolated nucleic acid" refers to nucleic acid obtained from (isolated from) naturally occurring sources as well as nucleic acids produced by recombinant methods or chemical synthesis, or by combinations of biological and chemical methods. Isolated nucleic acids produced by recombinant methods (e.g., genetic engineering methods) or synthesized chemically can also be referred to, respectively, as recombinantly produced nucleic acids and chemically synthesized or synthetic nucleic acids.

The invention further relates to isolated MutS proteins from hyperthermophilic or thermophilic bacteria. "Isolated" MutS proteins from hyperthermophilic or thermophilic bacteria include those obtained from naturally-occurring sources, as well as those produced by recombinant methods or chemical synthesis, or by combinations of biological and chemical methods.

The invention also relates to isolated thermostable proteins or polypeptides which bind specifically to bulge loops in a heteroduplex nucleic acid. Recombinant thermostable protein which binds specifically to bulge loops in a heteroduplex nucleic acid can be produced in host cells using cells and methods described herein.

Another embodiment of the invention relates to a method of reducing DNA misincorporation (i.e., improving fidelity of DNA replication) in an amplification reaction by including a thermostable protein which binds specifically to bulge loops in a heteroduplex nucleic acid in the reaction. The thermostable protein binds to bulge loops in a heteroduplex nucleic acid formed as a result of misincorporation of deoxynucleoside triphosphates during the amplification reaction. Binding of the thermostable protein prevents nucleic acids which include misincorporated deoxynucleoside triphosphates from acting as templates in subsequent rounds of the amplification reaction. Thus, amplification of nucleic acids which include misincorporated deoxynucleoside triphosphates is prevented, resulting in a reduction in overall DNA misincorporation.

A further embodiment of the present invention relates to an assay for detecting a target nucleic acid which includes a specific nucleic acid sequence. In the assay, an unextendable oligonucleotide which is completely complementary to a specific nucleic acid sequence of interest is combined with an amplification reaction mixture which comprises primers and nucleic acids to be assessed for the nucleic acid sequence of interest and a thermostable protein which binds specifically to bulge loops in a heteroduplex nucleic acid, to produce a test combination (i.e., the amplification reaction mixture, nucleic acid(s) to be assessed for the nucleic acid of interest, complementary oligonucleotides and the thermostable bulge loop-binding protein). The resulting test combination is maintained under conditions appropriate for nucleic acid amplification to occur (i.e., synthesis of product). The amount of product synthesized in the test combination is determined and compared with the amount of product synthesized in a corresponding control (the control amount) to determine if the specific nucleic acid sequence suspected of being present in the nucleic acids being assessed is present. If the amount of product synthesized in the test combination is the same as or less than the amount of product synthesized in the corresponding negative control, then the nucleic acids being assessed do not include the specific nucleic acid sequence. If the amount of product synthesized in the test combination is greater than the amount of product synthesized in the corresponding control, then the nucleic acids being assessed include the specific nucleic acid sequence. As used herein, the term "unextendable oligonucleotide" refers to an oligonucleotide which is modified at the 3' end to prevent it from functioning as a primer. For example, the oligonucleotide can be modified with a 3' phosphate to prevent it from functioning as a primer in the presence of Taq polymerase.

Another embodiment of the invention relating to detecting nucleic acid which includes a specific sequence of interest comprises (a) combining an amplification reaction mixture which comprises nucleic acids to be assessed for the nucleic acid sequence of interest, primer oligonucleotides, one of which is completely complementary to the specific nucleic acid sequence of interest, and a thermostable protein which binds specifically to bulge loops in a heteroduplex nucleic acid thereby producing a test combination; (b) maintaining the test combination of step (a) under conditions appropriate for amplification of nucleic acids to occur (i.e., synthesis of extension product); (c) determining the amount of extension products synthesized in the combination; and (d) comparing the amount of extension product determined in step (c) (i.e., the amount of extension product synthesized in the test combination) with the amount of product synthesized in a corresponding negative control, wherein if the amount of product synthesized in the test combination is the same as or less than the amount of product synthesized in the corresponding control, then the nucleic acids being assessed do not include the specific nucleic acid sequence.

Another embodiment of the invention relates to a method for amplifying a nucleic acid comprising a specific sequence of interest. The method comprises (a) combining an amplification reation mixture which comprises nucleic acids comprising the specific sequence of interest, oligonucleotides which are completely complementary to the specific nucleic acid sequence of interest and a thermostable protein which binds specifically to bulge loops in a heteroduplex nucleic acid, thereby producing a test combination; and (b) maintaining the test combination of step (a) under conditions appropriate for amplification of nucleic acids to occur, resulting in synthesis of the nucleic acid sequence of interest.

The invention also relates to a method for selecting against (i.e., reducing or preventing amplification of) a nucleic acid comprising a specific nucleic acid sequence of interest. The method comprises (a) combining an amplification reaction mixture which comprises nucleic acids to be amplified or detected and nucleic acids whose synthesis is to be prevented or reduced (nucleic acids to be selected against), oligonucleotides which form heteroduplexes with a strand of the nucleic acid being selected against, and a thermostable protein which binds specifically to bulge loops in a heteroduplex nucleic acid, thereby producing a test combination and (b) maintaining the test combination of step (a) under conditions appropriate for amplification of nucleic acids to occur. The thermostable protein binds heteroduplexes containing the nucleic acids to be selected against, preventing them from acting as templates in subsequent rounds of the amplification reaction and thereby selecting against a nucleic acid comprising the specific sequence.

The methods of the invention can further comprise including a stabilizer. As used herein, a stabilizer increases the lifetime of a thermostable bulge loop-binding protein-heteroduplex complex. A thermostable bulge loop-binding-heteroduplex complex is a complex formed when the thermostable protein is bound to a bulge loop in a heteroduplex nucleic acid. ATPγS is an example of a stabilizer.

Oligonucleotides which are designed so that they form heteroduplexes with a strand of the nucleic acid differ at one or more base pairs, at one or more sites, from the nucleic acid to be selected against. Oligonucleotides which are designed to be completely complementary to a specific nucleic acid sequence of interest or are designed to form heteroduplexes with a strand of the nucleic acid can be primers, blocking oligonucleotides or probes.

The invention further relates to an improvement in a method of amplification wherein the improvement comprises adding a thermostable protein which binds specifically to bulge loops in a heteroduplex nucleic acid to an amplification reaction mixture.

Amplification reactions include, for example, PCR and LCR. Thus, the amplification reaction mixture and amplification conditions will depend upon the particular amplification reaction being employed and can be determined from readily available sources.

BRIEF DESCRIPTION OF THE DRAWINGS

FIG. 1 depicts the DNA sequence (SEQ ID NO: 1) of the coding region of *Aquifex pyrophilus* (Apy) MutS.

FIG. 2 depicts the amino acid sequence (SEQ ID NO: 2) of *Aquifex pyrophilus* MutS.

FIG. 3 depicts the DNA sequence (SEQ ID NO: 4) of the coding region of *Thermotoga maritima* (Tma) MutS.

FIG. 4 depicts the amino acid sequence (SEQ ID NO: 5) of *Thermotoga maritima* MutS.

FIGS. 5A–5B depicts the amino acid sequences of *E. coli* MutS (SEQ ID NO: 3), *Aquifex pyrophilus* MutS (SEQ ID NO: 2) and *Thermotoga maritima* MutS (SEQ ID NO: 5), with (|) indicating identical amino acids and (:) indicating similar amino acids (TFASTA).

FIG. 6 depicts an analysis of the 5' and 3' untranslated regions of Tma MutS. Initiation: Double underlines indicate, in order, an in frame termination codon (TGA), a valine codon (GTN), a termination codon (TGA) for an upstream open reading frame (orf), the region of similarity to the 3' end of Tma 16S rRNA, and two additional valine codons. Termination: Double underlines indicate the antisense termination codon (TCA) for a downstream, antisense orf and the termination codon (TGA) for Tma MutS. Proteins with identical (|) or similar (:) amino acids (TFASTA) to the open reading frame are shown.

FIG. 7 depicts the partial DNA sequence (SEQ ID NO: 6) of the coding region of *Thermus thermophilus* MutS.

FIG. 8 depicts the partial DNA sequence (SEQ ID NO: 7) of the coding region of *Thermus aquaticus* MutS.

FIG. 9 depicts the alignment of partial amino acid sequences for the coding regions of *Aquifex pyrophilus* (Apy) MutS (SEQ ID NO: 2), *Thermus aquaticus* (Taq) MutS (SEQ ID NO: 8), *Thermus thermophilus* (Tth) MutS (SEQ ID NO: 9) and *Thermotoga maritima* (Tma) MutS (SEQ ID NO: 5). The numbers "613" and "595" correspond to amino acid position 613 in Apy MutS and amino acid position 595 in Tma MutS, respectively.

DETAILED DESCRIPTION OF THE INVENTION

Mismatch correction in prokaryotic and eukaryotic species may be initiated by the mismatch binding of a homolog of the product of one of several *E. coli* mutator genes, mutS. In *E. coli*, mismatch correction also requires MutL, the endonucleolytic activity of MutH, and the activities of several additional enzymes (Modrich, P., *Annu. Rev. Genet.* 25: 229–253 (1991); Modrich, P., *Science* 266: 1959–1960

(1994)). Insertions into mutS lead to a high frequency of spontaneous mutation which may easily be detected as an increased frequency of streptomycin resistant cells (Siegel, E. C. et al., *Mutat. Res.* 93: 25–33 (1982)). The MutHSL system selectively removes mismatches from daughter strands following incorrect incorporation of nucleotides during DNA replication (Au, K. G. et al., *J. Biol. Chem.* 267: 12142–12148 (1992)). In *E. coli*, GATC sites are methylated by the dam methylase. Hemimethylation at GATC permits differentiation of template from daughter strands. The repair of a mismatch is bidirectional with respect to the hemimethylated site (Cooper, D. L. et al., *J. Biol. Chem.* 268: 11823–11829 (1993)). In addition, the same mismatch correction system is responsible for removing frameshifts of up to four nucleotides which may be the result of the presence of an intercalating agent during DNA replication (Rene, B. et al., *Mutat. Res.* 193: 269–273 (1988)) or of polymerase slippage at di- or tri-nucleotide repeats (Parker, B. O. and Marinus, M. G., *Proc. Natl. Acad. Sci. USA* 89: 1730–1734 (1992)). Transition and frameshift mutations are increased about 275- and 1500-fold, respectively, in mutS⁻ *E. coli* cells (Schaaper, R. M. and Dunn, R. L., *Genetics* 129: 317–326 (1991)).

In man, the mutS homolog (MSH2) is a mutator gene involved in hereditary nonpolyposis colorectal cancer (Leach, F. S. et al., *Cell* 75: 1215–1225 (1993); Fishel, R. et al., *Cell* 75: 1027–1038 (1993)). These cells must have escaped from the requirement for completion of DNA repair prior to entry into S phase. Cells deficient in MutS homolog-dependent mismatch repair fail to accumulate single-strand breaks and are resistant to killing by alkylating agents (Branch, P. et al., *Nature* 362: 652–654 (1993)), suggesting that in wild-type cells, introduction of alkylated sites reactivates mismatch repair and that MutS homologs find target sites, whether they be mismatches or other small lesions. In fact, the replication of alkylated DNA in mutS⁻ *E. coli* cells may contribute to the hypermutation phenotype.

Purified *E. coli* MutS protein binds specifically to oligonucleotide heteroduplexes (Su, S.-S. and Modrich, P., *Proc. Natl. Acad. Sci. USA* 83: 5057–5061 (1985)). Gel-shift assays may be carried-out with *E. coli* MutS protein and a heteroduplex with a GT mismatch (less efficiently an AC mismatch) (Jiricny, J. et al., *Nucleic Acids Res.* 16: 7843–7853 (1988)) or a 3-nucleotide bulge loop (Lishanski, A. et al., *Proc. Natl. Acad. Sci. USA* 91: 2674–2678 (1994)) to detect MutS protein binding. *E. coli* MutS protein also binds specifically to heteroduplexes containing IC mismatches (Jiricny, J. et al., *Nucleic Acids Res.* 16: 7843–7853 (1988)). Human MSH2 also binds to GT mismatches (Fishel, R. et al., *Cancer Res.* 54: 21 (1994)). However, binding to bulge loops is not limited to 1–4 nucleotides but occurs with loops as large as 14 nucleotides in length (Fishel, R. et al., *Science* 266: 1403–1405 (1994)). The binding of *E. coli* MutS protein to mismatches is sufficiently strong that it will block RecA-mediated strand displacement reactions (Worth, L., Jr. et al., *Proc. Natl. Acad. Sci. USA* 91: 3238–3241 (1994)) and the exonuclease activity of T7 DNA polymerase (Ellis, L. A. et al., *Nucleic Acids Res.* 22: 2710–2711 (1994)).

Applicant has cloned and expressed thermostable MutS proteins from hyperthermophilic eubacteria and demonstrated specific binding of the thermostable MutS proteins to bulge loops in a heteroduplex nucleic acid. Until Applicant's cloning and isolation of thermostable MutS proteins, all of the studies of MutS and MutS-homolog proteins have involved proteins from mesophilic organisms.

As used herein, the term "thermostable protein" refers to protein of thermophilic bacterial origin or hyperthermophilic bacterial origin. Such thermostable proteins can be obtained from an organism in which they occur in nature, can be produced by recombinant methods or can be synthesized chemically.

As used herein, the terms "heteroduplex nucleic acid" and "heteroduplex" refer to a double-stranded nucleic acid which is formed by a mismatch (e.g., C–A or G–T nucleotide pairs as opposed to the naturally-occurring C–G or A–T nucleotide pairs or frameshifts of 1–4 nucleotides or more) between complementary strands. As used herein, the terms "homoduplex nucleic acid" and "homoduplex" refer to a double-stranded nucleic acid which is formed by perfectly matched complementary strands. As defined herein, a bulge loop is a distortion in double-stranded nucleic acids. A bulge loop arises as a result of, for example, a frameshift or a mispairing between strands in a limited region, i.e., a mismatch between complementary strands, and comprises a mismatch of at least a single nucleotide pair.

Nucleic Acids, Constructs and Vectors

The present invention relates to isolated nucleic acids which encode a thermostable protein which binds specifically to bulge loops in a heteroduplex nucleic acid. In one embodiment, the nucleic acid encodes a thermostable protein which binds specifically to bulge loops in a heteroduplex nucleic acid. The present invention also relates more specifically to isolated nucleic acids which encode a thermostable MutS protein from hyperthermophilic or thermophilic bacteria. The present invention further relates to isolated nucleic acids which encode a thermostable MutS protein from *Aquifex pyrophilus* and isolated nucleic acids which encode a thermostable MutS protein from *Thermotoga maritima*. The present invention also relates to isolated nucleic acids which encode a thermostable MutS protein from *Thermus thermophilus* and isolated nucleic acids which encode a thermostable MutS protein from *Thermus aquaticus*.

The invention also relates to isolated nucleic acids which (1) hybridize to (a) a nucleic acid encoding a thermostable MutS protein specific for a selected amino acid, such as a nucleic acid having the sequence of FIG. 1 (SEQ ID NO: 1), FIG. 3 (SEQ ID NO: 4), FIG. 7 (SEQ ID NO: 6) or FIG. 8 (SEQ ID NO: 7), (b) the complement of any one of (a), or (c) portions of either of the foregoing (e.g., a portion comprising the open reading frame); (2) encode a polypeptide having the amino acid sequence of a thermostable MutS protein (e.g., SEQ ID NO: 2 or SEQ ID NO: 5), or functional equivalents thereof (e.g., a thermostable polypeptide which binds specifically to bulge loops in a heteroduplex nucleic acid with a selected amino acid); or (3) have both characteristics. Portions of the isolated nucleic acids which code for polypeptides having a certain function can be identified and isolated by, for example, the method of Jasin, M., et al., U.S. Pat. No. 4,952,501.

Nucleic acids meeting these criteria comprise nucleic acids having sequences identical to sequences of naturally occurring thermostable MutS proteins from *Aquifex pyrophilus, Thermotoga maritima, Thermus thermophilus* or *Thermus aquaticus*, or variants of the naturally occurring sequences. Such variants include mutants differing from naturally occurring sequences by the addition, deletion or substitution of one or more residues, modified nucleic acids in which one or more residues are modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are set forth on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity.

Isolated nucleic acids that are characterized by their ability to hybridize to (a) a nucleic acid encoding a thermostable MutS protein (for example, those nucleic acids depicted in FIG. 1 (SEQ ID NO: 1), FIG. 3 (SEQ ID NO: 4), FIG. 7 (SEQ ID NO: 6) and FIG. 8 (SEQ ID NO: 7), (b) the complement of such nucleic acids, (c) or a portion thereof (e.g. under high or moderate stringency conditions), and which encode a thermostable protein or polypeptide which binds a bulge loop in a heteroduplex nucleic acid are also the subject of this invention. The binding function of a protein or polypeptide encoded by hybridizing nucleic acid may be detected by standard assays for binding (e.g., mismatch binding assays which demonstrate binding of the protein or polypeptide to a bulge loop in a heteroduplex nucleic acid such as, for example, gel shift assays). Functions characteristic of the thermostable MutS protein may also be assessed by in vivo complementation tests or other suitable methods. Mismatch binding assays, complementation tests, or other suitable methods can also be used in procedures for the identification and/or isolation of nucleic acids which encode a polypeptide such as a polypeptide of the amino acid sequence SEQ ID NO: 2 or SEQ ID NO: 5, or functional equivalents of these polypeptides. The antigenic properties of proteins or polypeptides encoded by hybridizing nucleic acids can be determined by immunological methods employing antibodies that also bind to a naturally-occurring thermostable MutS protein. These methods can include immunoblot, immunoprecipitation and radioimmunoassay.

Nucleic acids of the present invention can be used in the production of proteins or polypeptides. For example, DNA encoding a thermostable MutS protein, such as a thermostable MutS from *Aquifex pyrophilus*, or DNA which hybridizes to DNA having the sequence SEQ ID NO: 1, can be incorporated into various constructs and vectors created for further manipulation of sequences or for production of the encoded polypeptide in suitable host cells. Similarly, DNA containing all or part of the coding sequence for a thermostable MutS protein, such as a thermostable MutS from *Thermotoga maritima*, or DNA which hybridizes to DNA having the sequence SEQ ID NO: 4, can be incorporated into various constructs and vectors created for further manipulation of sequences or for production of the encoded polypeptide in suitable host cells. For expression in *E. coli* and other organisms, a GTG initiation codon can be altered to ATG as appropriate.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

MutS proteins from hyperthermophiles such as *Aquifex pyrophilus* and *Thermotoga maritima* can be used in methods for allele-specific amplification and in methods for enhancing amplification reactions because they are stable to heat, are heat resistant and do not become irreversibly denatured (inactivated) when subjected to the elevated temperatures for the length of time necessary for the denaturation and annealing steps of amplification techniques such as the polymerase chain reaction and its variations or the ligase chain reaction and its variations.

As described in the Examples, MutS genes were cloned into *E coli* from two distantly-related hyperthermophilic eubacteria, *Aquifex pyrophilus* (Apy) and *Thermotoga maritima* (Tma). All cloning was carried out using PCR technology without the need for library construction. Inverse PCR is a rapid method for obtaining sequence data for the 5'- and 3'-flanking regions of bacterial genes, the prerequisite for generation of primers for PCR cloning into an expression vector. Because of the inherent error frequency of in vitro DNA replication, care was taken to demonstrate that sequences of independently-derived expression clones were identical. A MutS protein from each species was expressed and purified to homogeneity. The proteins were thermoresistent to $\geq 90°$ C. and specifically bound to DNA duplexes containing mismatched bases.

The approaches described herein, including, but not limited to, the approaches to isolate and manipulate the MutS genes of *Aquifex pyrophilus* and *Thermotoga maritima*, to construct vectors and host strains, and to produce and use the proteins, to produce antibodies, etc., can be applied to other members of the genus Aquifex or other members of the genus Thermotoga. For example, the Apy MutS gene described here, or sufficient portions thereof, including fragments produced by PCR, can be used as probes or primers to detect and/or recover homologous genes of the other Aquifex species (e.g., by hybridization, PCR or other suitable techniques). Similarly, genes encoding Apy MutS protein can be isolated from genomic libraries according to methods described herein or other suitable methods. The Tma MutS gene described here, or sufficient portions thereof, including fragments produced by PCR, can be used as probes or primers to detect and/or recover homologous genes of the other Thermotoga species (e.g., by hybridization, PCR or other suitable techniques). Similarly, genes encoding Tma MutS protein can be isolated from genomic libraries according to methods described herein or other suitable methods.

The approaches described herein, including, but not limited to, the approaches to isolate and manipulate the MutS genes of *Aquifex pyrophilus* and *Thermotoga maritima*, to construct vectors and host strains, and to produce and use the proteins, to produce antibodies, etc., can also be applied to other hyperthermophilic bacteria and to thermophilic bacteria. Hyperthermophilic bacteria include species of the archaebacteria, which include the most hyperthermophilic species known. Hyperthermophilic archaebacteria include members of the genus Pyrodictium, including, but not limited to, *Pyrodictium abyssi* (Pab) and *Pyrodictium occultum* (Poc). Thermophilic bacteria include members of the genus Thermus, including, but not limited to, *Thermus aquaticus* (Taq) and *Thermus thermophilus* (Tth). Thermophilic bacteria also include hyperthermophilic bacteria. As used herein, the "thermophilic bacteria" is meant to include hyperthermophilic and thermophilic bacteria.

For example, application of the degenerate primers described in the Examples for Apy and Tma mutS fragment cloning to genomic DNA from the thermophilic eubacteria *Thermus aquaticus* (Taq) and *Thermus thermophilus* (Tth), both from the American Type Culture Collection, led to the cloning and sequencing of Taq- and Tth-specific MutS sequences. The origin of these sequences was verified by Southern hybridization. The Taq and Tth MutS proteins can be evaluated for their ability to bind specifically to bulge loops in a heteroduplex nucleic acid using methods described herein for evaluating the ability of the Apy and Tma MutS proteins to bind specifically to bulge loops in a heteroduplex nucleic acid (e.g., gel shift binding assays).

Hyperthermophilic archaebacteria *Pyrodictium abyssi* and *Pyrodictium occultum*, both from cells supplied by Professor Karl Stetter, Universität Regensburg, can be used as templates for degenerate priming. Once Pab and Poc fragment sequences have been found which encode an amino acid sequence similar to other MutS proteins, unique inverse primers can be synthesized and tested by Southern hybridization to verify that these sequences originated from Pab and Poc genomic DNAs.

The 5' coding and 3' downstream noncoding sequences for Pab, Poc, Taq and Tth mutS can be obtained by inverse PCR walking. The 5' coding sequence can be verified by cycle sequencing. These coding sequences can be used to design expression primers. Independently-derived PCR products resulting from each pair of expression primers can be ligated into one or more expression plasmids, including pDG160/pDG182/pDG184 and/or the pET series from Novagen, Inc., and electroporated into the appropriate hosts. Plasmids from several clones expressing each thermostable MutS can be sequenced.

The PCR amplifications of Pab, Poc, Taq and Tth genomic DNAs can be carried out in 50–100 $\mu$l containing 1 $\mu$M of each primer, 10 mM Tris buffer, pH 8.3, 50 mM KCl, 25–50 units/ml Taq DNA polymerase, and 200 $\mu$M of each dNTP (Saiki, R. K. et al., *Science* 239: 487–491 (1988)). Simultaneous reactions can be initiated by addition of a MgCl$_2$ solution to Mg$^{++}$-free PCR mixtures at >80° C. to yield final concentrations of 0.8–2 mM followed by denaturation for 30 sec at 95° C.

When using degenerate primers and 50 ng of a genomic DNA template, the first S cycles will employ a 30 second annealing step at 45° C. followed by a 2 minute ramp to 72° C. before denaturation. An additional 30–35 cycles can be carried out with a 55° C. annealing temperature. For inverse PCR (Ochman, H. et al., In PCR Protocols. A Guide to Methods and Applications, Innis, M. A. et al., Eds. (San Diego: Academic Press, Inc) pp. 219–227 (1990)), genomic DNA can be digested to completion with a restriction endonuclease leaving a 3' or 5' 4-base overhang, phenol extracted, and ligated overnight at a DNA concentration of less than 50 $\mu$g/ml. When using unique direct or inverse PCR primers, 50 ng of genomic or circularized genomic DNA template, respectively, can be employed, and the first 5 cycles omitted.

Thermostable protein mixtures from bacteria expressing Pab, Poc, Taq and Tth MutS can be prepared and purified as described in the Examples pertaining to the preparation and purification of Apy and Tma MutS. Initially, these mixtures can be diluted to give 1.5M (NH$_4$)$_2$SO$_4$, 20 mM sodium phosphate, pH 7.0, loaded on the BU column, washed with the same buffer, and eluted with a linear gradient to 20 mM sodium phosphate, pH 7.0, 10% ethylene glycol. The elution conditions can then be optimized for each protein. The proteins can be concentrated, and the solvent can be changed by dialysis. The final products can be analyzed for purity by SDS-PAGE. Protein concentrations can be determined using the Bio-Rad Protein Assay kit (Bradford) and by analysis of complete absorbance spectra, which will document removal of nucleic acids.

These purified MutS proteins can be evaluated for the ability to bind specifically to bulge loops in a heteroduplex nucleic acid using the methods as described herein in evaluating the ability of the Apy and Tma MutS proteins to bind to a bulge loop in a heteroduplex nucleic acid (see, e.g., gel shift assays).

Proteins

The invention also relates to thermostable nucleic acid binding proteins or polypeptides encoded by nucleic acids of the present invention. As used herein, "thermostable proteins or polypeptides" are proteins, polypeptides or protein fragments which are stable to heat, have heat resistant nucleic acid binding activity and do not become irreversibly denatured (inactivated) when subjected to the elevated temperatures for the time periods necessary, for example, for PCR amplification. Thermostable proteins are also proteins of thermophilic bacterial origin or hyperthermophilic bacterial origin. Such proteins can be obtained from (isolated from) an organism in which they occur in nature, can be produced by recombinant methods or can be synthesized chemically.

The thermostable proteins described herein are thermoresistant to $\geq 90°$ C. The thermostable proteins are known to bind specifically to bulge loops in a heteroduplex nucleic acid at temperatures of from about room temperature to about 100° C. However, specificity of binding to bulge loops is greatest at the high end of this temperature range. With decreasing temperature from about 100° C., an increasing proportion of protein is found to bind nonspecifically to nucleic acids forming perfect homoduplexes.

The thermostable proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, including essentially pure proteins or polypeptides, proteins or polypeptides produced by chemical synthesis, by recombinant methods, or by combinations of biological and chemical methods, and recombinant proteins or polypeptides which are isolated. Proteins or polypeptides referred to herein as "recombinant" or "recombinantly produced" are proteins or polypeptides produced by the expression of recombinant nucleic acids.

In one embodiment, the thermostable nucleic acid binding protein binds a bulge loop in a heteroduplex nucleic acid. These thermostable proteins include, for example, naturally occurring thermostable MutS proteins from *Aquifex pyrophilus, Thermotoga maritima, Thermus thermophilus* and *Thermus aquaticus*, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

In another embodiment, like naturally occurring thermostable MutS proteins from *Aquifex pyrophilus, Thermotoga maritima, Thermus thermophilus* or *Thermus aquaticus*, isolated and/or recombinant thermostable MutS proteins of the present invention bind specifically to bulge loops in heteroduplex nucleic acids. For example, in the case of *Aquifex pyrophilus*, an isolated, recombinant thermostable MutS binds specifically to bulge loops in a heteroduplex nucleic acid.

The invention further relates to fusion proteins, comprising a thermostable MutS protein (as described above) as a first moiety, linked to second moiety not occurring in the thermostable MutS protein as found in nature. The second moiety can be an amino acid or polypeptide. The first moiety can be in an N-terminal location, C-terminal location or internal to the fusion protein. In one embodiment, the fusion protein comprises a thermostable MutS protein of *Aquifex pyrophilus* origin as the first moiety, and a second moiety comprising a linker sequence and affinity ligand.

Fusion proteins can be produced by a variety of methods. For example, a fusion protein can be produced by the insertion of an thermostable MutS gene or portion thereof into a suitable expression vector, such as Bluescript SK+/− (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)).

Method of Producing Recombinant Thermostable MutS Proteins

Another aspect of the invention relates to a method of producing a thermostable MutS protein, and to expression systems and host cells containing a vector appropriate for expression of a thermostable MutS protein.

Cells that express a recombinant thermostable MutS protein can be made and maintained in culture to produce protein for isolation and purification. These cells can be procaryotic or eucaryotic. Examples of procaryotic cells that can be used to express thermostable MutS proteins include *Escherichia coli, Bacillus subtilis* and other bacteria. Examples of eucaryotic cells that can be used to express the thermostable MutS protein include yeasts such as *Saccharomyces cerevisiae, S. pombe, Pichia pastoris*, and other lower eucaryotic cells, as well as cells of higher eucaryotes, such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a thermostable MutS protein for isolation and purification, as a first step the gene encoding the MutS protein can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for thermostable MutS protein operably linked to one or more expression control sequences whereby the coding sequence is under the control of transcription signals and linked to appropriate translation signals to permit translation of the thermostable MutS protein or of a fusion protein comprising a thermostable MutS protein. As a second step, the vector can be introduced into cells by a method appropriate to the type of host cells (e.g., transformation, transfection, electroporation, infection). In a third step, for expression from the thermostable MutS gene, the host cells can be maintained under appropriate conditions (e.g., in the presence of inducer, normal growth conditions) for expresiion of the gene and production of the encoded MutS protein.

As a particular example of the above approach to producing active thermostable MutS protein, a gene encoding the *Aquifex pyrophilus* MutS can be integrated into the genome of a virus that enters host cells. By infection of the host cells, the components of a system which permits the transcription and translation of the *Aquifex pyrophilus* MutS gene are introduced into the host cells, in which expression of the encoded product occurs. Alternatively, an RNA polymerase gene, inducer, or other component required to complete such a gene expression system may be introduced into the host cells already containing the *Aquifex pyrophilus* MutS gene, for example, by means of a virus that enters the host cells and contains the required component. The thermostable MutS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Reducing Misincorporation

The present invention further relates to methods of reducing DNA misincorporation (i.e., improving fidelity of DNA replication) in an amplification reaction.

Replication errors are frequent with all thermostable polymerases, even using the optimum conditions (Eckert, K. A. and Kunkel, T. A., *PCR. Methods. Appl.* 1: 17–24 (1991); Ling, L. L. et al., *PCR. Methods. Appl.* 1: 63–69 (1991)). Comparing optimal conditions, the 3'→5' editing exonuclease activity of a polymerase will decrease PCR errors by no more than 2–5 fold. The majority of errors introduced during PCR amplification are transitions (Keohavong, P. et al., *PCR. Methods. Appl.* 2: 222–292 (1993)). Improvement of fidelity depends upon the ability of MutS to bind heteroduplexes tightly and provide a nucleus for renaturation following the strand-separation step of PCR.

Fidelity with and without Apy or Tma MutS can be assayed by determining the frequency of mutations introduced during amplification of lacI$^q$ which prevent expression of a functional lac repressor protein and by determining the extent of frameshift mutation ("stuttering"/"slippage") during amplification of di- and trinucleotide repeats. Compatibility between high fidelity amplification conditions and long PCR conditions (Cheng, S. et al., *Proc. Natl. Acad. Sci. USA* 91: 5695–5699 (1994)) is considered.

Mutation or Polymorphism Detection

Genome mismatch scanning (GMS) (Brown, P. O., *Current Opinion in Genetics & Development* 4: 366–73 (1994)), a method for whole genome scanning which utilizes *E. coli* MutS and the other enzymes of the mismatch repair system, is one of the new methods being developed for mapping and/or cloning genes based on sequence differences or similarities in two DNA pools (Jonsson, J. J. and Weissman, S. M., *Proc. Natl. Acad. Sci. USA* 92: 83–95 (1995)). Several methods have been developed for scanning the specific DNA sequences of a known gene for mutations or polymorphisms, including single-strand conformation polymorphism analysis (SSCP) (reviewed by Hayashi, K. and Yandell, D. W., *Human Mutation* 2: 338–46 (1993)), which does not require heteroduplex formation, and chemical and, most recently, endonuclease VII-based cleavage methods, which require heteroduplex formation (Youil, R. et al., *Proc. Natl. Acad. Sci. USA* 92: 87–91 (1995)).

Several methods are available for identification of specific alleles in those instances where the mutation or polymorphism is known. The problem is relatively straightforward for mapping germline genes, somewhat more difficult for detecting cancer-related mutations in tumors with mixed cell populations and quite difficult for screening lymph nodes or other sources (e.g. sputum) for cancer-related mutations. There are comparable problems in the analysis of mutations in pathogens. The methods for identification of specific alleles include allele-specific PCR (Kwok, S. et al., *Nucleic Acids Res.* 18: 999–1005 (1990); Tada, M. et al., *Cancer Res.* 53: 2472–2474 (1993); Bottema, C. D. et al., *Methods Enzymol.* 218: 388–402 (1993)), allele-specific ligase chain reaction (LCR) (Wiedmann, M. et al., *PCR Methods & Applications* 3: S51–64 (1994)), RFLP/PCR (Felley-Bosco, E. et al., *Nucleic Acids Res.* 19: 2913–2919 (1991); Cha, R. S. et al., *PCR. Methods. Appl.* 2: 14–20 (1992)), which requires a restriction endonuclease cleavage site in one allele, and combination methods (Hruban, R. H. et al., *Am. J. Pathol.* 143: 545–554 (1993)). Mismatch-specific single-strand cleavage including MutY (Hsu, I.-C. et al., *Carcinogenesis* 15: 1657–1662 (1994)) coupled with ligase-mediated PCR (LMPCR) has permitted detection of certain human p53 mutations at a sensitivity of about 1%. The most complicated and least general methods, such as RFLP-PCR, need to be employed whenever the mutation is present in a small fraction of the templates (<1%).

The present invention relates to methods for enhancing allele-specificity, especially for transition and small frame-shift mutations. The present invention more specifically relates to inclusion of Apy and/or Tma MutS protein in a PCR reaction. A simple assay would be more amenable to automation using highly-parallel "classical" or chip-based amplification technologies.

In one embodiment, Apy MutS or Tma MutS bind specifically to a heteroduplex primer-template complex containing a GT transition mismatch (for every AC mismatch there is a GT mismatch) or a small bulge loop and not to a perfectly matched primer, thus interfering with initiation of polymerization from the mismatched template.

Allele-specific primers forming a GT mismatch can be synthesized, although the MutS proteins of the present invention can bind to other types of heteroduplexes. Of greater importance, any selection against primer-template mismatches throughout the length of a primer-template complex should translate into fewer improper extension products for all PCR reactions.

In another embodiment, a MutS-oligonucleotide heteroduplex complex is formed between the primers, thus blocking DNA polymerization during each PCR cycle. This embodiment should provide the highest level of allele specificity.

Isolated, recombinant thermostable MutS protein or a portion thereof, and suitable fusion proteins can be used in methods for enhancing allele-specificity (i.e, in methods for detecting mismatches formed between heteroduplex template-oligonucleotide nucleic acids).

The present invention also relates to methods for selecting against amplification of mismatches between complementary strands. That is, the present invention also relates to methods for selecting against amplification of heteroduplex nucleic acid.

Studies of Heteroduplex Binding and Detection

Many of the DNA manipulations described herein involve standard techniques and procedures (Sambrook, J. et al., *Molecular Cloning, A Laboratory Manual*, 2nd edition, Cold Spring Harbor: Cold Spring Harbor University Press (1989)).

As described herein, the mismatch binding assay (also referred to herein as the gel shift binding assay or the gel shift assay) was used to evaluate the MutS proteins of the present invention for specific binding to bulge loops in a heteroduplex nucleic acid.

As described in the Examples, to make heteroduplex substrates for use in evaluating the MutS proteins of the present invention for specific binding to bulge loops in a heteroduplex nucleic acid, several modifications were introduced into pUC19 by replacing the KpnI to PstI segment of the polylinker. In pUC19GC, the BamHI site GGATCC in the sequence GGGGATCCTC (SEQ ID NO: 10) was modified to substitute a C for the first T to yield GGGACCCTC (SEQ ID NO: 11). The resultant plasmid gained an AvaII site. In pUC19Δ1, a T was inserted into the pUC19GC polylinker sequence GGGACCCTC to yield GGGGATCCCTC (SEQ ID NO: 12) and reconstitute the BamHI site. In pUC19Δ3, a T and two Cs were inserted into the pUC19GC polylinker sequence GGGACCCTC to yield GGGGATCCCCTC (SEQ ID NO: 13) and again reconstitute the BamHI site. The sequences were verified.

PCR products of 337–340 bp were synthesized from the pUC19, pUC19GC, pUC19Δ1 and pUC19Δ3 using 5' TACGCCAGCTGGCGAAAGGG 3' (SEQ ID NO: 14) and 5' AATGCAGCTGGCACGACAGG 3' (SEQ ID NO: 15), where the PvuII sites are underlined. PCR products up to 2.7 kb can be prepared using appropriate primers. For some experiments, one of the primers was labeled with $^{32}$P using T4 polynucleotide kinase to allow quantitation of products.

Heteroduplexes were formed in PCR and similar buffers from various ratios of two different PCR products by denaturation at about 97° C. and annealing at about 67° C. (Wetmur, J. G., *Crit. Rev. Biochem. Mol. Biol.* 26, 227–259 (1991)). Heteroduplexes between pUC19GC (or pUC19) and pUC19Δ3 were easily separated from homoduplexes on a 6% polyacrylamide gel. Heteroduplexes between pUC19Δ1 and pUC19Δ3 were less separated from homoduplexes, having a loop size of two rather than three, but were easily distinguished. Heteroduplexes between pUC19GC (or pUC19) and pUC19Δ1, as well as heteroduplexes between pUC19 and pUC19GC, could not be distinguished from homoduplexes using this gel system.

In particular, the homoduplexes, differing by only 3 base pairs, had almost identical mobilities. The heteroduplexes had reduced mobility. Denaturation and fast cooling prevented complete renaturation and revealed a slower-moving denatured DNA band. Addition of Apy MutS protein led to a gel shift of the heteroduplex band and appearance of a new band for the complex. Denaturation and fast cooling in the presence of the thermostable Apy MutS demonstrated that the specific binding to the heteroduplex was preserved.

Heteroduplexes were formed between pUC19GC prepared with one labeled primer and pUC19Δ1 or pUC19 using excess pUC19Δ1 or pUC19, so that most of the label is in heteroduplex and not homoduplex. AvaII cleavage was tested for the ability to deplete residual homoduplexes without affecting the heteroduplexes.

Heteroduplexes were also formed by reversing the choice of labeled PCR product and renaturation driver. BamHI cleavage can similarly be tested for the ability to deplete residual homoduplexes without affecting the heteroduplexes. Labeled heteroduplexes were also formed using pUC19GC and pUC19Δ3.

With pUC19 plus pUC19GC heteroduplexes, GT and AC mismatches were created simultaneously. Hybridization of the plus strand of pUC19GC with the complementary strand of pUC19 DNA leads to an AC mismatch, whereas hybridization of the plus strand of pUC19 with the complementary strand of pUC19GC DNA leads to a GT mismatch. Heteroduplex formation between pUC19Δ1 and pUC19GC leads to molecules with unpaired A or T residues. Heteroduplex formation between pUC19Δ3 and pUC19GC leads to molecules with three unpaired GGA or TCC residues. These mismatches were evaluated independently by the choice of radiolabeled primer, using the gel shift assay.

MutS binding assays employed a 1:20 dilution of each of the heteroduplex mixtures or homoduplex controls containing approximately 5 μg/ml total DNA in PCR buffer added into 20 mM Tris, pH 7.5, 5 mM $MgCl_2$, 0.1 mM DTT, 0.01 mM EDTA. Apy MutS protein purified to homogeneity was used in the assays. However, using the MutS binding assays described, any protein purified to homogeneity can be evaluated for specific binding to bulge loops in a heteroduplex nucleic acid.

After incubation in the presence or absence of MutS protein, the products were separated by electrophoresis at 25 V/cm for 30 min on a 6% polyacrylamide gel at 4° C. in 0.2× TBE and analyzed by ethidium bromide staining and UV fluorography or autoradiography.

The temperature, pH, added KCl, and added $Mg^{++}$ in the loading and running buffers of the gel shift assay can be adjusted to provide for a set of standard assay conditions where specific binding to bulge loops of the MutS proteins to be evaluated is not affected by the assay conditions. For the assay conditions to have no effect, MutS exchange must not take place. To determine the assay conditions most permissive of sample variability, identical measurements can be carried out with and without unlabeled native DNA and/or heteroduplexes added to the loading buffer.

To investigate thermostability of Apy MutS, Tma MutS, and other MutS proteins, after incubation at constant temperature in PCR buffer, aliquots of the MutS proteins were removed as a function of time and tested for binding activity in the standard assay.

One variable in MutS binding is stoichiometry of MutS to heteroduplex DNA. Thus, to investigate specificity of MutS binding to the set of heteroduplexes, addition of competing ssDNA-free native superhelical or linear dsDNA, or ssDNA, were used as an assay for non-specific binding. The linear dsDNA can be varied in size to test for end effects. Other variables include incubation temperature and time, pH, KCl and $Mg^{++}$ concentrations.

MutS proteins all contain a Walker motif, GxxxxGKS, which has been implicated in NTP binding. Inclusion of 0.1 mM ATP in the Apy MutS binding assay to a 3 nucleotide loop had no effect on the binding stoichiometry.

To investigate thermostability of each of the complexes formed between Apy MutS and Tma MutS with the set of radiolabeled heteroduplexes, after complex formation, unlabeled PCR product identical to the labeled PCR product used for heteroduplex formation can be added to restore 1:1 stoichiometry. After incubation at a particular temperature, renaturation to completion and deproteinization, the fraction of newly-formed unlabeled heteroduplex, up to 50% of the total DNA, will reflect homoduplex strand separation, and the fraction of newly-formed labeled homoduplex, up to 50% of the labeled DNA, will reflect MutS-heteroduplex complex strand separation. The relative strand-separation temperatures of heteroduplex complexes and uncomplexed homoduplexes in conditions compatible with PCR can thus be determined.

Kinetics of Heteroduplex Binding

The reverse rate (dissociation rate) can be determined by measuring the rate of exchange of a MutS-radiolabeled heteroduplex complex with a competing unlabeled heteroduplex using a variety of solvent conditions. The pUC19-pUC19Δ3 heteroduplexes are sufficiently stable to permit gel-shift analysis and can be used as the unlabeled heteroduplex for investigating the complete set of radiolabeled heteroduplexes. To determine whether exchange requires MutS dissociation from the labeled heteroduplex before binding to competing DNA, the effects of the concentrations of specific competing heteroduplex or non-specific competing native DNA were determined. Thus, the optimum conditions favoring heteroduplex stability consistent with specificity and PCR can be found.

The forward rate (binding rate) can be determined using a variety of solvent conditions where the dissociation rate is slow. Binding can be terminated as a function of time by adding competing DNA, and the fraction of labeled heteroduplex complexed to MutS can be determined. The forward rate constant for MutS binding to a mismatch cannot be greater than approximately $2\times10^8$ $M^{-1}s^{-1}$, the diffusion control limit, unless binding is mediated through exchange from non-specific binding sites. The half-time for the diffusion controlled reaction would be approximately 0.6 sec at 12.5 nM target each of heteroduplex (e.g. 50% of 100 ng/20 μl) and MutS (50 ng/20 μl). Lower concentrations permit determination of binding rate constants. Thus, the MutS concentration necessary for specific, stable and rapid mismatch binding in conditions compatible with PCR can be found.

Nuclease Protection Assays

Footprints of Apy and MutS binding to the set of radiolabeled heteroduplexes can be determined by electrophoresis on a sequencing gel following limited endonuclease digestion of heteroduplexes labeled first at one end and then at the other. Footprinting can also be attempted using the 5'→3' exonuclease activity of thermostable Taq DNA polymerase and the 3'→5' exonuclease activity of thermostable Vent DNA polymerase in a manner akin to the use of the 3'→5' exonuclease activity of T7 DNA polymerase with *E. coli* MutS (Ellis, L. A. et al., *Nucleic Acids Res.* 22: 2710–2711 (1994)).

Other Mismatches

Transitions and small frameshifts are the mutations known to be the most effective MutS substrates. However, transversion mutations can be effective MutS substrates. Optimal conditions for binding of MutS proteins to TC, CC, TT, GA, GG and AA mismatches can be tested after the design and production of additional PCR templates.

Allele-Specific Amplification With Matched Primers

Allele-specific amplification with matched primers demonstrates that MutS binding to a variety of mismatched primer-template complexes inhibits initiation of polymerization.

In one embodiment of allele-specific amplification with mismatched primers, the PCR template is a mixture containing one of the pUC19 derivatives described previously (especially pUC19GC and pUC19Δ1) and pMS19, a derivative of pUC19 with inserts of 35 bp at both the EcoRI and HindIII sites but with a polylinker region identical to pUC19 (Weinstock, P. H. and Wetmur, J. G., *Nucleic Acids Res.* 18: 4207–4213 (1990)). One primer was selected from one of the two PvuII-containing primers described herein (SEQ ID NO: 14 or SEQ ID NO: 15). The reverse primer was synthesized to match either the BamHI-containing region of pMS19 or the corresponding region of one of the pUC19 derivatives. Two types of primer-template mismatches can thus be prepared and each seen in two contexts. The additional 35 bp in PCR products derived from pMS19 permitted easy identification of products following polyacrylamide gel electrophoresis and ethidium bromide staining. Quantitative autoradiography can also be employed to identify products. In addition to mismatch type (especially GT and AC mismatches and single frameshift mutations), efficiency of inhibition of amplification by MutS binding also depends on PCR conditions and the location of the mismatch within the primer.

Mismatches not only affect the melting temperature of the primer-template complex (Wetmur, J. G., Crit. Rev. Biochem. Mol. Biol. 26, 227–259 (1991)), but also the initiation of extension by the thermostable DNA polymerase. Template ratios may need adjustment to produce equal yields of the PCR products from the two templates in the absence of Apy or Tma MutS.

The effect of Apy and Tma MutS on the ratio of PCR products can be examined as a function of MutS concentration and thermostable DNA polymerase concentration. This ratio must be high enough to permit nearly complete MutS binding to first-round primer template complexes before the polymerase has an opportunity to bind and initiate extension. Cycling parameters can be adjusted as appropriate. Input template concentration and KCl and $Mg^{++}$ concentrations can also be adjusted. Compatibility of the system with dI and dU incorporation may also be examined.

Allele-Specific Amplification With A Mismatched Internal Oligonucleotide

Allele-specific amplification with mismatched internal oligonucleotide demonstrates that propagation of polymerization can be inhibited by forming a MutS-internal duplex mismatch complex. Unlike the previous allele-specific system, MutS-mediated selective amplification occurs at each PCR cycle, if needed. The assay can be based on the "Taqman" system described by Holland, P. M. et al., Proc. Natl. Acad. Sci. USA 88: 7276–7280 (1991).

One example of a PCR template mixture is equimolar pUC19GC and either pUC19, pUC19Δ1 or pUC19Δ3. One set of primers can be the two PvuII-containing primers described previously (SEQ ID NO: 14 and SEQ ID NO: 15). Additional primers can be synthesized to produce longer PCR products. A third Taqman oligonucleotide can match either the BamHI-containing region of pUC19GC or the corresponding region of one of the other templates. Many of these oligonucleotides can be synthesized. These oligonucleotides can contain a 3' terminal phosphate residue to prevent extension by Taq DNA polymerase, which lacks a 3'→5' exonuclease activity.

When present at a concentration in excess of the PCR primer concentrations, Taqman oligonucleotide-template complexes form efficiently, and bound Taqman oligonucleotide is degraded by the 5'→3' exonuclease activity of Taq polymerase during the polymerization step of PCR. All of the assay conditions can be tested for efficient degradation of radiolabeled Taqman oligonucleotides. Because only the PCR product from the pUC19GC template can be cleaved by AvaII and only the PCR products from the other templates can be cleaved by BamHI, the relative yields of the two PCR products can be determined by cleavage with AvaII, BamHI or both enzymes, gel electrophoresis, and fluorography or autoradiography. Adjustments in template concentration can be made to assure equal yield of the two PCR products.

E. coli MutS is known to not only inhibit the exonuclease activity of T7 DNA polymerase but also RecA-mediated strand displacement reactions (Worth, L., Jr. et al., Proc. Natl. Acad. Sci. USA 91: 3238–3241 (1994)). Thus, Apy and Tma MutS proteins will be examined for their ability to recognize Taqman oligonucleotide-template complexes and inhibit the propagation step of polymerization during PCR.

Taq DNA polymerase has a processivity of about 60 nucleotides at the maximum rate of polymerization (about 50 nucleotides/second). When Taq polymerase encounters a MutS-mismatch complex, the most likely scenario is dissociation of the polymerase. However, if a bound polymerase is capable of displacing the MutS complex, altering the salt conditions, the dNTP concentrations, the temperature or the enzyme (e.g. Stoffel fragment of Taq DNA polymerase) in a manner leading to reduced processivity, should lead to dissociation. These variables as well as input template concentration and the number of PCR cycles can be optimized. In addition to selection at each PCR cycle, another advantage of inhibition of propagation rather than initiation is that more time will be available for the formation of the thermostable MutS-mismatch complex before the critical polymerase inhibition step takes place. The separation of the primer and Taqman oligonucleotides on the templates is an additional variable.

Enhanced PCR Fidelity

Enhanced PCR fidelity depends upon the ability of Apy or Tma MutS proteins to bind to mismatches at the PCR strand-separation temperature, thus providing a nucleus for effectively instant renaturation of the PCR product upon cooling. A renatured PCR product would not act as a template for subsequent amplification. Apy and Tma MutS are ideal candidates because they were cloned from hyperthermophiles.

As described in the Examples, a simple blue-white screen was developed for measuring PCR fidelity. A plasmid derived from pUC19 was kindly provided by Dr. Y. Ioannou (Mount Sinai School of Medicine) in which the 880 bp sequence from the AatII site (GACGTC . . . ) to the AflIII site ( . . . ACATGT) was replaced by GACTCTAGAG-GATCCATGT (SEQ ID NO: 16), introducing an XbaI site and a BamHI site. pET11a (Novagen, Inc.) was cleaved with BstYI to produce ends compatible with BamHI and ligated into the BamHI-cleaved modified pUC19 vector. A clone was selected which contained the pET11a fragment from 748 to 1961, containing the complete $lacI^q$ gene, and was designated pUC17I. E. coli KL318 (K.B. Low) was obtained from the E. coli Genetic Stock Center (#4350). This lacI22 strain was constitutive for expression of lacZ and able to cleave X-gal (X-gal is 5-bromo-4-chloro-3-indolyl-β-D-galactoside) to produce a blue color. Transformation by pUC17I led to expression of $lacI^q$ and repression of lacZ. One set of PCR primers, 5' AUGAUGAUGAUGAUCGCACATTTCCC-CGAAAAGTG 3' (SEQ ID NO: 17) and 5' AUCAUCAU-CAUCAUGCGCGGAACCCCTATTTGT 5' (SEQ ID NO: 18), was used to amplify pUC17I. The products were phenol/chloroform extracted and purified on Millipore Ultrafree MC 30,000 NMWL filters before digestion with one unit UDG (UDG is uracil-DNA glycosylase) in 30 mM Tris (pH 8.3), 50 mM KCl, 5 mM $MgCl_2$ for 1 hr at 37° C. The circularized products were introduced into E. coli KL318 by electroporation. An alternative set of PCR primers was prepared which required restriction endonuclease cleavage and ligation before electroporation. In both cases, the cells were propagated at several dilutions on plates containing ampicillin, IPTG and X-gal. In both cases, the presence of a subset of blue colonies indicated failure to produce active $LacI^q$ due to a mutation introduced during PCR. There was little advantage of one set of primers and cloning conditions over the other.

Amplification reactions can be carried out with or without added Apy or Tma MutS protein. The relative numbers of blue colonies is a measure of the efficacy of the thermostable MutS proteins in blocking mismatch-containing PCR products, resulting from polymerization errors, from acting as templates in subsequent rounds of PCR.

Several thermostable DNA polymerases (e.g., Taq, Vent) may be suitable in the amplification reaction. Initially, published PCR conditions known to optimize for fidelity of a particular polymerase can be used, and PCR conditions can be varied to verify optimum polymerase fidelity. Subsequently, each of the appropriate variables affecting PCR can be modified to optimize for replication fidelity in the presence of Apy and Tma MutS, even if polymerase fidelity in the absence of a thermostable MutS protein is suboptimal. The optimized results in the presence of thermostable MutS proteins can be compared to the optimized results without MutS to determine the fold improvement in PCR fidelity for the two MutS proteins for each of the polymerases.

Decreased Stuttering/Slippage At Dinucleotide and Trinucleotide Repeats

Amplification of the highly polymorphic dinucleotide and trinucleotide repeats in human genomic for gene mapping usually results in ladders of bands thought to be due to polymerase "stuttering"/"slippage." D10S183 (MFD200, 124–158 bp) and D4S171 (MFD22, 143–161 bp) were used to amplify human genomic DNA. One primer was labeled with $^{32}$P. The products were separated on DNA sequencing gels and analyzed by autoradiography. The expected ladders of bands were observed. It is reasonable to expect that one or more sets of primers for highly polymorphic trinucleotide repeats can also be found which will give reproducible ladders with a spacing of 3 nucleotides.

Whatever the mechanism of stuttering/slippage, the ladders must reflect denaturation and amplification of PCR intermediates with 2 or 3 nucleotide loops similar to those found in heteroduplexes formed between pUC19Δ3 and pUC19Δ1 or pUC19GC, respectively. If thermostable MutS proteins prevents complete strand separation of these templates, these ladders can be reduced or eliminated, thus making the use of these polymorphic markers more convenient for genomic mapping and fingerprinting.

Amplification of representative di- and trinucleotide repeat regions of human DNA can be carried out in the presence and absence of Apy or Tma MutS to optimize conditions. Each of the appropriate variables affecting PCR can be modified to optimize for replication fidelity in the presence of Apy and Tma MutS, as measured by reduction or elimination of stuttering/slippage.

As used herein, the terms "template", "template nucleic acid", "target template" and "target nucleic acid" are defined as a nucleic acid, in purified or nonpurified form, which comprises the specific sequence desired (nucleic acid of interest). Any nucleic acid can be utilized as the template. The nucleic acid can be obtained from any source, for example, from plasmids such as pBR322, from cloned DNA or RNA, or from natural DNA or RNA from any source, including bacteria, yeast, viruses, organelles, and higher organisms such as plants and animals. DNA or RNA may be extracted from blood, tissue material such as chorionic villi, or amniotic cells by a variety of techniques. (See, e.g., Sambrook, J. et al., *Molecular Cloning, A Laboratory Manual*, 2nd edition, Cold Spring Harbor: Cold Spring Harbor University Press (1989)). Thus, the template may be DNA or RNA, including messenger RNA, which DNA or RNA may be single-stranded or double-stranded. In addition, a DNA-RNA hybrid which contains one strand of each may be utilized. A mixture can also be used, as can nucleic acids produced from a previous amplification reaction (using the same or different primers). The template may be only a fraction of a large molecule or can be present initially as a discrete molecule, so that the specific sequences constitutes the entire nucleic acid.

If the nucleic acid is double-stranded, it is necessary to separate the strands of the nucleic acid before it can be used as the template. This strand separation can be accomplished by any suitable denaturing method including physical, chemical or enzymatic means. One preferred physical method of separating the strands of the nucleic acid involves heating the nucleic acid until it is completely (>99%) denatured. Typical heat denaturation involves temperatures ranging from about 90° to 105° C. for times generally ranging from about 0.5 to 5 minutes. Preferably the effective denaturing temperature is 90°–100° C. for 0.5 to 3 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, *CSH-Quantitative Biology*, 43: 63 (1978), and techniques for using RecA are reviewed in C. Radding, *Ann. Rev. Genetics*. 16: 405–437 (1982). The denaturation produces two separated complementary strands of equal or unequal length.

The term "oligonucleotide" as used herein is defined as a molecule comprised of 8 or more deoxyribonucleotides and typically 20–40 deoxyribonucleotides. Its exact size will depend on many factors, which in turn depend on the ultimate function or use of the oligonucleotide. The oligonucleotide may be derived synthetically or may be isolated from natural sources by cloning, for example.

As used herein, an oligonucleotide which is designed to be completely complementary to a specific nucleic acid sequence of interest hybridizes to the complementary region of the strand of the template which includes the nucleic acid sequence of interest to form a homoduplex nucleic acid. The oligonucleotide which is designed to be completely complementary to a specific nucleic acid sequence of interest hybridizes to a strand of a nucleic acid which does not include the nucleic acid sequence of interest to form a heteroduplex nucleic acid. An oligonucleotide which is designed to be completely complementary to a specific nucleic acid sequence of interest can be a primer, a blocking oligonucleotide or a probe.

The term "primer" as used herein refers to an oligonucleotide, whether occurring naturally as in a purified restriction digest for example, or produced synthetically, which is capable of acting as a point of initiation of synthesis when placed under conditions in which primer extension is initiated. Synthesis of a primer extension product which is complementary to a nucleic acid strand is usually initiated in the presence of four different nucleoside triphosphates and an inducing agent such as DNA polymerase in an appropriate buffer and at a suitable temperature and pH. The specific buffer, temperature and pH depend on the inducing agent and the amplification method used.

The primer is preferably single stranded for maximum efficiency in amplification, but may alternatively be double stranded. If double stranded, the primer is first treated to separate its strands before being used to prepare extension products. The primer, as used in nucleic acid amplification reactions, is single-stranded. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the oligonucleotide primer typically contains 15–25 or more nucleotides, although it may contain fewer nucleotides. For other applications, the oligonucleotide primer is typically shorter, e.g., 8–15 nucleotides. Such short primer molecules generally require cooler temperatures to form sufficiently stable hybrid complexes with template.

The term "blocking oligonucleotide" refers to an oligonucleotide, whether occurring naturally as in a purified restriction digest or produced synthetically, which is capable of inhibiting propagation of polymerization of a primer extension product (i.e., inhibiting elongation of the extension product) when placed under conditions in which primer extension product is elongated. Propagation of a primer extension product which is complementary to a nucleic acid strand typically occurs in the presence of four different nucleoside triphosphates and an inducing agent such as DNA polymerase and at a suitable temperature and pH.

The blocking oligonucleotide is preferably single stranded for maximum efficiency in amplification, but may alternatively be partially complementary. For DNA amplification methods, the blocking oligonucleotide is an oligodeoxyribonucleotide. The blocking oligonucleotide must be sufficiently long to permit formation of the heteroduplex template-blocking oligonucleotide complex. The exact lengths of the blocking oligonucleotides will depend on many factors, including temperature, source of primer and use of the method. The blocking oligonucleotide must be modified at the 3' end to prevent its function as a primer (e.g., modified with 3' phosphate with Taq polymerase). The "Taqman oligonucleotide" is an example of a blocking oligonucleotide.

The term "probe" as used herein refers to an oligonucleotide, whether occurring naturally as in a purified restriction digest for example, or produced synthetically, which is capable of being covalently fused or ligated together into a product which is complementary to a nucleic acid strand of the target template when placed under conditions in which product formation is initiated. Formation of a product which is complementary to a nucleic acid strand is initiated in the presence of a fusing agent such as DNA ligase in an appropriate buffer and at a suitable temperature and pH. The specific buffer, temperature and pH will depend on the fusing agent and the amplification method used.

The probe is preferably single stranded for maximum efficiency in amplification, but may alternatively be double stranded. If double stranded, the probe is first treated to separate its strands before being used to prepare amplified products. The probe, as used in nucleic acid amplification reactions, is single-stranded. Preferably, the probe is an oligodeoxyribonucleotide. The probe must be sufficiently long to provide the desired specificity (i.e., to avoid being hybridized to random sequences in a sample). Typically, probes on the order of 15 to 100 bases serve this purpose. The exact lengths of the probes will depend on many factors, including temperature, source of primer and use of the method.

In one embodiment, oligonucleotides designed to be completely complementary to a specific nucleic acid sequence of interest, whether a primer, blocking oligonucleotide, or probe, can be designed for use in pairs, one oligonucleotide to anneal to and block the amplification of each complementary strand of the template, for example, in a control sample (i.e., in a sample of nucleic acids known to not include the nucleic acid sequence of interest). Complementary overlap between oligonucleotides designed to be completely complementary to a specific nucleic acid sequence of interest should be minimized to avoid the stable annealing of the oligonucleotides to each other.

In another embodiment, oligonucleotides designed to be completely complementary to a specific nucleic acid sequence of interest, whether a primer, blocking oligonucleotide, or probe, can be designed for use as a single oligonucleotide, annealing to and blocking the amplification of one strand of the template, for example, in a control sample (i.e., in a sample of nucleic acids known to not include the nucleic acid sequence of interest).

The following is an illustration of the use of MutS protein with oligonucleotides designed to be completely complementary to a specific nucleic acid sequence of interest to test for the presence of the nucleic acid sequence in a sample of nucleic acids or mixture of nucleic acids. The sample of nucleic acids may be purified or unpurified, as in a sample of lysed cells or tissue.

For use in a method for detecting a nucleic acid which includes a specific nucleic acid sequence, an oligonucleotide, whether a primer, a blocking oligonucleotide or a probe, is selected to be completely complementary to the nucleic acid sequence of interest. If the nucleic acid sequence of interest is included in the nucleic acid being assessed, the oligonucleotide will hybridize to the complementary region of the strand of the nucleic acid which includes the nucleic acid sequence of interest to form a homoduplex nucleic acid. MutS protein does not bind to a homoduplex nucleic acid and thus, in the case where the oligonucleotide selected is a primer, initiation of polymerization of a primer extension product occurs (the desired amplification product is synthesized).

If initiation of polymerization of a primer extension product is blocked, then the specific sequence thought to be included in the nucleic acid is likely not included in the nucleic acid. In this case, a nucleic acid strand and the primer have formed a heteroduplex containing a bulge loop which has been bound by MutS, indicating the presence of a mismatch or small insertion or deletion in the nucleic acid strand related to the primer.

In the case where the oligonucleotide selected is a blocking oligonucleotide, propagation of polymerization of a primer extension product (i.e., elongation of the extension product) occurs (the desired amplification product is synthesized). If propagation of polymerization of a primer extension product (i.e., elongation of the extension product) is blocked, then the nucleic acid sequence thought to be included in the nucleic acid is likely not included in the nucleic acid. In the case where the oligonucleotide selected is a probe, amplification of target nucleic acid occurs. If amplification of the nucleic acid is blocked, then the nucleic acid sequence thought to be included in the nucleic acid is likely not included in the nucleic acid. The amount of amplification product synthesized in each case is referred to herein as the amount of amplification product synthesized in a sample which comprises template nucleic acids assessed for the nucleic acid sequence of interest.

As a negative control, a mixture containing (1) a nucleic acid which does not have the specific nucleic acid sequence thought to be included in the template being evaluated and (2) the oligonucleotide designed to be completely complementary to the nucleic acid sequence thought to be included in the template being evaluated, is put under (a) conditions in which primer extension is initiated in the case where the oligonucleotide is a primer or under (b) conditions in which primer extension product is elongated in the case where the oligonucleotide is a blocking oligonucleotide or under (c) conditions in which target template is amplified in the case where the oligonucleotide is a probe. The amount of amplification product synthesized in the control is compared to the amount of amplification product synthesized in a sample which comprises template nucleic acids assessed for the nucleic acid sequence of interest. If the amount of amplification product synthesized in the sample which comprises template nucleic acids assessed for the nucleic acid sequence of interest is the same as or less than the amount of amplification product synthesized in the control, the nucleic acid sequence of interest is likely not included in the template nucleic acid. In the case of the opposite result (if the amount of amplification product synthesized in the sample which comprises template nucleic acids assessed for the nucleic acid sequence of interest is greater than the amount of amplification product synthesized in the control), the nucleic acid sequence of interest is likely included in the template nucleic acid.

In a method for selecting against a nucleic acid comprising a specific sequence, an oligonucletide is designed to form heteroduplexes with a strand of the nucleic acid being selected against. That is, the oligonucletide is designed to be less than completely complementary to the nucleic acid sequence being selected against (but sufficiently complementary that hybridization occurs). An oligonucleotide which is less than completely complementary to the nucleic acid sequence being selected against comprises one or more nucleotide mispairings with a nucleic acid strand in the region of the specific sequence being selected against when the oligonucleotide and nucleic acid strand hybridize together in that region, resulting in the formation of a bulge loop in the heteroduplex nucleic acid. An oligonucleotide which is less than completely complementary to the nucleic acid sequence being selected against can be a primer, a blocking oligonucleotide or a probe.

Oligonucleotides may be prepared using any suitable method, such as, for example, the phosphotriester and phosphodiester methods, or automated embodiments thereof. In one such automated embodiment diethylphosphoramidites are used as starting materials and may be synthesized as described by Beaucage et al., *Tetrahedron Letters* 22: 1859–1962 (1981). One method for synthesizing oligonucleotides on a modified solid support is described in U.S. Pat. No. 4,458,066. It is also possible to use a primer which has been isolated from a biological source (such as a restriction endonuclease digest).

The thermostable proteins of the present invention which specifically bind to bulge loops in a heteroduplex nucleic acid may be used in any methods of amplification of nucleic acids to improve fidelity or to improve allele-specific amplification. For example, the binding of thermostable proteins such as MutS proteins to DNA containing replication errors caused by misincorporation by a DNA polymerase, can improve the fidelity of the sequence of DNA in amplification methods, and has applications, for example, in the cloning of a true copy of genomic DNA. Where searching or assaying for DNA of a specific sequence among a mixture of many DNA molecules, methods of DNA amplification rely on the specificity of primer oligonucleotides annealing to a perfectly matched complementary strand in the template DNA. The addition to amplification reactions of a thermostable protein that binds to bulge loops formed when primer-template mismatches occur, and that prevents extension from the primer, can eliminate or greatly reduce the amplification from sites at which the primer-template complementarity is less than perfect. Variations on this method can be used to detect specific nucleic acid sequences that occur in cancer and in various genetic diseases.

The methods of the present invention are based on known methods of amplification of nucleic acids. Reagents used in the methods can be added sequentially or simultaneously. If a method of strand separation, such as heat, is employed which will inactivate the inducing agent, as in the case of a heat-labile enzyme, then it is necessary to replenish the inducing agent after every strand separation step.

PCR is an example of an amplification technique. PCR refers to an amplification technique where a pair of primers (one primary and one secondary) is employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to increase geometrically the number of target sequence molecules. PCR is described further in U.S. Pat. Nos. 4,683,195; 4,683,202; 4,800,159; and 4,965,188. Many variations of PCR are known. (See, e.g., Ausubel, F. M. et al., eds. *Current Protocols in Molecular Biology*, Greene Publishing Associates and John Wiley & Sons Inc., (1993))

LCR is another example of an amplification technique. LCR refers to an amplification technique where two primary (first and second probes) and two secondary (third and fourth) probes are employed in excess. The first probe hybridizes to a first segment of the target strand and the second probe hybridizes to a second segment of the target strand, the first and second segments being contiguous so that the primary probes abut one another in 5' phosphate-3' hydroxyl relationship and so that a ligase can covalently fuse or ligate the two probes into a fused product. In addition, a third (secondary) probe can hybridize to the first probe and a fourth (secondary) probe can hybridize to the second probe in a similar abutting fashion. If the target is initially double stranded, the secondary probes will also hybridize to the target complement in the first instance. Once the fused strand of primary probes is separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described further in, for example, EP-A-320 308.

The methods herein may be used to enable detection and/or characterization of specific nucleic acid sequences associated with infectious diseases, genetic disorders or cellular disorders such as cancer, e.g., oncogenes.

One embodiment of the invention relating to detecting nucleic acid which include a specific sequence comprises (a) combining an amplification reaction mixture which comprises nucleic acids to be assessed for the nucleic acid sequence of interest, oligonucleotides which are completely complementary to the specific nucleic acid sequence of interest, and a thermostable protein which binds specifically to bulge loops in a heteroduplex nucleic acid thereby producing a combination; (b) maintaining the combination of step (a) under conditions appropriate for amplification of nucleic acids to occur (i.e., synthesis of extension product); (c) determining the amount of extension products synthesized in the combination; and (d) comparing the amount of extension product determined in step (c) (i.e., the amount of extension product synthesized in the combination) with the amount of product synthesized in a corresponding control, wherein if the amount of product synthesized in the combination is the same as or less than the amount of product synthesized in the corresponding control, then the nucleic acid does not include the specific nucleic acid sequence.

As discussed above, oligonucleotides which are designed to be completely complementary to the nucleic acid sequence of interest can be designed for use in pairs, one oligonucleotide to anneal to and block the amplification of each complementary strand of the template, for example, in a control sample (i.e., in a sample of nucleic acids known to not include the nucleic acid sequence of interest). The oligonucleotides can also be designed for use as a single oligonucleotide, annealing to and blocking the amplification of one strand of the template, for example, in a control sample (i.e., in a sample of nucleic acids known to not include the nucleic acid sequence of interest).

The amplification reaction mixture and amplification conditions will depend on the particular amplification reaction being employed. The amplification reaction mixture will further depend on whether the nucleic acid sequence of interest is in, for example, a region of high GC content or a region of high AT content.

An example of an amplification mixture is one comprising (1) four different nucleoside triphophates; (2) two oligonucleotide primers where each primer is selected to be complementary to different strands of the nucleic acid to hybridize therewith, with one primer completely complementary to the nucleic acid sequence of interest, such that the extension product synthesized from one primer, when separated from its complement, can serve as a template for synthesis of the extension product of the other primer, at a temperature which promotes hybridiztion of each primer to its complementary strand; (3) a blocking oligonucleotide completely complementary to the complementary strand of the nucleic acid sequence of interest; (4) a thermostable enzyme which catalyzes combination of the nucleoside triphosphates to form primer extension products complementary to each strand of the nucleic acid; (5) a nucleic acid to be assessed for the nucleic acid sequence of interest; (6) and an amplification buffer suitable for the activity of the enzyme. Alternatively, the blocking oligonucleotide can be omitted.

Another example of an amplification reaction mixture comprises (1) four different nucleoside triphophates; (2) two oligonucleotide primers where each primer is selected to be complementary to different strands of the nucleic acid to hybridize therewith, such that the extension product synthesized from one primer, when separated from its complement, can serve as a template for synthesis of the extension product of the other primer, at a temperature which promotes hybridiztion of each primer to its complementary strand; (3) two blocking oligonucleotides, each designed to be completely complementary to different strands of the nucleic having the nucleic acid sequence of interest; (4) a thermostable enzyme which catalyzes combination of the nucleoside triphosphates to form primer extension products complementary to each strand of the nucleic acid; (5) a nucleic acid to be assessed for the nucleic acid sequence of interest; (6) and an amplification buffer suitable for the activity of the enzyme. Alternatively, one of the two blocking oligonucleotide can be omitted.

Oligonucleotide-template hybridizations are more stable in regions of high GC content than in regions of high AT content. Thus, if the nucleic acid sequence of interest is in, for example, a region of high GC content, one embodiment of the invention can be to select primers to be complementary to different strands of the nucleic acid to hybridize therewith, with one primer completely complementary to the nucleic acid sequence of interest, and a blocking oligonucleotide completely complementary to the complementary strand of the nucleic acid sequence of interest. If the nucleic acid sequence of interest is in, for example, a region of high AT content, one embodiment of the invention can be to select two oligonucleotide primers to be complementary to different strands of the nucleic acid to hybridize therewith and two blocking oligonucleotides, each designed to be completely complementary to different strands of the nucleic acid sequence of interest.

A third example of an amplification reaction mixture comprises (1) four oligonucleotide probes, two primary and two secondary probes as defined above, with one primary probe completely complementary to the nucleic acid sequence of interest and one secondary probe completely complementary to the complementary strand of the nucleic acid sequence of interest, (2) a thermostable enzyme which catalyzes fusion of oligonucleotide probes to form amplified products complementary to each strand of the nucleic acid; (3) a nucleic acid to be assessed for the nucleic acid sequence of interest; (4) and an amplification buffer suitable for the activity of the enzyme. Alternatively, one of the probes which is completely complementary to the nucleic acid sequence of interest can be omitted. These three examples of amplification reaction mixtures are not intended to be limiting in any way. The amplification reaction mixture and amplification conditions will depend upon the particular amplification reaction being employed and can be determined from readily available sources.

Stabilizers can be included in the methods of the present invention. As used herein, for example, stabilizers increase the lifetime of a thermostable bulge loop-binding protein-heteroduplex complexes. For example, stabilizers herein increase the lifetime of MutS-heteroduplex complexes. A MutS-heteroduplex complex is a complex formed when MutS is bound to a bulge loop in a heteroduplex nucleicacid. ATPγS is an example of a stabilizer.

The present invention will now be illustrated by the following examples, which are not intended to be limiting in any way.

EXAMPLES

Example 1

Genomic DNA, Plasmids, Nucleotides and Enzymes

All DNA manipulations used standard techniques and procedures (Sambrook, J. et al., *Molecular Cloning, A Laboratory Manual*, 2nd edition, Cold Spring Harbor: Cold Spring Harbor University Press (1989)). Genomic DNAs of *Thermotoga maritima* (Tma) and *Aquifex pyrophilus* (Apy) (Burggraf, S. et al., *System. Appl. Microbiol.* 15: 352–356 (1992)), both from cells supplied by Professor Karl Stetter, Universität Regensburg, were extracted for use as PCR templates and for Southern blots. Plasmids employed for cloning and expression were pUC19, pDG160/pDG182/pDG184 (Lawyer, F. C. et al., *PCR. Methods. Appl.* 2: 275–287 (1993)) and pET16b (Novagen, Inc.), which were grown in *E. coli* DH5α, DG116 (Lawyer, F. C. et al., *PCR. Methods. Appl.* 2: 275–287 (1993)) and BL21(DE3), respectively. All absorbance spectra were determined using a Hewlett-Packard diode array spectrophotometer equipped with a peltier temperature controller. Concentrations of DNA and primers were determined by using 50 and 36 μg ml$^{-1}$ A$_{260}$$^{-1}$, respectively, as conversion factors. Deoxynucleoside triphosphates were purchased from Boehringer-Mannheim. [α-$^{35}$S]dATP and [γ-$^{32}$P] ATP were purchased from NEN/DuPont. *E. coli* MutS protein was provided by U.S. Biochemical, Inc. UDG (uracyl DNA glycosylase, uracil N-glycosylase) was purchased from BRL, Inc. and used according to the manufacturer's instructions. Amplitaq DNA Polymerase, purchased from Perkin-Elmer, and native Taq polymerase, purchased from several suppliers, were used in the buffer supplied by the manufacturer. Restriction endonucleases, T4 polynucleotide kinase and T4 DNA ligase were purchased from New England Biolabs and used as recommended by the manufacturer. Simultaneous reactions with two or more restriction endonucleases were carried out in New England Biolabs NEB3 buffer. Simultaneous reactions with restriction endonucleases and T4 DNA ligase were carried out in the same buffer supplemented with 1 mM ATP.

Example 2

Oligodeoxynucleotides

All synthetic oligodeoxynucleotide primers for PCR and sequencing were synthesized on automated instruments using standard phosphoramidite chemistry. The initial degenerate sense primer
5' GCGGAATTCC(G/C)AACATGGG(G/C)GG(A/C/G/T)AA 3' (SEQ ID NO: 19) and antisense primer
5' GCGAGATCTAAGTAGTG(G/C)GT(A/C/G/T)GC(G/A)AA 3' (SEQ ID NO: 20), corresponding to amino acids 615–620 and 725–729 in *E. coli* MutS, were used for cloning a fragment of the Apy and Tma mutS genes. EcoRI (GAATTC) and BglII (AGATCT) recognition sequences are underlined.

Apy- and Tma-specific antisense primers,
5' GCGAGATCTCACCTGTCTTATGTAGCTCGA 3' (SEQ ID NO: 21) and 5' GCGAGATCTCATCTCGACAAG-GAACGTACT 3' (SEQ ID NO: 22), respectively, were employed together with a third degenerate sense primer,
5' GCGGAATTCATGGGGGA(C/T)TT(C/T)TA(C/T)GA 3' (SEQ ID NO: 23), corresponding to amino acids 33–38 in *E. coli* MutS. Specific inverse primers for use with near the 5' end of the known sequence were
5' GCGGAATTCGGGAAAGGATTCCCATGTTCG 3' (SEQ ID NO: 24) and 5' GCGAGATCTCCTTTCCA-GCGGGTCTTGAAG 3' (SEQ ID NO: 25) for Apy and 5' GCGGAATTCCGGGCATCCCGTACCACTCGC 3' (SEQ ID NO: 26) and 5' GCGAGATCTGGAGCGTCCCTGC-CCTTCTTG 3' (SEQ ID NO: 27) for Tma.

Specific inverse primers for use with near the 3' end of the known sequence were
5' GCGGAATTCTCAACCTTCATGAA-CGAGATG 3' (SEQ ID NO: 28) and 5' GCGAGATCTCGAGCCTATTCT-CATGAATAT 3' (SEQ ID NO: 29) for Apy and 5' GCG-GAATTCGAGGTGGGAAGAGGTACAAGC 3' (SEQ ID NO: 30) and 5' GCGAGATCTCATCTCGACAAG-GAACGTACT 3' (SEQ ID NO: 31) for Tma.

Additional sequencing primers lacking the GCG cap and restriction endonuclease sites were synthesized as required. These species-specific oligodeoxynucleotides were employed for Southern hybridization.

PCR primers for cloning Tma mutS genes into pDG160 were 5' GCGAAGCTTATGAAGGTAACTCCCCTCATG 3' (SEQ ID NO: 32) and 5' GCGGGATCCAC-GCATCGATACTGGTTAAAA 3' (SEQ ID NO: 33), where the BamHI and HindIII sites are underlined and the initiation codon in the forward primer is shown in bold italics.

PCR primers for cloning Apy mutS genes into pDG182 and pDG184 and pET16b were
5' GCGCCATGGGAAAAGAGGA-GAAAGAGCTCA 3' (SEQ ID NO: 34) and 5' GCGAGATCTGATACTCCA-GAGGTATTACAA 3' (SEQ ID NO: 35) where the NcoI, which contains the initiation codon, and BglII sites are underlined.

Example 3

DNA Amplification

PCR amplifications were carried out in a USA/Scientific Gene Machine II or an Ericomp PowerBlock System with DNA templates in 50–100 $\mu$l containing 1 $\mu$M of each primer, 10 mM Tris-HCl buffer, pH 8.3, 50 mM KCl, 25–50 units/ml Taq DNA polymerase, and 200 $\mu$M of each dNTP (Saiki, R. K. et al., *Science* 239: 487–491 (1988)). Typically, simultaneous reactions were initiated by addition of a $MgCl_2$ solution to $Mg^{++}$-free PCR mixtures at >80° C. to yield final concentrations of 0.8–2 mM followed by denaturation for 30 sec at 95° C. When using degenerate primers and 50 ng genomic DNA template, the first 5 cycles employed a 30 sec annealing step at 45° C. followed by a 2 min ramp to 72° C. before denaturation. An additional 30–35 cycles were carried out with a 55° C. annealing temperature. For inverse PCR (Ochman, H. et al., In PCR Protocols. A Guide to Methods and Applications, Innis, M. A. et al., Eds. (San Diego: Academic Press, Inc) pp. 219–227 (1990)), genomic DNA was digested to completion with a restriction endonuclease leaving a 3' or 5' 4-base overhang, phenol extracted, and ligated overnight at a DNA concentration of less than 50 $\mu$g/ml. When using unique direct or inverse PCR primers, templates of 50 ng genomic DNA or circularized genomic DNA, respectively, were employed, and the first 5 cycles were omitted.

Example 4

Cloning, Sequencing and Southern Hybridization

Products of PCR amplifications were phenol extracted to remove Taq polymerase and filtered on Millipore Ultrafree-MC 30,000 NMWL filter units to remove primers. PCR products with BglII cloning sites were cloned into pUC19 by simultaneous digestion of vector and insert with BglII, BamHI, and EcoRI, heat inactivation, ligation, and re-digestion with BamHI to destroy religated vectors without inserts. Inserts in pUC19, pDG160, pDG182, pDG184 and pET16b were sequenced in both orientations using insert-specific and vector-specific oligodeoxynucleotide primers with the Sequenase DNA Sequencing Kit (U.S. Biochemicals, Inc.) or by cycle sequencing with Taq DNA polymerase using either $^{32}$P-labeled primers (Gibco-BRL kit) or fluorescent dideoxy terminators on an Applied Biosystems Automated DNA Sequencer. Southern hybridizations of restriction endonuclease-cleaved genomic DNAs were carried out with oligodeoxynucleotides labeled with $^{32}$P using T4 polynucleotide kinase. The genomic DNAs and restriction endonucleases were (1) Apy, none; (2) Apy, HindIII; (3) Apy, SacI; (4) Tma, BglII; (5) Tma; HindIII; (6) Tth, BamHI; (7) Tth, SacI; (8) Tth, none; (9) Taq, partial SacI; (10) Taq, SacI.

Example 5

Computer Analysis

Nucleic acid and protein sequence analyses were carried out using programs in GCG (Devereux, J. et al., *Nucleic Acids Res.* 12: 387–395 (1984)). Mesophilic MutS and MutS-homolog protein sequences were obtained from Genbank 84.0 (Benson, D. et al., *Nucleic Acids Res.* 21: 2963–2965 (1993)). The MutS protein sequences from 3 Gram-negative and 1 Gram-positive mesophilic bacteria and the 7 available eukaryotic MutS homolog sequences were aligned with the 2 newly-determined thermophilic MutS sequences using PILEUP. The multiple alignments were truncated to include only amino acids corresponding to 8–794 of *E. coli* MutS prior to analysis using PHYLIP (Phylogeny Inference Package) version 3.5c (Felsenstein, J., *Cladistics* 5: 164–166 (1989)). Pairwise distances between amino acids in the MutS and MutS homolog sequences were calculated using PROTDIST with either the Dayhoff PAM matrix. Unrooted trees were calculated using FITCH with global rearrangement and jumbling before plotting with DRAWTREE.

Conserved motifs found in all MutS and MutS-homolog proteins, and in no other proteins in 38,303 sequences searched in GenBank, are GPNMxGKS and DExGRGT at positions 614 and 693, respectively, in *E. coli* MutS. A conserved sequence GDFYEXF at positions 19 in *E. coli* MutS is found only in prokaryotic MutS and MutS-homolog proteins. All three of these sequences were present in Apy and Tma MutS. Otherwise, Apy MutS and Tma MutS were 39 and 37% identical to Gram-positive *S. pneumonia* HexA (MutS-homolog protein) and 36 and 39% identical to Gram-negative *E. coli* MutS, whereas *S. pneumonia* HexA and *E. coli* MutS were 37% identical.

GCG calculations of the isoelectric points of MutS and MutS-type 2 homolog proteins in FIG. 10 gave 5.7±0.2 for eukaryotes and 5.6±0.5 for mesophilic prokaryotes. Apy MutS had a much higher calculated isoelectric point of 7.34, athough the value for Tma MutS was 6.1.

Example 6

Cloning and Sequence Analysis of Apy and Tma MutS Genes

The cloning of the thermophile mutS genes was accomplished without library construction using the same approach employed for the cloning of 4 thermophilic RecA proteins (Wetmur, J. G. et al., *J. Biol. Chem.* 269: 25928–25935 (1994)). Fragments of Apy and Tma mutS were amplified using a single set of degenerate PCR primers. Each primer began with GCG, followed by either an EcoRI or a BglII site, and followed by a degenerate sequence based on the amino acid sequences of two highly conserved and closely spaced regions of MutS proteins which were identical in *E. coli*, a Gram-negative organism and *Bacillus subtilis*, a Gram-positive organism. TFASTA analysis confirmed the specificity of these sequences for MutS proteins. The relatively close spacing (124 amino acids) was important to maximize specific PCR amplification and to minimize the likelihood of occurrence of EcoRI, BglII or BamHI sites which could interfere with subsequent cloning. The degeneracy of the primers was reduced by using G for purines and C for pyrimidines except near the 3' end where non-homology would have a deleterious effect on PCR. PCR amplification yielded unique products of the predicted length, which were cloned and sequenced. Although significant variation was observed for the translated sequence between the primers, both sequences were unmistakably those of MutS proteins. The combination of species-specific antisense primers based on the sequences of the amplified DNA fragments and one additional degenerate sense primer permitted amplification of 1.8 kb products from both Apy and Tma, which were cloned and sequenced.

Unique inverse PCR cloning primers were synthesized corresponding to sequences near the 5' and 3' ends of each of these sequences were use in amplifying circularized genomic DNA. PCR with circularized Tsp509I-digested and HindIII-digested Apy and Tma DNA yielded products containing the sequences of the 5' ends of the mutS genes and 108 nt of Apy and 195 nt of Tma upstream flanking sequence as well as the 3' ends of the mutS genes with 268 nt of Apy and 175 nt of Tma downstream flanking sequence.

A Southern blot was tested using sequence-specific oligodeoxynucleotides sequentially as probes. The Apy and Tma probes bound only to the Apy and Tma genomic DNA, respectively, but not to the DNA from two other species. These binding specificities demonstrated that the sequences amplified by PCR were derived from the sources stated.

The sequences of the Apy and Tma mutS genes are depicted in FIGS. 1 and 3, respectively. The guanine plus cytosine content (G+C%) of both was 47%. The translated sequence for Apy MutS is depicted in FIG. 2. The TFASTA analysis depicted in FIGS. 5A–5B for Apy and *E. coli* (853 amino acids) MutS shows 36% identity in 792 amino acids overlap with length differences at the N- and C-termini of only 2 and 6 amino acids, respectively. The translated sequence for Tma MutS is depicted in FIG. 4. The TFASTA analysis depicted in FIGS. 5A–5B for Tma and *E. coli* MutS shows a similar 37% identity in 783 amino acids overlap. However, Tma MutS showed significant variation at both the N- and C-termini. The analysis of the ends is outlined in FIG. 6. Following the last in-frame stop codon, the first ATG in Tma MutS matched the ATG at *E. coli* MutS codon 14. However, there were conserved threonine and proline codons at 3 and 2 positions upstream from this ATG in *E. coli*, Apy and Tma. Further examination of this upstream region revealed three valine codons. The most distal of these codons appeared to occur deep in the open reading frame of an upstream gene. The other two codons followed 5 and 11 nt after a sequence matching in 9 of 10 positions the 3' end of Tma 16S ribosomal RNA (Benson, D. et al., *Nucleic Acids Res.* 21: 2963–2965 (1993)). Because the 5 nt spacing separated the valine codon from the presumptive ribosome binding site by the optimal spacing, this codon was taken to be the initiation codon and was incorporated as ATG into the sense expression primer. The N-terminal was thus 7, rather than 13, and 5 amino acids shorter than *E. coli* and Apy MutS, respectively. The C-terminus of Tma MutS was 35 and 41 amino acids shorter than *E. coli* and Apy MutS, respectively. An investigation of the downstream flanking sequence revealed an open reading frame in reverse orientation which overlapped Tma MutS by 8 amino acids and which could encode a protein similar to that encoded by the D-ribulose-5-phosphate epimerase gene of *Alcaligenes eutrophus* and the dod gene of *Serratia marcescens*.

To be certain that the sequences to be incorporated into the 5'-PCR expression primers accurately reflected the sequence of the mutS genes, the genomic sequences surrounding the initiation codon were determined by cycle sequencing. Subsequently, both of the mutS genes were amplified using a 5'-PCR primer containing a GCG cap, a restriction endonuclease site, an initiation ATG and the next 20 nucleotides of the coding sequence and a 3'-PCR primer containing a GCG cap, a second restriction endonuclease site and 21 nucleotides antisense to the downstream flanking sequence. Products of several independent PCR reactions were digested with the appropriate restriction endonucleases and ligated into expression vectors. Clones which expressed a thermostable MutS were completely sequenced. The nuts sequences in FIG. 1 and FIG. 3 were assumed to be authentic because they were the same in at least two clones.

Example 7

Expression

PCR products resulting from use of the two sets of expression primers on the corresponding genomic DNAs were ligated into pDG160 (Tma), pDG182 (Apy) and pDG184 (Apy) for transformation of *E. coli* DG116 cells expressing the pLysS plasmid (Novagen, Inc) and growth at 30° C. on LB-AMP-chloramphenicol plates (LB is Luria Broth; Amp is ampicillin). The pLysS plasmid permits cell lysis by freeze-thaw. The Apy and Tma MutS PCR products were also ligated into pET16b and cloned into *E. coli* BL21(DE3) containing the pLysS plasmid. *E. coli* DG116 colonies derived from independent amplification reactions were grown overnight at 30° C. in LB-AMP-chloramphenicol, diluted 1/40 into the same medium and grown to $A_{600}$>1, induced at 42° C. for 15 min, grown for an additional 3–5 hrs at 39° C., and collected by centrifugation for 15 min at 6,000 g. E. coliBL21(DE3) colonies were grown overnight at 37° C. in LB-AMP-chloramphenicol, diluted 1/40 into the same medium and grown to $A_{600}$>1, induced with 1 mM isopropyl-A-D-thiogalactopyranoside (IPTG), grown for an additional 3–5 hrs, and collected by centrifugation for 15 min at 6,000 g.

The pellets were resuspended in 300 μl 50 mM Tris-HCl, 1 mM phenylmethylsulfonyl flouride (PMSF), 1 mM dithiothreitol (DTT) and 10 mM ethylene-diamine-tetra acetic acid (EDTA), pH 8 in a 1.5 ml microcentrifuge tube and subjected to 3 cycles of freezing in dry-ice ethanol and thawing at 37° C. Following sonication on ice with the microtip of a Heat Systems Sonifier Cell Disrupter at power level 7 for 30 sec to reduce the viscosity, cell debris was removed by microcentrifugation (10,000 g) for 5 min at 4° C. The samples were transferred to a new tube, made 0.3M $(NH_4)_2SO_4$ by addition of 3M stock, made 0.75% polyethylenimine by addition of a neutralized 10% stock to precipitate DNA, heated to 75° C. for 15 min to denature thermolabile proteins, placed on ice for 30 min to aggregate the denatured proteins, cleared of DNA and denatured proteins by microcentrifugation for 15 min at 4° C., transferred to a new tube and frozen at −20° C. The partially purified products were assayed for the presence of a thermostable protein of the correct size by sodium dodecylsulfate-polyacrylamide gel electrophoresis (SDS-PAGE).

Example 8
Purification

The partially purified products were loaded onto a BU hydrophobic chromatography column on a PerSeptive Biosystems BioCAD SPRINT perfusion chromatography system in 1.5M $(NH_4)_2SO_4$, 20 mM sodium phosphate, pH 7.0 and washed with the same buffer before elution with a linear gradient to 20 mM sodium phosphate, pH 7.0, 10% ethylene glycol. The solvent was then changed by dialysis. The final products were analyzed by SDS-PAGE, protein concentrations were determined using the by the Bio-Rad Protein Assay kit (Bradford), and complete absorbance spectra were determined to ensure removal of nucleic acids.

Purification of Apy MutS by BU hydrophobic chromatography on a PerSeptive Biosystems BioCAD SPRINT perfusion chromatography system led to an SDS-PAGE pure protein free of nucleic acids as determined by an $A_{280}/A_{260}$ ratio greater than 1.5. The overall yield of the thermostable MutS proteins from various preparations was approximately 0.2 mg/$10^{11}$ cells, corresponding to approximately 2.5% of the initial protein content of the cells.

Example 9
Mismatch Binding Assays

Several modifications were introduced into pUC19 by replacing the KpnI to PstI segment of the polylinker. In PUC19GC, the BamHI site GGATCC in the sequence GGGGATCCTC (SEQ ID NO: 10) was modified to substitute a C for the first T to yield GGGACCCTC. The resultant plasmid gained an AvaII site. In pUC19Δ1, a T was inserted into the pUC19GC polylinker sequence GGGACCCTC to yield GGGGATCCCTC (SEQ ID NO: 12) and reconstitute the BamHI site. In pUC19Δ3, a T and two Cs were inserted into the pUC19GC polylinker sequence GGGACCCTC to yield GGGGATCCCCCTC (SEQ ID NO: 13) and again reconstitute the BamHI site. The sequences were verified. PCR products of 337–340 bp were synthesized from the pUC19, pUC19GC, pUC19Δ1 and pUC19Δ3 using 5' TACGCCAGCTGGCGAAAGGG 3' (SEQ ID NO: 14) and 5' AATGCAGCTGGCACGACAGG 3' (SEQ ID NO: 15), where the PvuII sites are underlined. For some experiments, one of the primers was labeled with $^{32}P$ using T4 kinase. The yields were determined from ethidium bromide fluorescence in agarose gels. Heteroduplexes were formed in PCR buffer from various mixtures of two different PCR products by denaturation at 97° C. and annealing at 67° C. Unless otherwise specified, MutS binding assays employed a 1:20 dilution of a heteroduplex mixture or homoduplex control containing approximately 5 μg/ml DNA in PCR buffer into 20 mM Tris, pH 7.5, 5 mM $MgCl_2$, 0.1 mM DTT, 0.01 mM EDTA, 0.1 mM ATP. After incubation in the presence or absence of MutS protein, the products were separated by electrophoresis at 25 V/cm for 30 min on a 6% polyacrylamide gel at 4° C. in 0.2×TBE (TBE=89 mM TrisHCl, 89 mM borate, 1 mM EDTA, pH 8) and analyzed by ethidium bromide staining and UV fluorography or autoradiography.

The homoduplexes, differing by only three base pairs, had almost identical mobilities. The heteroduplexes had reduced mobility. Denaturation and fast cooling prevented complete renaturation and revealed a slower-moving denatured DNA band. Addition of Apy MutS protein led to a gel shift of the heteroduplex band and appearance of a new band for the complex. Denaturation and fast cooling in the presence of the thermostable Apy MutS demonstrated that the specific binding to the heteroduplex was preserved.

Apy MutS also survived a rapid denaturation step at 100° C. and retained binding specificity.

In another assay of binding specificity, MutS-heteroduplex complexes were formed at 70° C. and mixed with a vast excess of λ DNA before electrophoresis. Identical results were obtained whether the λ DNA was added at 70° C. or subsequent to the incubation. The λ DNA competed away non-specific complexes of Apy MutS to homoduplexes and heteroduplexes which were apparently stable during electrophoresis at 4° C. That is, Apy MutS specifically bound to bulge defects in the presence of vast excess of competing DNA lacking mismatches.

In another assay, a complex was formed between a heteroduplex of a small reassociation product (SRP) and a slight excess of Apy MutS as demonstrated by the disappearance of the heteroduplex band on the stained gel in the presence of λ DNA. A second larger heteroduplex of a large reassociation product (LRP) was added and aliquots were removed as a function of time. Apy MutS-heteroduplex complexes at 70° C. were stabilized by the addition of 1 mM ATPγS. The lifetime of the stabilized complex exceeded the time for a typical PCR cycle.

Example 10
Fidelity Assay

A plasmid derived from pUC19 was kindly provided by Dr. Y. Ioannou (mini-pUC19) (Mount Sinai School of Medicine) in which the 880 bp sequence from the AatII site (GACGTC . . . ) to the AflIII site ( . . . ACATGT) had been replaced by GACTCTAGAGGATCCATGT (SEQ ID NO: 16), introducing an XbaI site and a BamHI site. pET11a (Novagen, Inc.) was cleaved with BstYI to produce ends compatible with BamHI and ligated into the BamHI-cleaved modified pUC19 vector. A clone was selected which contained the pET11a fragment from 748 to 1961, containing the complete lacI$^q$ gene. E. coli KL318 (K. B. Low; E. coli Genetic Stock Center #4350) was obtained from the E. coli Genetic Stock Center (#4350). This lacI22 strain was constitutive for expression of lacZ and able to cleave X-gal to produce a blue color. Transformation by pUC17I (mini-pUC19+pET11a lacI$^q$ fragment) led to expression of lacI$^q$ and repression of lacZ. The PCR primers 5' A U G A U G A U G A U G A U C G C A C A T T T C -

CCCGAAAAGTG 3' (SEQ ID NO: 17) and 5' AUCAU-CAUCAUCAUGCGCGGAACCCCTATTTGT 5' (SEQ ID NO: 18) were used to amplify pUC17I either with or without added thermostable MutS protein. The products were phenol/chloroform extracted and purified on Millipore Ultrafree MC 30,000 NMWL filters before digestion with 1 unit uracil-N-glycosylase (UDG; BRL) in 30 mM Tris (pH 8.3), 50 mM KCl, 5 mM MgCl$_2$ for 1 hr at 37° C. The circularized products were introduced into E. coli KL318 by electroporation. The cells were propagated at several dilutions on plates containing ampicillin, IPTG and X-gal. Blue products indicated failed to produce active LacI$^q$ due to a mutation introduced during PCR.

Example 11
Repeated DNA Amplification

Primers for the highly polymorphic dinucleotide repeats at human D10S183 (MFD200, 124–158 bp) and D4S171 (MFD22, 143–161 bp) were used to amplify human genomic DNA either with or without added thermophilic MutS protein. One primers was labeled with $^{32}$P. The products were separated on DNA sequencing gels and analyzed by autoradiography.

Example 12
Allele-Specific Amplification With Mismatched Primers

Template mixtures containing various ratios of pMS19, which contained an insert at the HindIII site, and pUC19GC or another mismatch clone were amplified using a sense matching pUC19GC at the site of the mismatch and the antisense primer 5' AATGCAGCTGGCACGACAGG 3' (SEQ ID NO: 36) with or without added thermophilic MutS protein. The products were detected by polyacrylamide gel electrophoresis.

A further experiment was designed so that allele-specific PCR would preferentially amplify the larger band, the reverse of the tendency of PCR to preferentially amplify smaller bands. One of the templates was pMS19, which is pUC19 with additional sequence inserted at each end of the pUC19 polylinker. One pUC19 PCR primer was either (i) GGTACCCGGGGATCCTCTAG (SEQ ID NO: 37) (bulge with pUC19Δ1 or 3 forms at −5 to −7) or (ii) TACCCGGG-GATCCTCTAGAG (SEQ ID NO: 38) (bulge at −7 to −9). The second primer was one of the PvuII containing pUC19 primers. Template ratios were adjusted to equalize product without Apy MutS. Apy MutS-enhanced allele-specific PCR, by at least an order of magnitude, occurred using 20 cycles of amplification with Taq polymerase (denature 30 sec, 95° C.; anneal 30 sec; extend 30 sec, 72° C.) with added 0.5% Tween 20 and with KCl increased to 0.1M. That is, addition of Apy MutS protein to a PCR reaction has shown at least an order of magnitude in inhibition of initiation from mismatched primers on the input template (e.g., from mispaired bases and frameshifts of 1 and 3 nucleotides).

---

What is claimed is:

1. Isolated MutS obtained from bacteria selected from the group consisting of hyperthermophilic bacteria and thermophilic bacteria.

2. An isolated thermostable protein consisting of the contiguous amino acid sequence of SEQ ID NO: 2.

3. An isolated thermostable protein consisting of the contiguous amino acid sequence of SEQ ID NO: 5.

4. An isolated thermostable protein which binds specifically to bulge loops in a heteroduplex nucleic acid encoded by a nucleic acid characterized by the ability to hybridize under high stringency conditions to DNA consisting of the contiguous sequence of SEQ ID NO: 6.

5. An isolated thermostable protein which binds specifically to bulge loops in a heteroduplex nucleic acid encoded by a nucleic acid characterized by the ability to hybridize under high stringency conditions to DNA consisting of the contiguous sequence of SEQ ID NO: 7.

* * * * *